United States Patent
Kim et al.

(10) Patent No.: US 12,251,394 B2
(45) Date of Patent: Mar. 18, 2025

(54) METHODS FOR THE TREATMENT OF BLADDER CANCER

(71) Applicant: Eisai R&D Management Co., Ltd., Tokyo (JP)

(72) Inventors: Dae-Shik Kim, Andover, MA (US); Frank Fang, Andover, MA (US); Atsushi Endo, Andover, MA (US); Hyeong-Wook Choi, Andover, MA (US); Ming-Hong Hao, Quincy, MA (US); Xingfeng Bao, Concord, MA (US); Kuan-Chun Huang, Lexington, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 982 days.

(21) Appl. No.: 17/058,817

(22) PCT Filed: May 31, 2019

(86) PCT No.: PCT/US2019/034933
§ 371 (c)(1),
(2) Date: Nov. 25, 2020

(87) PCT Pub. No.: WO2019/232392
PCT Pub. Date: Dec. 5, 2019

(65) Prior Publication Data
US 2021/0205348 A1  Jul. 8, 2021

Related U.S. Application Data

(60) Provisional application No. 62/679,495, filed on Jun. 1, 2018, provisional application No. 62/826,347, filed on Mar. 29, 2019.

(51) Int. Cl.
*A61K 31/7084* (2006.01)
*A61P 35/04* (2006.01)

(52) U.S. Cl.
CPC .......... *A61K 31/7084* (2013.01); *A61P 35/04* (2018.01)

(58) Field of Classification Search
CPC ....... A61K 31/7084; A61P 35/00; A61P 35/04
USPC ............................. 424/9.1; 514/2, 1; 435/121
See application file for complete search history.

(56) References Cited

U.S. PATENT DOCUMENTS

| | | | |
|---|---|---|---|
| 5,547,941 A | 8/1996 | Battistini et al. | |
| 7,569,555 B2 | 8/2009 | Karaolis | |
| 7,592,326 B2 | 9/2009 | Karaolis | |
| 7,709,458 B2 | 5/2010 | Karaolis et al. | |
| 9,549,944 B2 | 1/2017 | Dubensky et al. | |
| 2007/0149462 A1 | 6/2007 | Iyer et al. | |
| 2014/0205653 A1 | 7/2014 | Dubensky et al. | |
| 2014/0329889 A1 | 11/2014 | Vance et al. | |
| 2014/0341976 A1 | 11/2014 | Dubensky et al. | |
| 2015/0056224 A1 | 2/2015 | Dubensky et al. | |
| 2016/0362441 A1 | 12/2016 | Vernejoul et al. | |
| 2017/0044206 A1 | 2/2017 | Altman et al. | |
| 2017/0158724 A1 | 6/2017 | Adams et al. | |
| 2018/0237468 A1* | 8/2018 | Kim ........................ A61P 35/02 | |
| 2019/0345192 A1* | 11/2019 | Kim ........................ A61P 31/04 | |

FOREIGN PATENT DOCUMENTS

| | | |
|---|---|---|
| CN | 102199183 A | 9/2011 |
| EP | 1740192 B1 | 6/2012 |
| WO | 2009133560 A1 | 11/2009 |
| WO | 2015074145 A1 | 5/2015 |
| WO | 2015077354 A1 | 5/2015 |
| WO | 2015185565 A1 | 12/2015 |
| WO | 2016100261 A2 | 6/2016 |
| WO | 2016120305 A1 | 8/2016 |
| WO | 2016145102 A1 | 9/2016 |
| WO | 2017027645 A1 | 2/2017 |
| WO | 2017027646 A1 | 2/2017 |
| WO | 2017075477 A1 | 5/2017 |
| WO | 2017093933 A1 | 6/2017 |
| WO | 2017123657 A1 | 7/2017 |
| WO | 2017175156 A1 | 10/2017 |
| WO | 2018098203 A1 | 5/2018 |
| WO | 2018140831 A2 | 8/2018 |
| WO | 2018152450 A1 | 8/2018 |
| WO | 2018152453 A1 | 8/2018 |
| WO | 2018198076 A1 | 11/2018 |
| WO | 2018198084 A1 | 11/2018 |
| WO | WO-2018200812 A1 * | 11/2018 ............. A61K 47/68 |
| WO | 2019043634 A2 | 3/2019 |
| WO | 2019046496 A1 | 3/2019 |
| WO | 2019046498 A1 | 3/2019 |
| WO | 2019046500 A1 | 3/2019 |
| WO | 2019046511 A1 | 3/2019 |

OTHER PUBLICATIONS

Berge, et al., "Pharmaceutical Salts", J. Pharm. Sci., Jan. 1977, vol. 66, No. 1, pp. 1-19.

Chandra, et al. "STING ligand c-di-GMP improves cancer vaccination against metastatic breast cancer" Cancer Immunol Res., Sep. 2014, vol. 2, pp. 901-910.

Corrales, et al., "Direct Activation of STING in the Tumor Microenvironment Leads to Potent and Systemic Tumor Regression and Immunity" Cell Rep., May 2015, vol. 11, pp. 1018-1030.

Corrales, et al., "The host STING pathway at the interface of cancer and immunity" J. Clin. Invest., Jul. 2016, vol. 126, No. 7, pp. 2404-2411.

Curran, et al. "STING Pathway Activation Stimulates Potent Immunity against Acute Myeloid Leukemia" Cell Rep., Jun. 2016, vol. 15, pp. 2357-2366.

(Continued)

*Primary Examiner* — Jane J Zara
(74) *Attorney, Agent, or Firm* — Buchanan Ingersoll & Rooney PC

(57) ABSTRACT

Provided herein are methods for the treatment of bladder cancer.

12 Claims, 19 Drawing Sheets
Specification includes a Sequence Listing.

(56) References Cited

OTHER PUBLICATIONS

Fu, et al., "STING Agonist Formulated Cancer Vaccines Can Cure Established Tumors Resistant to PD-1 Blockade", Sci. Translational Med., Apr. 2015, vol. 7(283), pp. 1-11.
International Search Report (PCT/ISA/210) and Written Opinion (PCT/ISA/237) mailed on Sep. 16, 2019, by the European Patent Office as the International Searching Authority for International Application No. PCT/US2019/034933.
Kamat, et al., "What is new in non-muscle-invasive bladder cancer in 2016?", Turk J Urol, Mar. 2017, vol. 43(1), pp. 9-13.
Lee, et al., "Tumor Establishment Features of Orthotopic Murine Bladder Cancer Models," Urological Oncology, Jun. 2012, vol. 53, pp. 396-400.
Ohkuri, et al., "Protective role of STING against gliomagenesis: Rational use of STING agonist in anti-glioma immunotherapy", Oncoimmunology, Apr. 2015, vol. 4 Issue 4, e999523-1 to e999523-2.
Tang, et al. "Agonist-Mediated Activation of STING Induces Apoptosis in Malignant B Cells" Cancer Res., Mar. 2016, vol. 76, pp. 2137-2152.
Woo, et al. "STING-dependent cytosolic DNA sensing mediates innate immune recognition of immunogenic tumors" Immunity, Nov. 2014, vol. 41, pp. 830-842.
Xia, et al., "Deregulation of STING Signaling in Colorectal Carcinoma Constrains DNA Damage Responses and Correlates With Tumorigenesis" Cell Reports, Jan. 2016, vol. 14, pp. 282-297.
Xia, et al., "Recurrent Loss of STING Signaling in Melanoma Correlates with Susceptibility to Viral Oncolysis" Cancer Res., Nov. 2016, pp. 6747-6759.
Yi, et al., "Single nucleotide polymorphisms of human STING can affect innate immune response to cyclic dinucleotides" PLoS One, Oct. 2013, vol. 8, issue 10, e77846, pp. 1-16.
Zhu, et al., "Cutting edge: STING mediates protection against colorectal tumorigenesis by governing the magnitude of intestinal inflammation" J. Immunol., Sep. 2014, pp. 4779-4782.
Zlotta, et al., "The management of BCG failure in non-muscle-invasive bladder cancer: an update," Can Urol Assoc J, Dec. 2009, vol. 3, issue 6, pp. S199-S205.
Lioux, et al., "Design, Synthesis, and Biological Evaluation of Novel Cyclic Adenosine-Inosine Monophosphate (cAIMP) Analogs That Activate Stimulator of Interferon Genes (STING)", J. Med. Chem., Oct. 2016, vol. 59, pp. 10253-10267.
Russian Search Report for RU 2020143303/04 filed May 31, 2019 dated Jan. 14, 2022 with English Translation.
Russian Official Action for RU 2020143303/04 filed May 31, 2019 dated Jan. 14, 2022 with English Translation.
Mashkovsky, "Medicaments," Moscow, "Medicine," 1993, Part 1, p. 8.
Liang, H., et al., Host STING-dependent MDSC mobilization drives extrinsic radiation resistance, Nature Communications, 8:1736, DOI: 10.1038/s41467-017-01566-5, www.nature.com/naturecommunications.

* cited by examiner

FIG. 12 Tumor volume plot for treated sc tumors and survival curve

Tumor volume plot for treated sc tumors and survival curve

SEQUENCE LISTING

<160> NUMBER OF SEQ ID NOS: 7

<210> SEQ ID NO 1
<211> LENGTH: 1140

```
<212> TYPE: DNA
<213> ORGANISM: Homo sapiens

<400> SEQUENCE: 1
atgccccact ccagcctgca tccatccatc ccgtgtccca ggggtcacgg ggcccagaag    60
gcagccttgg ttctgctgag tgcctgcctg gtgacccttt gggggctagg agagccacca   120
gagcacactc tccggtacct ggtgctccac ctagcctccc tgcagctggg actgctgtta   180
aacgggtct gcagcctggc tgaggagctg cgccacatcc actccaggta ccggggcagc   240
tactggagga ctgtgcgggc ctgcctgggc tgcccctcc gccgtggggc cctgttgctg   300
ctgtccatct atttctacta ctccctccca aatgcggtcg gccgcccctt cacttggatg   360
cttgccctcc tgggcctctc gcaggcactg aacatcctcc tgggcctcaa gggcctggcc   420
ccagctgaga tctctgcagt gtgtgaaaaa gggaatttca acgtggccca tgggctggca   480
tggtcatatt acatcggata tctgcggctg atcctgccag agctccaggc ccggattcga   540
acttacaatc agcattacaa caacctgcta cggggtgcag tgagccagcg gctgtatatt   600
ctcctcccat tggactgtgg ggtgcctgat aacctgagta tggctgaccc caacattcgc   660
ttcctggata aactgcccca gcagaccggt gaccgggctg gcatcaagga tcgggtttac   720
agcaacagca tctatgagct tctggagaac gggcagcggg cgggcacctg tgtcctggag   780
tacgccaccc ccttgcagac tttgtttgcc atgtcacaat acagtcaagc tggctttagc   840
cgggaggata ggcttgagca ggccaaactc ttctgccgga cacttgagga catcctggca   900
gatgccctg agtctcagaa caactgccgc tcattgcct accaggaacc tgcagatgac   960
agcagcttct cgctgtccca ggaggttctc cggcacctgc ggcaggagga aaaggaagag  1020
gttactgtgg gcagcttgaa gacctcagcg gtgcccagta cctccacgat gtcccaagag  1080
cctgagctcc tcatcagtgg aatggaaaag cccctccctc tccgcacgga tttctcttga  1140

<210> SEQ ID NO 2
<211> LENGTH: 1140
<212> TYPE: DNA
<213> ORGANISM: Homo sapiens

<400> SEQUENCE: 2
atgccccact ccagcctgca tccatccatc ccgtgtccca ggggtcacgg ggcccagaag    60
gcagccttgg ttctgctgag tgcctgcctg gtgacccttt gggggctagg agagccacca   120
gagcacactc tccggtacct ggtgctccac ctagcctccc tgcagctggg actgctgtta   180
aacgggtct gcagcctggc tgaggagctg cgccacatcc actccaggta ccggggcagc   240
tactggagga ctgtgcgggc ctgcctgggc tgcccctcc gccgtggggc cctgttgctg   300
ctgtccatct atttctacta ctccctccca aatgcggtcg gccgcccctt cacttggatg   360
cttgccctcc tgggcctctc gcaggcactg aacatcctcc tgggcctcaa gggcctggcc   420
ccagctgaga tctctgcagt gtgtgaaaaa gggaatttca acgtggccca tgggctggca   480
tggtcatatt acatcggata tctgcggctg atcctgccag agctccaggc ccggattcga   540
acttacaatc agcattacaa caacctgcta cggggtgcag tgagccagcg gctgtatatt   600
ctcctcccat tggactgtgg ggtgcctgat aacctgagta tggctgaccc caacattcgc   660
ttcctggata aactgcccca gcagaccggt gaccatgctg gcatcaagga tcgggtttac   720
agcaacagca tctatgagct tctggagaac gggcagcggg cgggcacctg tgtcctggag   780
tacgccaccc ccttgcagac tttgtttgcc atgtcacaat acagtcaagc tggctttagc   840
```

```
cgggaggata ggcttgagca ggccaaactc ttctgccgga cacttgagga catcctggca      900 gatgccctg agtctcagaa caactgccgc ctcattgcct accaggaacc tgcagatgac       960
agcagcttct cgctgtccca ggaggttctc cggcacctgc ggcaggagga aaaggaagag     1020
gttactgtgg gcagcttgaa gacctcagcg gtgcccagta cctccacgat gtcccaagag    1080
cctgagctcc tcatcagtgg aatggaaaag ccctccctc tccgcacgga tttctcttga    1140
```

<210> SEQ ID NO 3
<211> LENGTH: 1140
<212> TYPE: DNA
<213> ORGANISM: Homo sapiens

<400> SEQUENCE: 3

```
atgcccccact ccagcctgca tccatccatc ccgtgtccca ggggtcacgg ggcccagaag       60
gcagccttgg ttctgctgag tgcctgcctg gtgacccttt gggggctagg agagccacca      120
gagcacactc tccggtacct ggtgctccac ctagcctccc tgcagctggg actgctgtta      180 aacgggtct gcagcctggc tgaggagctg cgccacatcc actccaggta ccggggcagc      240
tactggagga ctgtgcgggc tgcctgggc tgcccctcc gccgtggggc cctgttgctg       300
ctgtccatct atttctacta ctccctccca aatgcggtcg gcccgccctt cacttggatg     360
cttgccctcc tgggcctctc gcaggcactg aacatcctcc tgggcctcaa gggcctggcc    420
ccagctgaga tctctgcagt gtgtgaaaaa gggaatttca acgtggccca tgggctggca    480
tggtcatatt acatcggata tctgcggctg atcctgccag agctccaggc ccggattcga    540
acttacaatc agcattacaa caacctgcta cggggtgcag tgagccagcg gctgtatatt    600
ctcctcccat tggactgtgg ggtgcctgat aacctgagta tggctgaccc caacattcgc    660
ttcctggata aactgcccca gcagaccgct gaccgagctg gcatcaagga tcgggttttac   720 agcaacagca tctatgagct tctggagaac gggcagcggg cgggcaccctg tgtcctggag   780 tacgccaccc ccttgcagac tttgtttgcc atgtcacaat acagtcaagc tggctttagc    840
cgggaggata ggcttgagca ggccaaactc ttctgccaga cacttgagga catcctggca    900 gatgccctg agtctcagaa caactgccgc ctcattgcct accaggaacc tgcagatgac     960
agcagcttct cgctgtccca ggaggttctc cggcacctgc ggcaggagga aaaggaagag  1020
gttactgtgg gcagcttgaa gacctcagcg gtgcccagta cctccacgat gtcccaagag 1080
cctgagctcc tcatcagtgg aatggaaaag ccctccctc tccgcacgga tttctcttga   1140
```

<210> SEQ ID NO 4
<211> LENGTH: 187
<212> TYPE: PRT
<213> ORGANISM: Homo sapiens

<400> SEQUENCE: 4

```
Val Ala His Gly Leu Ala Trp Ser Tyr Tyr Ile Gly Tyr Leu Arg Leu
1               5                   10                  15

Ile Leu Pro Glu Leu Gln Ala Arg Ile Arg Thr Tyr Asn Gln His Tyr
            20                  25                  30

Asn Asn Leu Leu Arg Gly Ala Val Ser Gln Arg Leu Tyr Ile Leu Leu
        35                  40                  45

Pro Leu Asp Cys Gly Val Pro Asp Asn Leu Ser Met Ala Asp Pro Asn
    50                  55                  60

Ile Arg Phe Leu Asp Lys Leu Pro Gln Gln Thr Gly Asp Arg Ala Gly
65                  70                  75                  80
```

```
Ile Lys Asp Arg Val Tyr Ser Asn Ser Ile Tyr Glu Leu Leu Glu Asn
                85                  90                  95
Gly Gln Arg Ala Gly Thr Cys Val Leu Glu Tyr Ala Thr Pro Leu Gln
            100                 105                 110
Thr Leu Phe Ala Met Ser Gln Tyr Ser Gln Ala Gly Phe Ser Arg Glu
        115                 120                 125
Asp Arg Leu Glu Gln Ala Lys Leu Phe Cys Arg Thr Leu Glu Asp Ile
    130                 135                 140
Leu Ala Asp Ala Pro Glu Ser Gln Asn Asn Cys Arg Leu Ile Ala Tyr
145                 150                 155                 160
Gln Glu Pro Ala Asp Asp Ser Ser Phe Ser Leu Ser Gln Glu Val Leu
                165                 170                 175
Arg His Leu Arg Gln Glu Glu Lys Glu Val
            180                 185

<210> SEQ ID NO 5
<211> LENGTH: 311
<212> TYPE: PRT
<213> ORGANISM: Artificial Sequence
<220> FEATURE:
<223> OTHER INFORMATION: His-TEV-Sumo-WT STING construct

<400> SEQUENCE: 5

Met His His His His His Ser Ser Gly Val Asp Leu Gly Thr Glu
1               5                   10                  15
Asn Leu Tyr Phe Gln Ser Asn Ala Met Ser Asp Ser Glu Val Asn Gln
                20                  25                  30
Glu Ala Lys Pro Glu Val Lys Pro Glu Val Lys Pro Glu Thr His Ile
            35                  40                  45
Asn Leu Lys Val Ser Asp Gly Ser Ser Glu Ile Phe Phe Lys Ile Lys
        50                  55                  60
Lys Thr Thr Pro Leu Arg Arg Leu Met Glu Ala Phe Ala Lys Arg Gln
65                  70                  75                  80
Gly Lys Glu Met Asp Ser Leu Arg Phe Leu Tyr Asp Gly Ile Arg Ile
                85                  90                  95
Gln Ala Asp Gln Thr Pro Glu Asp Leu Asp Met Glu Asp Asn Asp Ile
            100                 105                 110
Ile Glu Ala His Arg Glu Gln Ile Gly Gly Gly Ser Val Ala His Gly
        115                 120                 125
Leu Ala Trp Ser Tyr Tyr Ile Gly Tyr Leu Arg Leu Ile Leu Pro Glu
    130                 135                 140
Leu Gln Ala Arg Ile Arg Thr Tyr Asn Gln His Tyr Asn Asn Leu Leu
145                 150                 155                 160
Arg Gly Ala Val Ser Gln Arg Leu Tyr Ile Leu Leu Pro Leu Asp Cys
                165                 170                 175
Gly Val Pro Asp Asn Leu Ser Met Ala Asp Pro Asn Ile Arg Phe Leu
            180                 185                 190
Asp Lys Leu Pro Gln Gln Thr Gly Asp Arg Ala Gly Ile Lys Asp Arg
        195                 200                 205
Val Tyr Ser Asn Ser Ile Tyr Glu Leu Leu Glu Asn Gly Gln Arg Ala
    210                 215                 220
Gly Thr Cys Val Leu Glu Tyr Ala Thr Pro Leu Gln Thr Leu Phe Ala
225                 230                 235                 240
Met Ser Gln Tyr Ser Gln Ala Gly Phe Ser Arg Glu Asp Arg Leu Glu
                245                 250                 255
```

```
Gln Ala Lys Leu Phe Cys Arg Thr Leu Glu Asp Ile Leu Ala Asp Ala
                260                 265                 270

Pro Glu Ser Gln Asn Asn Cys Arg Leu Ile Ala Tyr Gln Glu Pro Ala
            275                 280                 285

Asp Asp Ser Ser Phe Ser Leu Ser Gln Glu Val Leu Arg His Leu Arg
        290                 295                 300

Gln Glu Glu Lys Glu Glu Val
305                 310

<210> SEQ ID NO 6
<211> LENGTH: 187
<212> TYPE: PRT
<213> ORGANISM: Homo sapiens

<400> SEQUENCE: 6

Val Ala His Gly Leu Ala Trp Ser Tyr Tyr Ile Gly Tyr Leu Arg Leu
1               5                   10                  15

Ile Leu Pro Glu Leu Gln Ala Arg Ile Arg Thr Tyr Asn Gln His Tyr
            20                  25                  30

Asn Asn Leu Leu Arg Gly Ala Val Ser Gln Arg Leu Tyr Ile Leu Leu
        35                  40                  45

Pro Leu Asp Cys Gly Val Pro Asp Asn Leu Ser Met Ala Asp Pro Asn
    50                  55                  60

Ile Arg Phe Leu Asp Lys Leu Pro Gln Gln Thr Gly Asp His Ala Gly
65                  70                  75                  80

Ile Lys Asp Arg Val Tyr Ser Asn Ser Ile Tyr Glu Leu Leu Glu Asn
                85                  90                  95

Gly Gln Arg Ala Gly Thr Cys Val Leu Glu Tyr Ala Thr Pro Leu Gln
            100                 105                 110

Thr Leu Phe Ala Met Ser Gln Tyr Ser Gln Ala Gly Phe Ser Arg Glu
        115                 120                 125

Asp Arg Leu Glu Gln Ala Lys Leu Phe Cys Arg Thr Leu Glu Asp Ile
    130                 135                 140

Leu Ala Asp Ala Pro Glu Ser Gln Asn Asn Cys Arg Leu Ile Ala Tyr
145                 150                 155                 160

Gln Glu Pro Ala Asp Asp Ser Ser Phe Ser Leu Ser Gln Glu Val Leu
                165                 170                 175

Arg His Leu Arg Gln Glu Glu Lys Glu Glu Val
            180                 185

<210> SEQ ID NO 7
<211> LENGTH: 311
<212> TYPE: PRT
<213> ORGANISM: Artificial Sequence
<220> FEATURE:
<223> OTHER INFORMATION: His-TEV-Sumo-REF STING 155-341 construct

<400> SEQUENCE: 7

Met His His His His His Ser Ser Gly Val Asp Leu Gly Thr Glu
1               5                   10                  15

Asn Leu Tyr Phe Gln Ser Asn Ala Met Ser Asp Ser Glu Val Asn Gln
            20                  25                  30

Glu Ala Lys Pro Glu Val Lys Pro Glu Val Lys Pro Thr His Ile
            35                  40                  45

Asn Leu Lys Val Ser Asp Gly Ser Ser Glu Ile Phe Phe Lys Ile Lys
        50                  55                  60

Lys Thr Thr Pro Leu Arg Arg Leu Met Glu Ala Phe Ala Lys Arg Gln
```

```
65                  70                  75                  80
Gly Lys Glu Met Asp Ser Leu Arg Phe Leu Tyr Asp Gly Ile Arg Ile
                85                  90                  95

Gln Ala Asp Gln Thr Pro Glu Asp Leu Asp Met Glu Asp Asn Asp Ile
                100                 105                 110

Ile Glu Ala His Arg Glu Gln Ile Gly Gly Gly Ser Val Ala His Gly
                115                 120                 125

Leu Ala Trp Ser Tyr Tyr Ile Gly Tyr Leu Arg Leu Ile Leu Pro Glu
            130                 135                 140

Leu Gln Ala Arg Ile Arg Thr Tyr Asn Gln His Tyr Asn Asn Leu Leu
145                 150                 155                 160

Arg Gly Ala Val Ser Gln Arg Leu Tyr Ile Leu Leu Pro Leu Asp Cys
                165                 170                 175

Gly Val Pro Asp Asn Leu Ser Met Ala Asp Pro Asn Ile Arg Phe Leu
                180                 185                 190

Asp Lys Leu Pro Gln Gln Thr Gly Asp His Ala Gly Ile Lys Asp Arg
                195                 200                 205

Val Tyr Ser Asn Ser Ile Tyr Glu Leu Leu Glu Asn Gly Gln Arg Ala
            210                 215                 220

Gly Thr Cys Val Leu Glu Tyr Ala Thr Pro Leu Gln Thr Leu Phe Ala
225                 230                 235                 240

Met Ser Gln Tyr Ser Gln Ala Gly Phe Ser Arg Glu Asp Arg Leu Glu
                245                 250                 255

Gln Ala Lys Leu Phe Cys Arg Thr Leu Glu Asp Ile Leu Ala Asp Ala
                260                 265                 270

Pro Glu Ser Gln Asn Asn Cys Arg Leu Ile Ala Tyr Gln Glu Pro Ala
            275                 280                 285

Asp Asp Ser Ser Phe Ser Leu Ser Gln Glu Val Leu Arg His Leu Arg
            290                 295                 300

Gln Glu Glu Lys Glu Glu Val
305                 310
```

METHODS FOR THE TREATMENT OF BLADDER CANCER

CROSS-REFERENCE TO RELATED APPLICATIONS

Not applicable.

BACKGROUND

STING (stimulator of interferon genes) is a signaling molecule in the innate response to dsDNA in the cytosol. STING deletion has been reported in multiple human cancers. In addition, deregulation of STING signaling in human cancers also has been reported in melanoma (Xia T, et al., "Recurrent Loss of STING Signaling in Melanoma Correlates with Susceptibility to Viral Oncolysis" *Cancer Res.* 2016) and colon cancer. (Xia T, et al., "Deregulation of STING Signaling in Colorectal Carcinoma Constrains DNA Damage Responses and Correlates With Tumorigenesis" Cell Rep. 2016; 14:282-97). Interestingly, in those studies, genomic analysis results showed loss expression of STING is not due to gene deletion or mutation, but through epigenetic changes. (Xia, *Cancer Res.* 2016; Xia, *Cell Rep.* 2016). STING's cancer protection activity is also supported by evidence obtained from mouse model studies. STING knockout mice have shown defective tumor control. (Woo S R, et al. "STING-dependent cytosolic DNA sensing mediates innate immune recognition of immunogenic tumors" *Immunity* 2014; 41:830-42).

In addition, STING's role in protecting ontogenesis has been demonstrated in several mouse spontaneous models, including glioma (Ohkuri T, et al., "Protective role of STING against gliomagenesis: Rational use of STING agonist in anti-glioma immunotherapy" *Oncoimmunology.* 2015; 4: e999523), and colon cancer (Zhu Q, et al., "Cutting edge: STING mediates protection against colorectal tumorigenesis by governing the magnitude of intestinal inflammation". *J. Immunol.* 2014; 193:4779-82). This anti-tumor effect may be due to its ability to counter over-activation of NF-kB and STAT3. (Okihuri 2015). Activation of STING pathway also showed potent activity in preclinical mouse tumor models. (Woo 2014; Chandra D, et al. "STING ligand c-di-GMP improves cancer vaccination against metastatic breast cancer" *Cancer Immunol Res.* 2014,2.901-10; Corrales L, et al., "Direct Activation of STING in the Tumor Microenvironment Leads to Potent and Systemic Tumor Regression and Immunity" *Cell Rep.* 2015; 11:1018-30; Curran E, et al "STING Pathway Activation Stimulates Potent Immunity against Acute Myeloid Leukemia" *Cell Rep.* 2016; 15:2357-66; Tang C H, et al. "Agonist-Mediated Activation of STING Induces Apoptosis in Malignant B Cells" *Cancer Res.* 2016; 76:2137-52). This anti-tumor activity is likely due to disruption of tumor vasculature and followed by induction of adaptive immune response. (Corrales L, et al., "The host STING pathway at the interface of cancer and immunity" *J. Clin. Invest.* 2016; 126:2404-11). Accordingly, direct or intratumoral stimulation of STING in a tumor microenvironment by an agonist may represent a novel approach for treating cancer.

Furthermore, bladder cancer is the fourth and eleventh most common cancer in men and women, respectively, with unique drug administration route for early stage cancer patients (Kamat et al., "What is new in non-muscle-invasive bladder cancer in 2016?" *Turk J Urol* 2017; 43 (1): 9-13). In 2018, approximately 81,190 new cases of bladder cancer were estimated in the United States, and about 17,240 deaths from bladder cancer are expected (American Cancer Society website). Administration of BCG (*Bacillus* Calmette-Gueri) is the front line treatment option for high risk non-muscle invasive bladder cancer (NMIBC). Unfortunately, up to 40% of patients will be unresponsive to BCG treatment and many of these patients have to undergo radical cystectomy procedure to remove the entire bladder (Zlotta, A. R., et al., "The management of BCG failure in non-muscle-invasive bladder cancer: an update," *Can Urol Assoc J* 2009; 3 (Suppl4): S199-205) leaving patients with a poorer life quality after the surgery. Hence, there is a significant unmet medical need for effective alternate bladder cancer therapies to avoid or delay the radical cystectomy.

BRIEF SUMMARY

Embodiments may provide a method of treating bladder cancer in a patient in need of treatment, comprising administering to the patient Compound 1 or a pharmaceutically acceptable salt thereof:

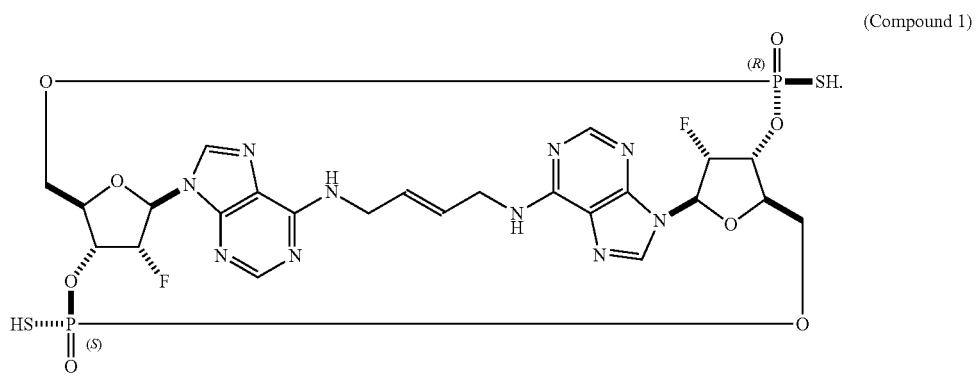

(Compound 1)

In some embodiments the pharmaceutically acceptable salt administered according to embodiments as reported herein is a diammonium salt or a triethyl amine (TEA) salt. Further embodiments may provide treatment of bladder cancer by administering to a patient in need of treatment for bladder cancer a pharmaceutical composition including Compound 1 or pharmaceutically acceptable salt thereof and a pharmaceutically acceptable excipient.

Further embodiments may provide a method of treating bladder cancer in a patient in need of treatment, comprising administering to the patient Compound 2 or a pharmaceutically acceptable salt thereof:

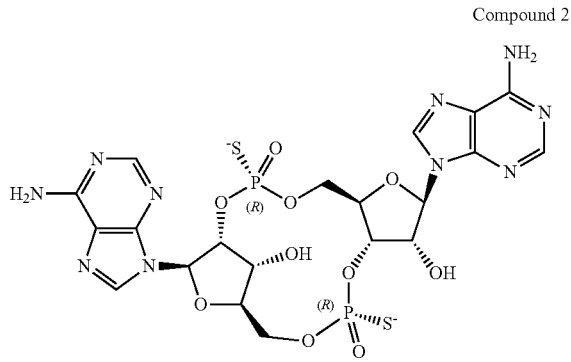

Compound 2

Further embodiments may provide use of Compound 1, Compound 2, or a pharmaceutically acceptable salt thereof as reported herein for preparation of a pharmaceutical composition for treating bladder cancer.

Embodiments may provide use of Compound 1, Compound 2, a pharmaceutically acceptable salt thereof, or pharmaceutical composition including Compound 1, Compound 2, or a pharmaceutically acceptable salt thereof, in a treatment for bladder cancer.

Embodiments may provide a method of treating bladder cancer comprising identifying an individual having a bladder cancer treatable by Compound 1, Compound 2, a pharmaceutically acceptable salt thereof, or a pharmaceutical composition including Compound 1, Compound 2, or a pharmaceutically acceptable salt thereof; and administering to said individual a therapeutically effective amount of Compound 1, Compound 2, a pharmaceutically acceptable salt or pharmaceutical composition by which the bladder cancer has been identified as treatable.

In some embodiments the individual is identified as having a bladder cancer treatable by Compound 1, Compound 2, a pharmaceutically acceptable salt thereof, or a pharmaceutical composition including Compound 1, Compound 2, or, a pharmaceutically acceptable salt thereof, by a presence of a REF STING variant allele in the patient.

Some embodiments provide a method of treating bladder cancer in a patient having REF STING allele comprising administering to said patient Compound 1, Compound 2, a pharmaceutically acceptable salt thereof, or a pharmaceutical composition including Compound 1, Compound 2, or a pharmaceutically acceptable salt thereof.

Some embodiments provide a method of treating cancer in a patient having WT STING allele comprising administering to said patient a Compound 1, Compound 2, a pharmaceutically acceptable salt thereof, or a pharmaceutical composition including Compound 1 or a pharmaceutically acceptable salt thereof.

Some embodiments provide a method of treating cancer in a patient having AQ STING allele comprising administering to said patient Compound 1, Compound 2, a pharmaceutically acceptable salt of Compound 1, Compound 2, or a pharmaceutical composition including Compound 1, Compound 2, or a pharmaceutically acceptable salt thereof.

Some embodiments provide a method of treating cancer in a patient having HAQ STING allele comprising administering to said patient Compound 1, Compound 2, a pharmaceutically acceptable salt of Compound 1, Compound 2, or a pharmaceutical composition including Compound 1, Compound 2, or a pharmaceutically acceptable salt thereof.

In some embodiments, Compound 1 is provided as a free acid. In some embodiments, the compound is provided as an $NH_4$ salt or as a triethyl amine (TEA) salt.

Embodiments may provide a method of treating bladder cancer in a patient in need thereof, including administering to the patient a therapeutically effective amount of Compound 1 or a pharmaceutically acceptable salt thereof, as recited above.

Embodiments may provide a method of treating bladder cancer in a patient comprising administering to said patient Compound 1, Compound 2, or pharmaceutically acceptable salt thereof, or a pharmaceutical composition, as reported herein. Bladder cancers treated as reported herein may be urothelial carcinoma.

DETAILED DESCRIPTION OF EMBODIMENTS

Figure 1:
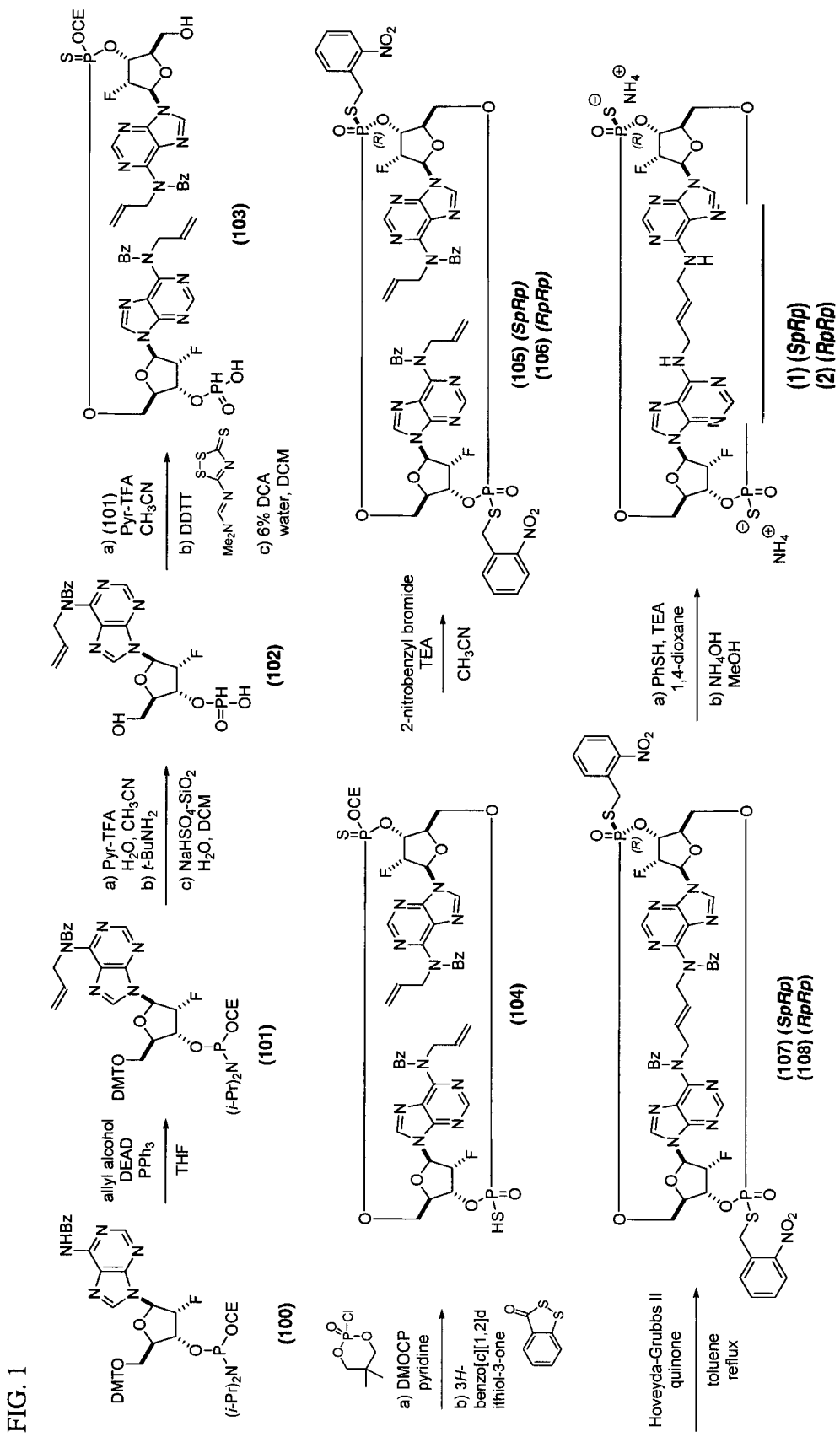
FIG. 1 shows a synthesis of Compound 1a. This synthesis is also reported in U.S. patent application Ser. No. 15/898,533, filed on Feb. 17, 2018, and incorporated by reference herein.

Provided herein is a compound (Compound 1) and pharmaceutically acceptable salts thereof, as well as pharmaceutical compositions that may be useful in treating bladder cancer. Compound 2 or a pharmaceutically acceptable salt thereof, as well as pharmaceutical compositions including Compound 2 or a pharmaceutically acceptable salt thereof, may also be useful in treating bladder cancer. The compounds may activate stimulator of interferon genes (STING).

This is Compound 1:

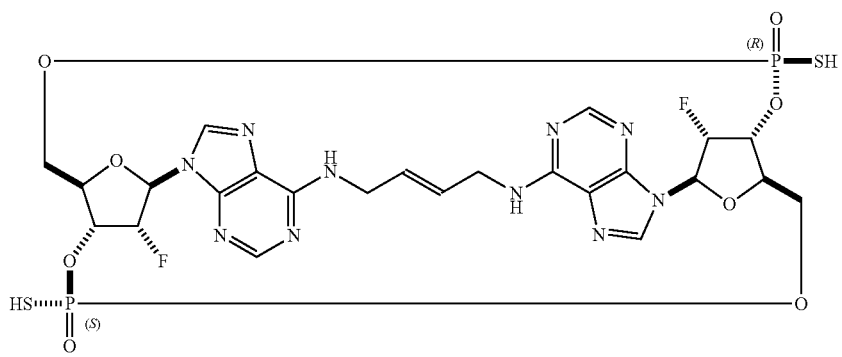

This is Compound 2:

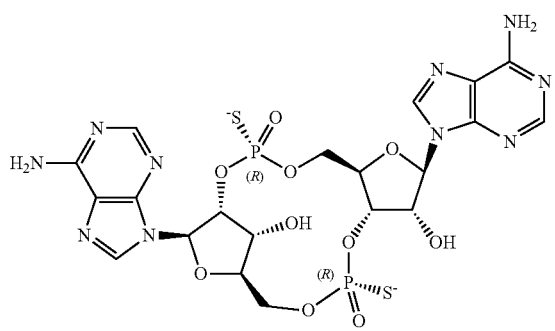

In some embodiments, Compound 1 is provided as a free acid. In some embodiments, the compound is provided as, for example, an NH₄ salt. Reference to "Compound 1a" will indicate a diammonium salt of Compound 1.

Embodiments may provide a method of treating bladder cancer in a patient in need thereof, including administering to the patient a therapeutically effective amount of Compound 1, Compound 2, or pharmaceutically acceptable salt thereof.

Pharmaceutical compositions for treating bladder cancer may also be provided including a compound reported herein or a pharmaceutically acceptable salt thereof, as well as a pharmaceutically acceptable excipient. Embodiments as reported herein may be used to treat bladder cancer or to prepare medicaments useful for treatment of bladder cancer.

Those of skill in the art will recognize that where substituents bound to the phosphorous atoms ($P_1, P_2$) have both single and double bonds, they may be susceptible to tautomerization. For example, the compounds may tautomerize at equilibrium. One example is shown below:

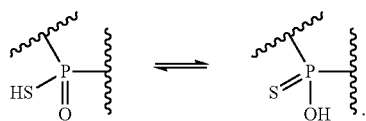 [SMILES: *P(*)(=O)S ; *P(*)(O)=S]

Such tautomers should be considered to be within the scope of the claims. A structural representation of either tautomer for a given compound will represent the same compound Methods of Treatment Embodiments may provide a method of treating bladder cancer in a patient in need thereof, including administering to the patient a therapeutically effective amount of a Compound 1 or a pharmaceutically acceptable salt thereof.

In some embodiments, Compound 1 is provided as a free acid or a pharmaceutically acceptable salt thereof. In some embodiments, the administered compound is provided as an NH₄ salt, a free acid, or a pharmaceutically acceptable salt thereof. In some embodiments, the compound is provided as an NH₄ salt.

Some embodiments provide a method of treating bladder cancer comprising administering to a patient in need of treatment a therapeutically effective amount of a STING agonist. In such embodiments the administration may be, but is not required to be, intravesicular administration. Examples of potential STING agonist that may be used in the treatment of bladder cancer, and which may be, but are not required to be, administered intravesicularlly, include but are not limited to those identified in U.S. patent application Ser. No. 15/898,533, filed on Feb. 17, 2018; PCT App. No. PCT/US2018/018556, filed on Feb. 17, 2018; PCT App. No. PCT/US2018/018561, filed on Feb. 17, 2018; US 2014/0205653 A1; US 2014/0329889 A1; US 2014/0341976 A1; US 2007/0149462 A1; WO 2018/098203 A1; WO 2018/198076 A1; WO 2018/198084 A1; WO 2018/140831 A2; US 2014/0341976 A1; WO 2015/185565 A1; U.S. Pat. No. 7,709,458 B2; U.S. Pat. Nos. 7,592,326; 7,569,555 B2; US 2014/0205653 A1; US 2014/0341976 A1; U.S. 2015/0056224 A1; US 2016/0362441 A1; US 2017/0158724 A1; US 2017/044206 A1; U.S. Pat. Nos. 5,547,941; 7,569,555 B2; 7,592,326 B2; 7,709,458 B2; 9,549,944 B2; WO 2009/133560 A1; WO 2015/074145 A1; WO 2015/077354 A1; WO 2015/185565 A1; WO 2016/100261 A1; WO 2016/120305 A1; WO 2016/145102 A1; WO 2017/027645 A1; WO 2017/027646 A1; WO 2017/075477 A1; WO 2019/043634 A2; WO 2019/046496 A1; WO 2019/046498 A1; WO 2019/046500 A1; WO 2019/046511 A1; WO 2017/093933 A1; WO 2017/123657 A1; WO 2017/175156 A1; EP 1740, 192 B1; CN 102199183 A; Fu, J., et al., "STING Agonist Formulated Cancer Vaccines Can Cure Established Tumors Resistant to PD-1 Blockade," Sci. Translational Med., 7 (283): 283ra52, (Apr. 15, 2015); Corrales, L. et al., "Direct Activation of STING in the Tumor Microenvironment Leads to Potent and Systemic Tumor Regression and Immunity," Cell Reports, 11:1018-1030 (2015); and Lioux, T. et al., "Design, Synthesis, and Biological Evaluation of Novel Cyclic Adenosine-Inosine Monophosphate (cAIMP) Analogs That Activate Stimulator of Interferon Genes (STING)," J. Med. Chem., 59:10253-10267 (2016). All of those documents, including the compounds therein, are incorporated by reference herein, if any component of any of those documents contradicts or is otherwise inconsistent with anything in this specification, then this specification controls.

Dosages

The optimal dose for treatment of bladder cancer can be determined empirically for each individual using known methods and will depend upon a variety of factors, including the activity of the agents; the age, body weight, general health, gender and diet of the individual; the time and route of administration; and other medications the individual is taking. Optimal dosages may be established using routine testing and procedures that are well known in the art. Administration of the above compounds may be by any suitable route.

"Pharmaceutically acceptable salt" as used herein refers to acid addition salts or base addition salts of the compounds in the present disclosure. A pharmaceutically acceptable salt is any salt which retains the activity of the parent compound and does not impart any unduly deleterious or undesirable effect on a subject to whom it is administered and in the context in which it is administered. Pharmaceutically acceptable salts include, but are not limited to, metal complexes and salts of both inorganic and carboxylic acids. Pharmaceutically acceptable salts also include metal salts such as aluminum, calcium, iron, magnesium, manganese and complex salts. In addition, pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycolic, glycolylarsanilic, hexamic, hexylresorcinoic, hydrabamic, hydrobromic, hydrochloric, hydrochloride, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like. Sodium salts and potassium salts may also be prepared.

Embodiments may be diammonium salts. Pharmaceutically acceptable salts may be derived from amino acids including, but not limited to, cysteine. Methods for producing compounds as salts are known to those of skill in the art (see, e.g., Stahl et al., Handbook of Pharmaceutical Salts: Properties, Selection, and Use, Wiley-VCH; Verlag Helvetica Chimica Acta, Zurich, 2002, Berge et al., J. Pharm. Sci. 66:1, 1977).

An "effective amount" or "therapeutically effective amount" of a therapeutic agent is an amount sufficient to provide an observable therapeutic benefit compared to bladder cancer left untreated in a subject or patient.

Active agents as reported herein can be combined with a pharmaceutically acceptable carrier to provide pharmaceutical formulations thereof. The particular choice of carrier and formulation will depend upon the particular route of administration for which the composition is intended.

"Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, sorbic acid, potassium sorbate, partial glyceride mixtures of saturated vegetable fatty acids, water, salts or electrolytes, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene glycol and wool fat.

The compositions of the present invention may be suitable for parenteral, oral, inhalation spray, topical, rectal, nasal, buccal, intravesicular, vaginal or implanted reservoir administration, etc. In some embodiments, the formulation comprises ingredients that are from natural or non-natural sources. In some embodiments, the formulation or carrier may be provided in a sterile form. Non-limiting examples of a sterile carrier include endotoxin-free water or pyrogen-free water. Compositions may be administered through intravesicular administration.

The term "parenteral" as used herein includes subcutaneous, intravenous, intramuscular, intra-articular, intra-synovial, intrasternal, intrathecal, intrahepatic, intralesional and intracranial injection or infusion techniques. In particular embodiments, the compounds are administered intravenously, orally, subcutaneously, or via intramuscular administration. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. In some embodiments compositions are administered intravesicularlly.

For this purpose, any bland fixed oil may be employed including synthetic mono- or di-glycerides. Fatty acids and their glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents that are commonly used in the manufacture of pharmaceutically acceptable solid, liquid, or other dosage forms may also be used for the purposes of formulation.

For oral administration, a compound or salt may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient may be combined with emulsifying and suspending agents. If desired, certain sweetening, flavoring or coloring agents may also be added. In addition preservatives may also be added. Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

"Immediate-release" is meant to include a conventional release, in which release of the drug starts immediately after administration. As used herein, the term "immediate release" includes dosage forms that allow the drug to dissolve in the gastrointestinal contents, with no intention of delaying or prolonging the dissolution or absorption of the drug. The objective is for the drug to be released rapidly after administration, for example for it to be possible to release at least 80% of the drug within approximately 30 minutes after commencement of dissolution in a dissolution test.

"Sustained-release" or "extended-release" includes dosage forms whose drug-release characteristics of time course and/or location are chosen to accomplish therapeutic or convenience objectives not offered by conventional dosage forms such as a solution or an immediate release dosage form.

The term "steady-state" means that a plasma level for a given active agent has been achieved and which is maintained with subsequent doses of the active agent at a level which is at or above the minimum effective therapeutic level and is below the minimum toxic plasma level for a given active agent.

The term "dose range" as used herein refers to an upper and a lower limit of an acceptable variation of the amount of agent specified. Typically, a dose of an agent in any amount within the specified range can be administered to patients undergoing treatment.

The term "treat" is used herein to mean to relieve, reduce or alleviate at least one symptom of a disease in a subject. For example, in relation to bladder cancer, the term "treat" may mean to arrest, delay the onset (i.e., the period prior to clinical manifestation of a disease or symptom of a disease) and/or reduce the risk of developing or worsening a symptom of bladder cancer. The term "protect" is used herein to mean prevent delay or treat, or all, as appropriate, development or continuance or aggravation of symptoms of bladder cancer in a subject.

The term "subject" or "patient" is intended to include animals, which are capable of suffering from or afflicted with bladder cancer. Examples of subjects or patients include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from bladder cancer.

The term "about" or "approximately" usually means within 20%, more preferably within 10%, and most preferably still within 5% of a given value or range. Alternatively, especially in biological systems, the term "about" means approximately within a log (i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

Exemplary cell proliferative disorders that may be treated using one or more compounds disclosed herein include, but are not limited to cancer, a precancer or precancerous condition, and metastatic lesions in tissue and organs in the body. Cell proliferative disorders may include hyperplasia, metaplasia, and dysplasia.

A compound disclosed herein, or a pharmaceutically acceptable salt thereof, may be used to treat or prevent a cell proliferative disorder, or to treat or prevent cancer, in a subject having an increased risk of developing cancer relative to the population at large, or used to identify suitable candidates for such purposes.

Pharmaceutical Formulations and Routes of Administration

Provided herein are pharmaceutical formulations comprising Compound 1 or a pharmaceutically acceptable salt thereof for the treatment of bladder cancer. The pharmaceutical formulations may additionally comprise a carrier or excipient, stabilizer, flavoring agent, and/or coloring agent.

Compound 1 or a pharmaceutically acceptable salt thereof may be administered using a variety of routes of administration known to those skilled in the art. Routes of administration include oral administration and intravesicular administration. In certain embodiments, a pharmaceutical formulation comprising the compound or pharmaceutically acceptable salt thereof may be taken orally in the form of liquid, syrup, tablet, capsule, powder, sprinkle, chewtab, or dissolvable disk. Alternatively, pharmaceutical formulations of the present invention can be administered intravenously or transdermally. Additional routes of administration are known to those skilled in the art (see, e.g., Remington's Pharmaceutical Sciences, Gennaro A. R., Ed., 20.sup.th Edition, Mack Publishing Co., Easton, Pa.).

In some embodiments, the compound or pharmaceutically acceptable salt is formulated as a paste, jelly, or suspension. For example, the drug is dissolved, entrapped or suspended in the form of drug particles, microencapsulated particles, or drug-polymer particles in a gelatinous solution or semi-solid. An advantage of an oral jelly formulation is that it is easier to administer the drug to patients who have difficulty swallowing tablets, capsules or pills. In certain embodiments, the compound is thoroughly mixed and suspended in an appropriate medium to form a paste or a gel. Additional agents can optionally be mixed to provide flavor during oral administration. Peanut butter or alginate, flavored with raspberry and a sweetener are examples of the many suitable taste masking agents. In various embodiments, the paste or jelly can also be formulated with suitable binders or excipients known in the art for topical administration.

Methods of preparing sustained release formulations in the form of tablets, capsules or pills are known in the art. In some embodiments, the sustained release formulation is prepared by coating the active ingredient of the drug with a polymer, preferably a water-insoluble polymer. For example, a water-insoluble polymer used in the pharmaceutical field as a sustained release coating agent, an enteric coating agent, or a gastric coating agent. The water-insoluble polymer can include, for example, ethyl cellulose, purified shellac, white shellac, aminoalkyl methacrylate copolymer RS, hydroxypropyl methylcellulose phthalate, hydroxypropyl methylcellulose acetate succinate, carboxymethylethylcellulose, cellulose acetate phthalate, methacrylic acid copolymer L, methacrylic acid copolymer LD, methacrylic acid copolymer S, aminoalkyl methacrylate copolymer E, or polyvinyl acetal diethylaminoacetate.

The type, degree of substitution and molecular weight of the water-insoluble polymers can depend on solubility of the active ingredient in water or an alcohol, the desired sustained release level and the like. The water-insoluble polymers can be used either alone or in combination. There can be further incorporated a hydrogenated oil, stearic acid, or cetanol as a coating auxiliary agent, and a middle-chain triglyceride, triacetin, triethyl citrate, or cetanol as a plasticizer.

In some embodiments, the sustained release formulation is a matrix-type tablet or granule. The active ingredient can be coated with up to 3 different types of polymers. These three different types of polymers can include: 1) a water insoluble polymer, such as ethylcellulose; 2) a pH independent gelling polymer, such as hydroxypropyl methylcellulose; and 3) a pH dependent gelling polymer, such as sodium alginate. These three different types of polymers can be used together to attenuate the release rate of the drugs.

Dosage Forms: Release Properties

Sustained-release formulations can achieve a degree of sustained effect. However, the exposure and/or the bioavailability of the active ingredient may vary based on a variety of factors, such as for example, the absorption window, the carriers or excipients used in the formulation, the mode of delivery of the formulation, and/or the transit time of the active ingredient through the gastrointestinal tract of the patient.

A therapy can contain at least one sustained-release portion for performing a sustained-release function and one immediate release portion for performing an immediate release function. In certain embodiments, when the therapy is in a single dosage form, it can be in the form of tablets formed from a mixture of sustained-release granules constituting a sustained-release portion and immediate-release granules constituting an immediate-release portion, a capsule preparation obtained by filling a capsule with sustained-release granules and immediate-release granules, or press-coated tablets in which an outer layer constituting an immediate-release portion is formed on an inner core constituting a sustained-release portion. There is, however, no limitation to the above embodiments.

Moreover, there are no particular limitations on the state of containment of the drug in the composition or in an immediate-release portion or a sustained-release portion; the compound may be dispersed uniformly in the composition, immediate release portion or sustained release portion, or may be contained in only one part of the composition, immediate-release portion or sustained-release portion, or may be contained such that there is a concentration gradient.

A sustained-release portion in the composition according to the present invention can contain at least one non-pH-dependent polymeric substance or pH-dependent polymeric substance for controlling drug release.

A non-pH-dependent polymeric substance used herein can comprise a polymeric substance whose charge state hardly changes under pH conditions generally found in the gastrointestinal tract, specifically from pH 1 to pH 8. This means, for example, a polymeric substance that does not have functional groups whose charge state changes depending on the pH such as basic functional groups such as amino groups or acidic functional groups such as carboxylic acid groups. Note that the non-pH-dependent polymeric substance can be included for giving the composition according to the present invention a sustained-release function, but may also be included for another purpose. Moreover, the non-pH-dependent polymeric substance used in the present invention may be water-insoluble, or may swell in water or dissolve in water to form a gel.

Examples of water-insoluble non-pH-dependent polymeric substances include, but are not limited to, cellulose ethers, cellulose esters, and methacrylic acid-acrylic acid copolymers (trade name Eudragit, manufactured by Rohm GmbH & Co. KG, Darmstadt, Germany). Examples include, but are not limited to, cellulose alkyl ethers such as ethylcellulose (trade name Ethocel, manufactured by Dow Chemical Company, USA), ethyl methylcellulose, ethyl propylcellulose or isopropylcellulose, and butylcellulose, cellulose aralkyl ethers such as benzyl cellulose, cellulose cyanoalkyl ethers such as cyanoethylcellulose, cellulose organic acid esters such as cellulose acetate butyrate, cellulose acetate, cellulose propionate or cellulose butyrate, and cellulose acetate propionate, ethyl acrylate-methyl methacrylate copolymers (trade name Eudragit NE, manufactured by Rohm GmbH & Co. KG, Darmstadt, Germany), and aminoalkyl methacrylate copolymer RS (trade names Eudragit RL, Eudragit RS). There are no particular limitations on the mean particle diameter of a water-insoluble polymer used in the present invention, but usually the lower this mean particle diameter the better the performance, with the mean particle diameter preferably being from 0.1 to 100 μm, more preferably from 1 to 50 μm, particularly preferably from 3 to 15 μm, most preferably from 5 to 15 μm. Moreover, examples of water-soluble or water-swelling non-pH-dependent polymeric substances include, but are not limited to, polyethylene oxide (trade name Polyox, manufactured by Dow Chemical Company, molecular weight 100,000 to 7,000,000), low-substituted hydroxypropyl cellulose (trade name L-HPC, manufactured by Shin-Etsu Chemical, Japan), hydroxypropyl cellulose (trade name HPC, manufactured by Nippon Soda, Co., Ltd, Japan), hydroxypropyl methylcellulose (trade names Metolose 60SH, 65SH, 90SH, manufactured by Shin-Etsu Chemical, Japan), and methylcellulose (trade name Metolose SM, manufactured by Shin-Etsu Chemical, Japan).

In some embodiments a single non-pH-dependent polymeric substance may be contained in the composition, or a plurality of the non-pH-dependent polymeric substances may be contained. The non-pH-dependent polymeric substance, if used in embodiments reported herein, may be a water-insoluble polymeric substance, more preferably ethylcellulose, an ethyl acrylate-methyl methacrylate copolymer (trade name Eudragit NE), or an aminoalkyl methacrylate copolymer RS (trade name Eudragit RL, Eudragit RS). Particularly preferable is at least one of ethylcellulose and an aminoalkyl methacrylate copolymer RS. Most preferable is ethylcellulose. There are no particular limitations on the amount of the non-pH-dependent polymeric substance contained in the composition; this amount can be adjusted as appropriate in accordance with the purpose such as controlling sustained drug release.

A pH-dependent polymeric substance that can be used in embodiments reported herein may be a polymeric substance whose charge state changes under pH conditions generally found in the gastrointestinal tract, specifically from pH 1 to pH 8. This means, for example, a polymeric substance having functional groups whose charge state changes depending on the pH such as basic functional groups such as amino groups or acidic functional groups such as carboxylic acid groups. The pH-dependent functional groups of the pH-dependent polymeric substance are preferably acidic functional groups, with the pH-dependent polymeric substance most preferably having carboxylic acid groups.

A pH-dependent polymeric substance used in the present invention may be water-insoluble, or may swell in water or dissolve in water to form a gel. Examples of pH-dependent polymeric substances used in the present invention include, but are not limited to, enteric polymeric substances. Examples of enteric polymeric substances include, but are not limited to, methacrylic acid-methyl methacrylate copolymers (Eudragit L100, Eudragit S100, manufactured by Rohm GmbH & Co. KG, Darmstadt, Germany), methacrylic acid-ethyl acrylate copolymers (Eudragit L100-55, Eudragit L30D-55, manufactured by Rohm GmbH & Co. KG, Darmstadt, Germany), hydroxypropyl methylcellulose phthalate (HP-55, HP-50, manufactured by Shin-Etsu Chemical, Japan), hydroxypropyl methylcellulose acetate succinate (AQOAT, manufactured by Shin-Etsu Chemical, Japan), carboxymethyl ethylcellulose (CMEC, manufactured by Freund Corporation, Japan), and cellulose acetate phthalate.

Examples of pH-dependent polymeric substances that swell in water or dissolve in water to form a gel include, but are not limited to, alginic acid, pectin, carboxyvinyl polymer, and carboxymethyl cellulose. In the present invention, a single pH-dependent polymeric substance may be contained in the composition, or a plurality of pH-dependent polymeric substances may be contained. The pH-dependent polymeric substance used in the present invention is preferably an enteric polymeric substance, more preferably a methacrylic acid-ethyl acrylate copolymer, a methacrylic acid-methyl methacrylate copolymer, hydroxypropyl methylcellulose phthalate, or hydroxypropyl methylcellulose acetate succinate, particularly preferably a methacrylic acid-ethyl acrylate copolymer.

When using a pH-dependent polymeric substance in the manufacturing process of a composition according to the present invention, a commercially available product of a powder type or a granular type, or a suspension type in which the pH-dependent polymeric substance has been dispersed in a solvent in advance can be used as is, or such a commercially available product can be used dispersed in water or an organic solvent. The lower the particle diameter of the pH-dependent polymeric substance the better the performance, with the pH-dependent polymeric substance preferably being of the powder type. In the case of a methacrylic acid-ethyl acrylate copolymer, an example is Eudragit L100-55. There are no particular limitations on the mean particle diameter of a pH-dependent polymeric substance used in the present invention, but the mean particle diameter is preferably from 0.05 to 100 µm, more preferably from 0.05 to 70 µm, most preferably from 0.05 to 50 µm. Moreover, there are no particular limitations on the amount of the pH-dependent polymeric substance, for example, in the case of an enteric polymeric substance, the amount is generally from 0.1 to 90 parts by weight, preferably from 1 to 70 parts by weight, more preferably from 5 to 60 parts by weight, particularly preferably from 10 to 50 parts by weight, based on 100 parts by weight of the composition.

A therapy according to embodiments reported herein may further contain any of various additives, such as any of various pharmacologically acceptable carriers such as diluents, lubricants, binders and disintegrants, as well as preservatives, colorants, sweeteners, plasticizers, film coating agents and so on, as necessary. Examples of diluents include, but are not limited to, lactose, mannitol, dibasic calcium phosphate, starch, pregelatinized starch, crystalline cellulose, light silicic anhydride, synthetic aluminum silicate, magnesium aluminate metasilicate or the like. Examples of lubricants include, but are not limited to, magnesium stearate, calcium stearate, talc, sodium stearyl fumarate or the like. Examples of binders include, but are not limited to, hydroxypropyl cellulose, methylcellulose, sodium carboxymethyl cellulose, hydroxypropyl methylcellulose, polyvinylpyrrolidone or the like. Examples of disintegrants include, but are not limited to, carboxymethyl cellulose, calcium carboxymethyl cellulose, croscarmellose sodium, sodium carboxymethyl starch, low-substituted hydroxypropyl cellulose or the like.

Examples of preservatives include, but are not limited to, paraoxybenzoic acid esters, chlorobutanol, benzyl alcohol, phenethyl alcohol, dehydroacetic acid, sorbic acid or the like. Preferable examples of colorants include, but are not limited to, water-insoluble lake pigments, natural pigments (e.g., .beta.-carotene, chlorophyll, red ferric oxide), yellow ferric oxide, red ferric oxide, black ferric oxide or the like. Preferable examples of sweeteners include, but are not limited to, sodium saccharin, dipotassium glycyrrhizate, aspartame, *stevia* or the like. Examples of plasticizers include, but are not limited to, glycerol fatty acid esters, triethyl citrate, propylene glycol, polyethylene glycol or the like. Examples of film coating agents include, but are not limited to, hydroxypropyl methylcellulose, hydroxypropyl cellulose or the like.

Manufacturing Methods

To manufacture embodiments as reported herein, a single conventional method, or a combination of conventional methods, can be used. For example, when manufacturing drug-containing granules as a sustained-release portion or an immediate-release portion, granulation is the main operation, but this may be combined with other operations such as mixing, drying, sieving, and classification. As the granulation method, for example, a wet granulation method in which a binder and a solvent are added to the powder and granulation is carried out, a dry granulation method in which the powder is compressed and granulation is carried out, a molten granulation method in which a binder that melts on heating is added and heating and granulation are carried out, or the like can be used.

Furthermore, in accordance with the granulation method, an operating method such as a mixing granulation method using a planetary mixer, a screw mixer or the like, a high-speed mixing granulation method using a Henschel mixer, a Super mixer or the like, an extruding granulation method using a cylindrical granulator, a rotary granulator, a screw extruding granulator, a pellet mill type granulator or the like, a wet high-shear granulation method, a fluidized-bed granulation method, a compression granulation method, a crushing granulation method, or a spraying granulation method can be used. After the granulation, drying using a dryer, a fluidized bed or the like, cracking, and sieving can be carried out to obtain the granules or fine granules for use. Moreover, a granulation solvent may be used when preparing the composition according to the present invention. There are no particular limitations on such a granulation solvent, which may be water or any of various organic solvents, for example, water, a lower alcohol such as methanol or ethanol, a ketone such as acetone or methyl ethyl ketone, methylene chloride, or a mixture thereof.

For sustained-release granules contained in embodiments, at least one drug and at least one selected from non-pH-dependent polymeric substances and pH-dependent polymeric substances are mixed together, a diluent and a binder are added as necessary, and granulation is carried out to obtain granular matter. The granular matter obtained is dried using a tray dryer, a fluidized bed dryer or the like, and sieving is carried out using a mill or an oscillator, whereby the sustained-release granules can be obtained. Alternatively, as a method of manufacturing sustained-release granules in the present invention, it is possible to add at least one drug, at least one selected from non-pH-dependent polymeric substances and pH-dependent polymeric substances, and as necessary a diluent and a binder using a dry compactor such as a roller compactor or a slug tabletting machine, and carry out compression-molding while mixing, and then carry out granulation by cracking down to a suitable size. The granular matter prepared using such a granulator may be used as is as granules or fine granules according to the present invention, or may be further cracked using a power mill, a roll granulator, a rotor speed mill or the like, and sieved to obtain sustained-release granules. Note that immediate-release granules can also be manufactured as for the sustained-release granules.

A compression-molded product can be manufactured as a drug-containing sustained-release portion or immediate-release portion, or as a composition reported herein using a single conventional method, or a combination of conventional methods. For example, at least one drug, at least one selected from non-pH-dependent polymeric substances and pH-dependent polymeric substances, a diluent such as mannitol or lactose, a binder such as polyvinylpyrrolidone or crystalline cellulose, a disintegrant such as carmellose sodium or crospovidone, and a lubricant such as magnesium stearate or talc are used, and tabletting is carried out using an ordinary method, whereby the compression-molded product can be obtained. In this case, tabletting is the main operation in the method of manufacturing the compression-molded product, but this may be combined with other operations such as mixing, drying, sugar coating formation, and coating.

Examples of the method for the tabletting include, but are not limited to, direct compression molding in which at least one drug and pharmacologically acceptable additives are mixed together and then the mixture is directly compression-molded into tablets using a tabletting machine, and dry granule compression or wet granule compression in which sustained-release granules or immediate-release granules according to the present invention are subjected to compression-molding after adding a lubricant or a disintegrant as necessary. There are no particular limitations on the tabletting machine used in the compression molding; for example, a single-punch tabletting machine, a rotary tabletting machine, or a press-coated tabletting machine can be used.

Drug-containing sustained-release granules or immediate-release granules, or compression-molded product according to embodiments herein can be used as is in the form of granules or a tablet as the composition, but may also be subjected to further processing to manufacture the composition. For example, the compression-molded product or granules can be given a film coating using a film base material such as ethylcellulose, casein, methylcellulose, hydroxypropyl methylcellulose, methacrylic acid copolymer L, cellulose acetate phthalate, shellac or the like, or given a sugar coating using a sugar coating liquid containing saccharose, sugar alcohol, gum arabic powder, talc or the like, thus producing film-coated tablets or sugar-coated tablets. One solvent in this coating technique may be purified water, but an organic solvent such as an alcohol, a ketone, an ether or a chlorinated hydrocarbon, or a mixture thereof can also be used. For example, ethanol, acetone, methylene chloride or the like can be used as an organic solvent. Moreover, as the coating apparatus, an apparatus ordinarily used in coating techniques for manufacturing medicines can be used, with examples including a spray coating apparatus in which the coating is carried out by spraying a coating liquid or the like, and a rotor fluidized bed granulator for layering.

In the case of manufacturing capsule preparations, capsule preparations can be manufactured by filling sustained-release granules or immediate-release granules as above, or mini-tablets into hard gelatin capsules or HPMC capsules using an automatic capsule filling machine. Alternatively, in the case of the preparations for per-tube administration or a dry syrup that is used mixed with water or the like when taken, sustained-release granules or immediate-release granules as above can be mixed with a thickener or a dispersant so as to disperse these granules, the mixture then being made into granules or tablets. Furthermore, a liquid or jelly can be made using water, and substances selected from dispersants, emulsifiers, thickeners, preservatives, pH adjustors, sweeteners, flavorings, fragrances and so on. However, with respect to other manufacturing methods, there are no limitations to the above.

So that embodiments described herein may be more fully understood, the following examples are set forth. It should be understood that these examples are for illustrative purposes only and are not to be construed as limiting.

EXAMPLES

The following abbreviations may be used throughout the examples.

All: allyl
DMT: 4,4'-Dimethoxytrityl
(DMTO-:

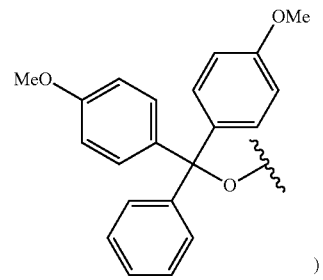 [SMILES: *OC(c1ccccc1)(c1ccc(OC)cc1)c1ccc(OC)cc1]
)

Bz: benzoyl
Hunig's Base: i-Pr$_2$NEt (diisopropylethylamine)
AllylOH: allyl alcohol
OAll: —OCH$_2$CHCH$_2$
ACN: acetonitrile
All: —CH2CHCH2
2-NitroBnBr: 2-nitrobenzyl bromide
Bz: benzoyl
i-Pr: isopropyl
CE: cyanoethyl

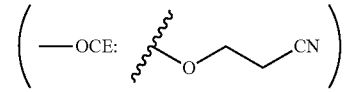

DEAD: diethyl azodicarboxylate
DIAD: diisopropyl azodicarboxylate
DCM: dichloromethane
DDTT: N,N-dimethyl-N'-(3-thioxo-3H-1,2,4-dithiazol-5-yl) formimidamide

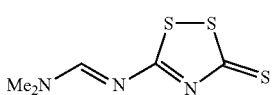

DMOCP: 2-chloro-5,5-dimethyl-1,3,2-dioxaphosphinane 2-oxide

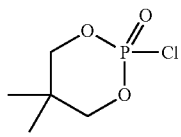

TBS: t-butyldimethylsilyl
3H-benzo[c][1,2]dithiol-3-one:

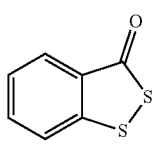

Example 1—Synthesis of Compound 1a

A full scheme of this synthesis is available in FIG. 1.

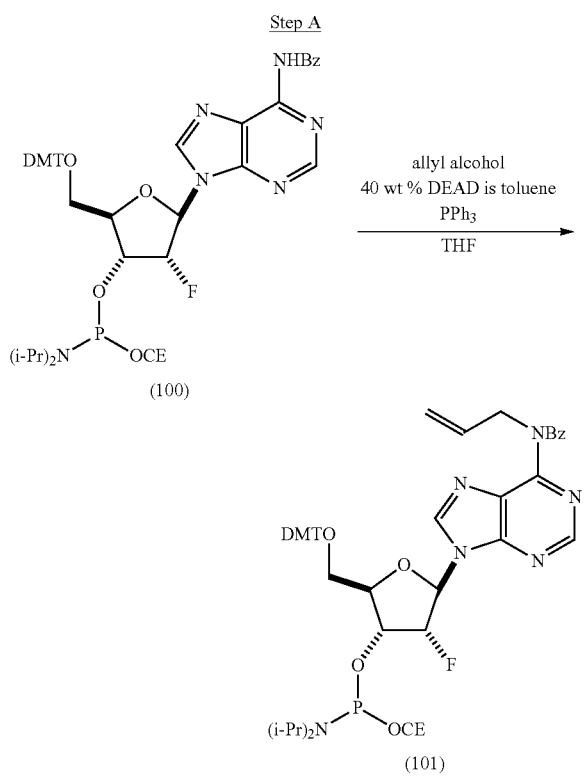

To a mixture of (2R,3R,4R,5R)-5-(6-benzamido-9H-purin-9-yl)-2-((bis(4-methoxyphenyl) (phenyl) methoxy) methyl)-4-fluorotetrahydrofuran-3-yl(2-cyanoethyl) diisopropylphosphoramidite (Compound 100) (mixture of phosphorous diastereomers; 80.0 g, 91.332 mmol, 1 eq, ChemGenes Corporation catalog #ANP-9151), allyl alcohol (9.63 ml, 142 mmol, 1.55 eq) and triphenylphosphine (38.3 g, 146 mmol, 1.60 eq) in THF (1.1 L) was added DEAD (40 wt % solution in toluene; 54.2 ml, 137 mmol, 1.5 eq.) at ambient temperature. Stirring was continued at ambient temperature and the reaction was monitored by LC/MS. Upon completion (19 h), the mixture was concentrated in vacuo (35° C.) and resultant mixture was purified by silica gel column chromatography (800 g×2 columns, 40 to 60% EtOAc in n-heptane buffered with 0.5% triethylamine) to give Compound 101 as a white foam (84.2 g, quantitative yield, mixture of phosphorous diastereomers).

$^1$H NMR (3:2 mixture of phosphorous diastereomers, 400 MHZ, CDCl$_3$) δ 1.14-1.21 (m, 12H) 2.40 (t, J=6.2 Hz, 1.2H) 2.59 (t, J=6.2 Hz, 0.8H) 3.27 (d, J=8.6 Hz, 1H) 3.52-3.66 (m, 5H) 3.78 (s 2.4H) 3.79 (s 3.6H) 4.28-4.34 (m, 1H) 4.84-4.96 (m, 0.4H) 4.99 (d, J=5.5 Hz, 2H) 4.95-5.10 (m, 0.6H) 5.05 (d, J=10.9 Hz, 1H) 5.22 (br d, J=17.6 Hz, 1H) 5.64 (br d, J=53.2 Hz, 0.6H) 5.70 (br d, J=51.6 Hz, 0.4H) 5.96-6.75 (m, 1H) 6.20 (d, J=16.0 Hz, 0.6H) 6.24 (d, J=17.2 Hz, 0.4H) 6.74-6.79 (m, 4H) 7.02-7.06 (m, 2H) 7.17-7.24 (m, 8H) 7.32-7.34 (m, 2H) 7.41-7.44 (m, 2H) 8.11 (s, 1H) 8.52 (s, 0.4H) 8.54 (s, 0.6H).

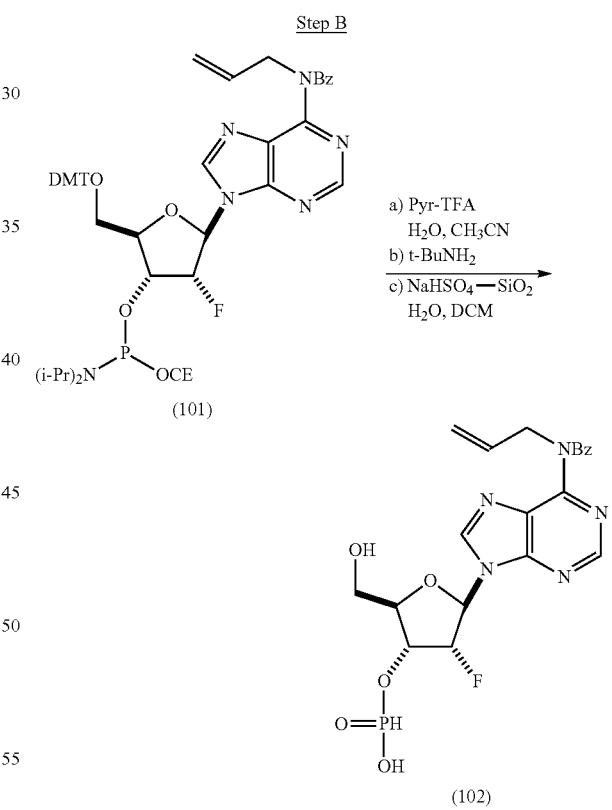

To a solution of Compound 101 (3.00 g, 3.28 mmol, 1 eq) in acetonitrile (30 ml) was added water (0.118 ml, 6.55 mmol, 2.0 eq) and pyridine trifluoroacetate salt (0.759 g, 3.93 mmol, 1.2 eq). After stirring at ambient temperature for 1 minute, tert-butylamine (14.5 g, 21.0 ml, 0.20 mol, 60 eq) was added. Upon complete cleavage of cyanoethyl group (monitored by LC/MS), the reaction mixture was concentrated in vacuo and azeotroped twice with acetonitrile. The crude mixture was dissolved in DCM (45.0 ml) and treated with water (0.118 ml, 6.55 mmol, 2.0 eq) and NaHSO₄—SiO₂ (1.18 g, 6.55 mmol, 2 eq) at ambient temperature. Upon complete cleavage of DMT group (monitored by LC/MS, approximately 1 hour), the reaction mixture was filtered and rinsed twice with DCM/MeOH (9/1, 20 ml). The combined filtrates were concentrated in vacuo and treated with 1:1 mixture of n-heptane/toluene (~30 ml). The top layer was removed by decantation. The same operation was repeated once more with n-heptane/toluene (1/1, 30 ml) and the bottom layer was azeotroped twice with acetonitrile to give Compound 102 (100% theoretical yield assumed). The product was used in the next step without further purification.

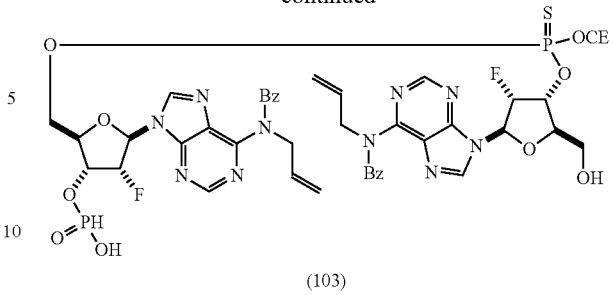

(103)

To a mixture of Compound 102 (1.56 g, 3.27 mmol, 1 eq) and Compound 101 (3.00 g, 3.28 mmol, 1 eq) in acetonitrile (30 ml) was added pyridine trifluoroacetate salt (azeotropically dried with pyridine; 0.760 g, 3.94 mmol, 1.25 eq). After 5 minutes, DDTT (0.840 g, 4.09 mmol, 1.30 eq, ChemGenes Corporation catalog #RN-1588) was added and, upon complete sulfurization (monitored by LC/MS), the reaction mixture was concentrated in vacuo. The residue was dissolved in DCM (30 ml) and treated with water (0.57 ml, 32 mmol, 10 eq) and 6% dichloroacetic acid (1.56 ml, 18.9 mmol, 6.0 eq) in DCM (30 ml). After 20 minutes, the reaction was quenched with pyridine (20 ml) and concentrated in vacuo. The residue was azeotroped with pyridine to give Compound 103 (3.22 g, 100% theoretical yield assumed). The product was used in next the step without further purification.

Step C

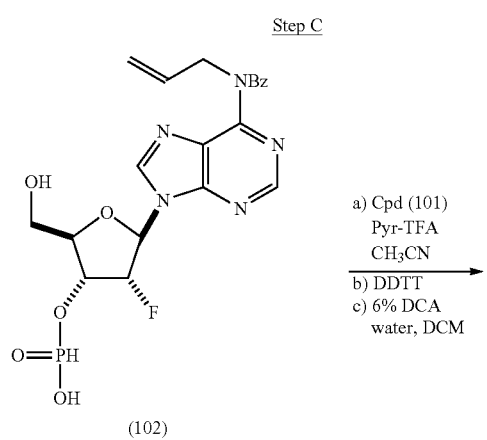

a) Cpd (101)
Pyr-TFA
CH₃CN
b) DDTT
c) 6% DCA
water, DCM (102)

Step D

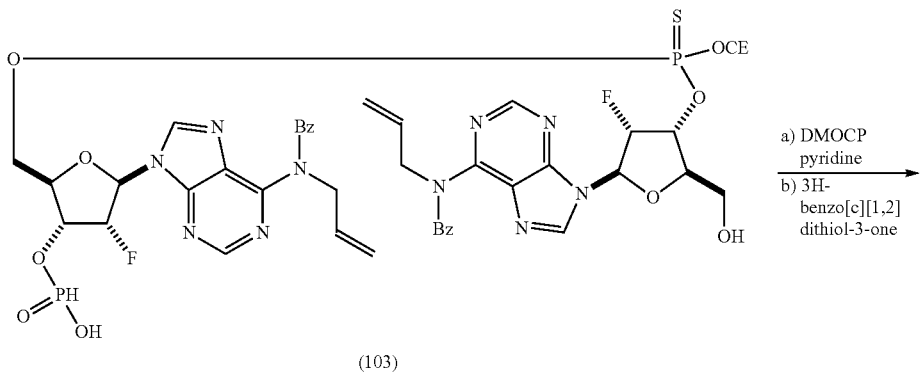

(103)

a) DMOCP
pyridine
b) 3H-benzo[c][1,2]dithiol-3-one

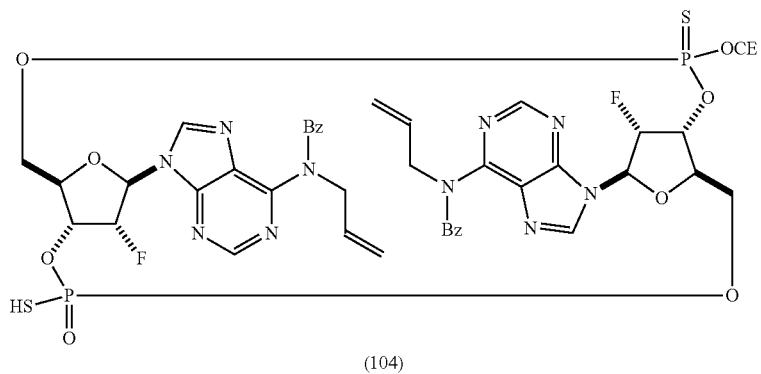

(104)

To a solution of Compound 103 (3.22 g, 3.15 mmol, 1 eq) in pyridine (100 ml) was added DMOCP (1.45 g, 7.88 mmol, 2.50 eq) at ambient temperature. Upon complete macrocyclization (monitored by LC/MS), water (1.7 ml, 94.5 mmol, ×10 fold relative to DMOCP) was added followed by 3H-benzo[c][1,2]dithiol-3-one (0.795 g, 4.73 mmol, 1.5 eq). Upon complete sulfurization (approximately 40 minutes), the reaction mixture was partially concentrated in vacuo to approximately 15 ml and poured into a mixture of saturated aqueous NaHCO₃ (50 ml) and water (30 ml). After 10 min stirring at ambient temperature, the mixture was extracted with 1:1 mixture of EtOAc/MTBE (60 ml×3 times). The organic layers were combined, washed with brine (25 ml), dried over MgSO₄ and concentrated in vacuo. The residue was purified by silica gel column chromatography (0-20% MeOH in DCM) to give Compound 104 (3.31 g, 3.20 mmol, 100% theoretical yield assumed) as a brown oil. The product was used in the next step without further purification.

Step E

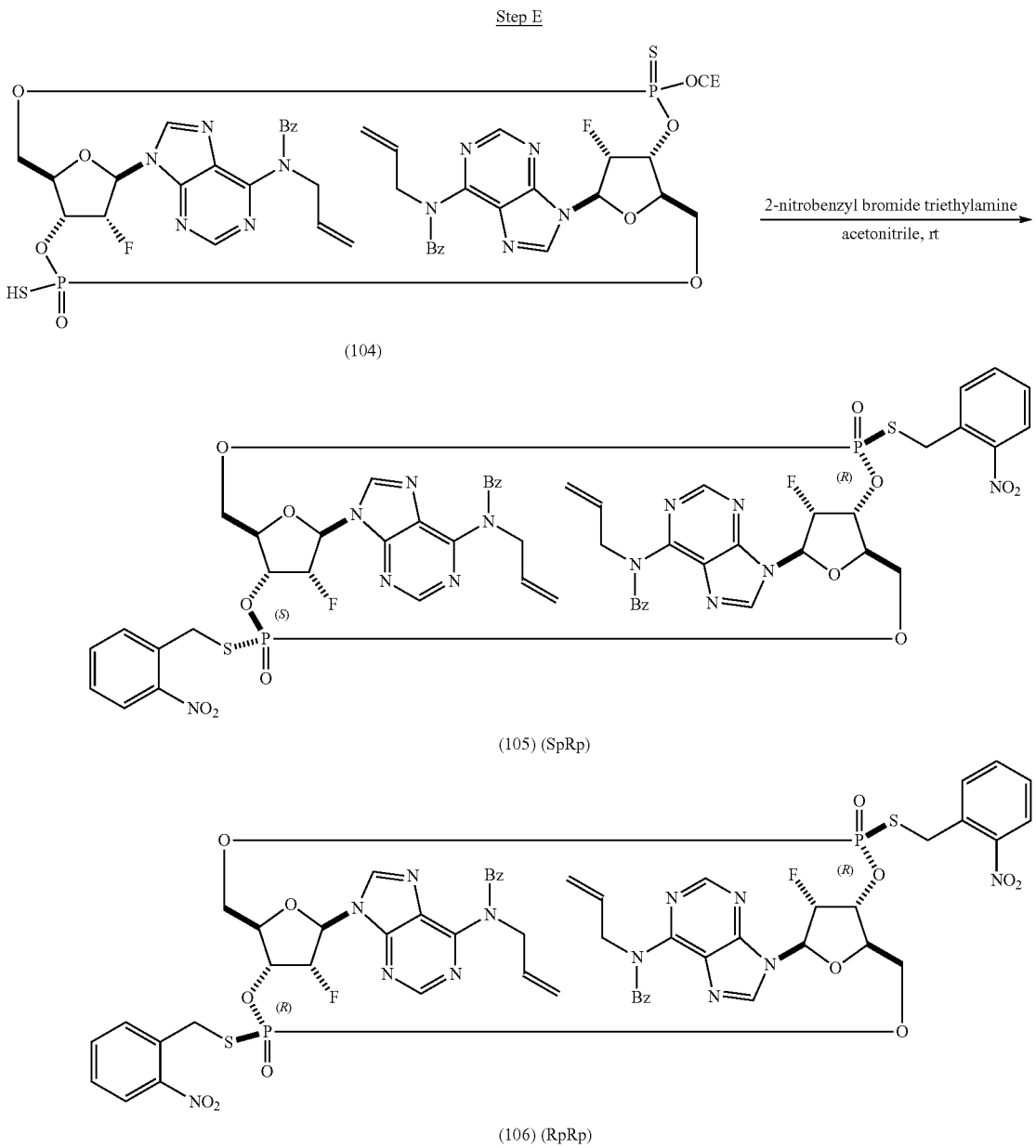

(104)

(105) (SpRp)

(106) (RpRp)

To a solution of Compound 104 (3.31 g, 3.20 mmol, 1 eq) in acetonitrile (66.2 ml) was added 2-nitrobenzyl bromide (2.42 g, 11.2 mmol, 3.50 eq) and triethylamine (1.78 ml, 12.8 mmol, 4.00 eq). Upon complete reaction (monitored by LC/MS, approximately 20 hours at ambient temperature), the reaction mixture was concentrated in vacuo and purified by silica gel column chromatography (60% ethyl acetate/n-heptane to 100% ethyl acetate) to give 0.568 g product as a mixture of phosphorous diastereomers. Preparative HPLC separation of the diastereomers gave Compound 105 (SR isomer; 0.225 g, 0.180 mmol, 5.6% overall yield from Compound 101) and Compound 106 (RR isomer; 0.187 g, 0.149 mmol, 4.7% overall yield from Compound 1).

Compound 105 (SpRp) ¹H NMR (400 MHz, CDCl₃) δ=8.63 (s, 1H), δ=8.61 (s, 1H), 8.04-8.00 (m, 2H), 7.99 (s, 1H), 7.90 (s, 1H), 7.65-7.44 (m, 8H), 7.40-7.31 (m, 4H), 7.25-7.21 (m, 4H), 6.15-5.89 (m, 5H), 5.61 (dd, J=52.0, 5.1 Hz, 1H), 5.55 (ddd, J=51.2, 4.7, 2.7 Hz, 1H) 5.51-5.42 (m, 1H), 5.31-5.22 (m, 2H), 5.11 (dd, J=3.9, 9.8 Hz, 2H), 5.04-4.95 (m, 4H), 4.55-4.37 (m, 7H), 4.29-4.12 (m, 3H)

Compound 106 (RpRp) ¹H NMR (400 MHZ, CDCl₃) δ=8.65 (s, 2H), 8.06 (dd, J=1.4, 8.0 Hz, 2H), 7.98 (s, 2H), 7.57-7.52 (m, 6H), 7.47-7.32 (m, 6H), 7.25-7.21 (m, 4H), 6.15 (d, J=18.7 Hz, 2H), 6.09-5.99 (m, 2H), 5.82-5.76 (m, 2H), 5.60 (dd, J=51.8, 4.9 Hz, 2H), 5.27 (dd, J=1.2, 17.2 Hz, 2H), 5.12 (dd, J=1.0, 10.4 Hz, 2H), 5.06-4.96 (m, 4H), 4.55-4.40 (m, 4H), 4.36-4.24 (m, 4H), 4.21-4.02 (m, 2H)

Preparative HPLC Conditions:

| | |
|---|---|
| Instrument | Agilent 1200 |
| HPLC column | Waters Sunfire Prep C18 OBD column, 5 um, 30 × 250 mm, #186003969 |
| Flow rate | 50 ml/min |
| mobile phase | A: water, B: acetonitrile |

| Gradient | Time (min) | 0 | 8 | 9.9 | 10 | 12 |
|---|---|---|---|---|---|---|
| | B % | 50 | 99 | 99 | 50 | 50 |

| | |
|---|---|
| Run time | 12 min |
| Injection volume | 150 ul (0.08 g/ml in acetonitrile) |
| detection | UV 254 nm |
| Retention time | Compound 105 (SpRp) 7.7 min |
| | Compound 106 (RpRp) 8.0 min |

Step F

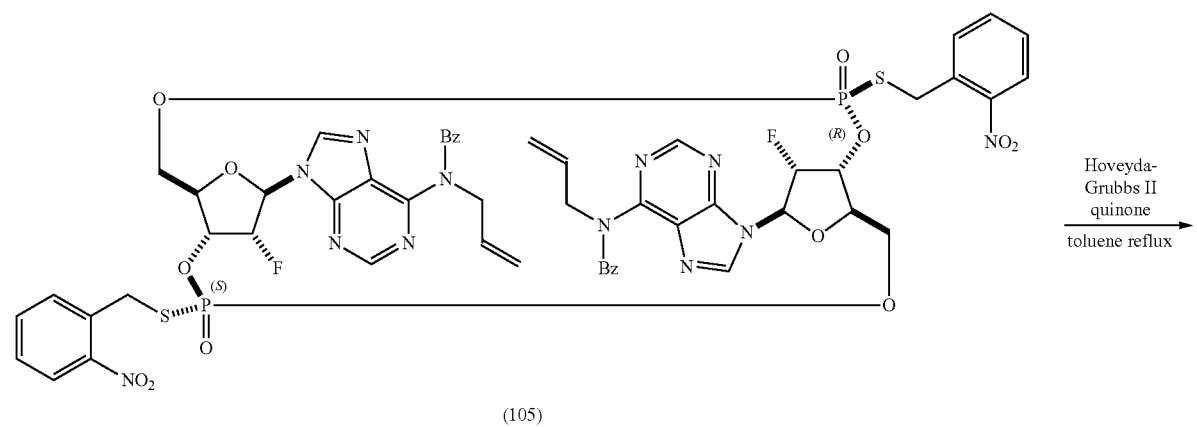

(105)

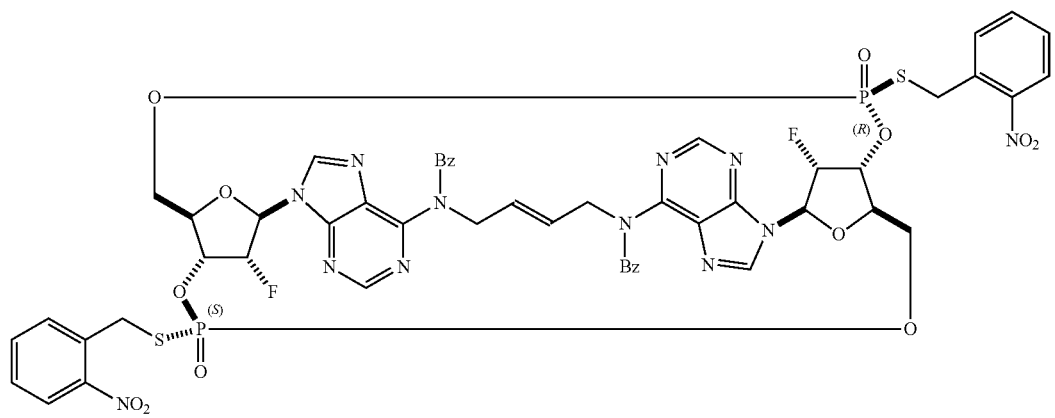

(107)

To a heated (90° C.) solution of Compound 105 (519 mg, 0.414 mmol, 1 eq) in toluene (519 ml) was added Hoveyda-Grubbs Catalyst™ 2nd generation ((1,3-Bis-(2,4,6-trimethylphenyl)-2-imidazolidinylidene)dichloro(o-isopropoxyphenylmethylene)ruthenium; available at SIGMA-ALDRITCH® Catalog No. 569755; CAS 301224-40-8; 91 mg, 0.15 mmol, 0.35 eq) and quinone (0.102 ml, 1.243 mmol, 3.0 eq). The mixture was heated to reflux and reaction progress was monitored by LC/MS. After 3 hours an additional catalyst was added (91 mg, 0.15 mmol, 0.35 eq) and the reaction was continued for additional 3 hours. After cooling down, the mixture was treated with DMSO (0.59 ml, 8.3 mmol, 20 eq) at ambient temperature for 15 hours, concentrated in vacuo and purified by silica gel column chromatography (SiO$_2$ 25 g, 66% ethyl acetate in n-heptane to 100% ethyl acetate) to give Compound 107 (200 mg, 0.163 mmol, 39% yield) as a brown dry foam.

$^1$H NMR (400 MHZ, CDCl$_3$) δ=8.19 (s, 1H), 8.12 (dd, J=7.8 Hz, 1.9 Hz, 1H), 8.10 (s, 1H), 8.02 (d, J=8.2 Hz, 1H), 7.89 (s, 1H), 7.63 (br d, J=7.0 Hz, 1H), 7.53-7.41 (m, 10H), 7.35-7.30 (m, 2H), 7.25-7.20 (m, 4H), 6.23 (d, J=17.6 Hz, 1H), 6.14 (d, J=18.8 Hz, 1H), 5.86-5.75 (m, 1H), 5.75 (dt, J=15.3, 5.0 Hz, 1H), 5.67 (dt, J=15.3, 4.7 Hz, 1H), 5.60 (dd, J=52.0, 3.9 Hz, 1H), 5.48 (dd, J=50.4, 3.9 Hz, 1H) 5.50-5.39 (m, 1H), 4.91-4.64 (m, 4H), 4.57-4.25 (m, 9H), 4.15 (d, J=7.03 Hz, 1H), 4.11 (d, J=7.03 Hz, 1H).

To a solution of Compound 107 (88 mg, 0.072 mmol, 1 eq) in 1,4-dioxane (1.76 ml) was added thiophenol (0.88 mL, 8.55 mmol, 119 eq) and triethylamine (0.88 mL, 6.31 mmol, 88 eq). The resulting mixture was stirred at ambient temperature. Upon complete reaction (monitored by LC/MS, 13 hours), methanol (5.28 ml) and 28% ammonium hydroxide (3.52 ml) were added and resultant mixture was heated to 50° C. Upon complete reaction (monitored by LC/MS, 5 hours), the mixture was cooled to ambient temperature and the resultant brownish slurry was filtered and rinsed with water (15 ml). The filtrate was filtered again to remove additional solids. The final filtrate was extracted twice with a 1:1 mixture of toluene and heptane (30 ml). The aqueous layer was concentrated in vacuo and then re-suspended in water (6 ml). The resulting solid was filtered off and the filtrate was subjected to preparative HPLC to give Compound 1 diammonium salt (also referred to as Compound 1a) (39 mg, 0.050 mmol, 70% yield) as a white solid.

Compound 1a (SpRp, trans) $^1$H NMR (400 MHZ, CD$_3$OD) δ=9.05 (s, 1H), 8.33 (s, 1H), 8.25 (s, 1H), 8.12 (s, 1H), 6.34 (br s, 2H), 5.88 (br s, 2H), 5.66 (br d, J=51.6 Hz, 1H), 5.59 (br d, J=52.2 Hz, 1H) 5.01 (br s, 2H), 4.68-4.34 (m, 6H), 4.07-3.82 (m, 2H), 3.79-3.55 (m, 2H); $^{31}$P NMR (162 MHz, CD$_3$OD) δ=55.48 (s, IP), 55.16 (s, IP).

Step G

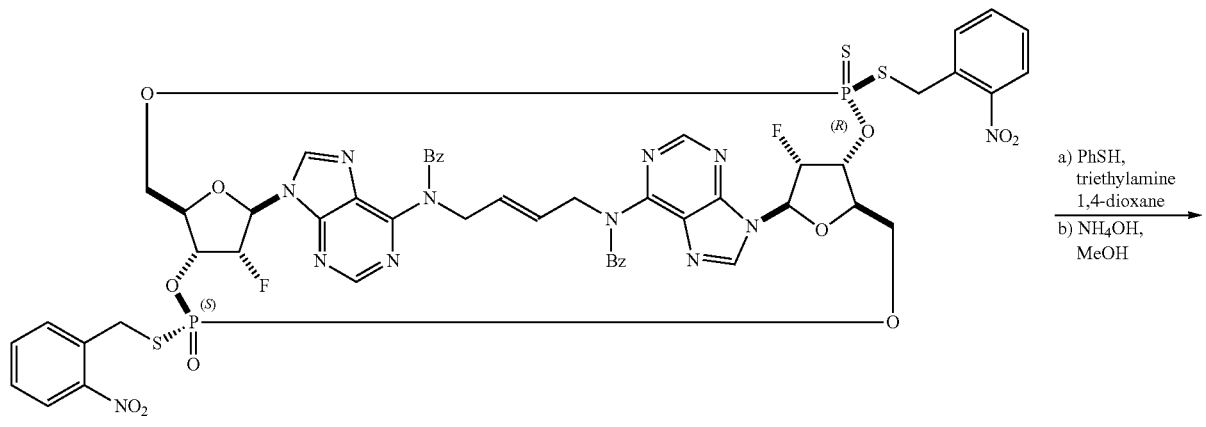

(107)

a) PhSH, triethylamine 1,4-dioxane
b) NH$_4$OH, MeOH

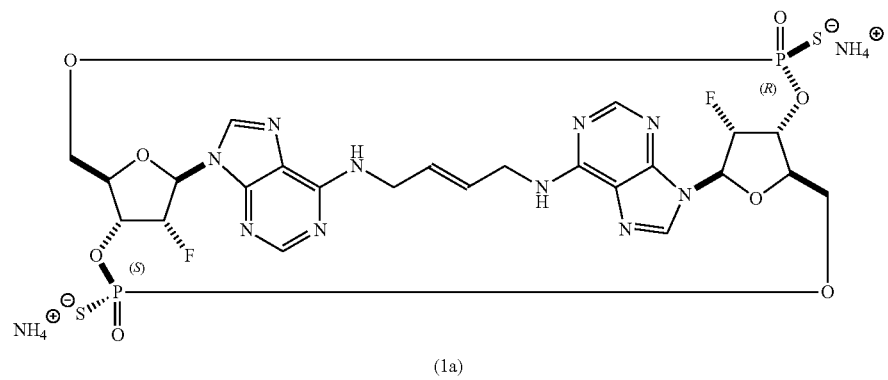

(1a)

Compound 1a Preparative HPLC Conditions:

| | |
|---|---|
| Instrument | Agilent 1200/1260 AS/FC |
| HPLC column | Waters XBridge C18, 10 x 100 mm, # 1413 |
| Flow rate | 3.0 ml/min |
| Column temperature | 35° C. |
| mobile phase | A: 0.1% NH$_4$OH in water, B: 0.1% NH$_4$OH in acetonitrile |
| Gradient (B%) | 0 → 50 |
| Run time | 20 min |
| Injection volume | 50 ul (4 mg/ml in water) |
| detection | UV 260 nm |
| Retention time | 6.5 min |

Example 1.1—Alternative Synthesis for Compound 1a

Figure 2A:
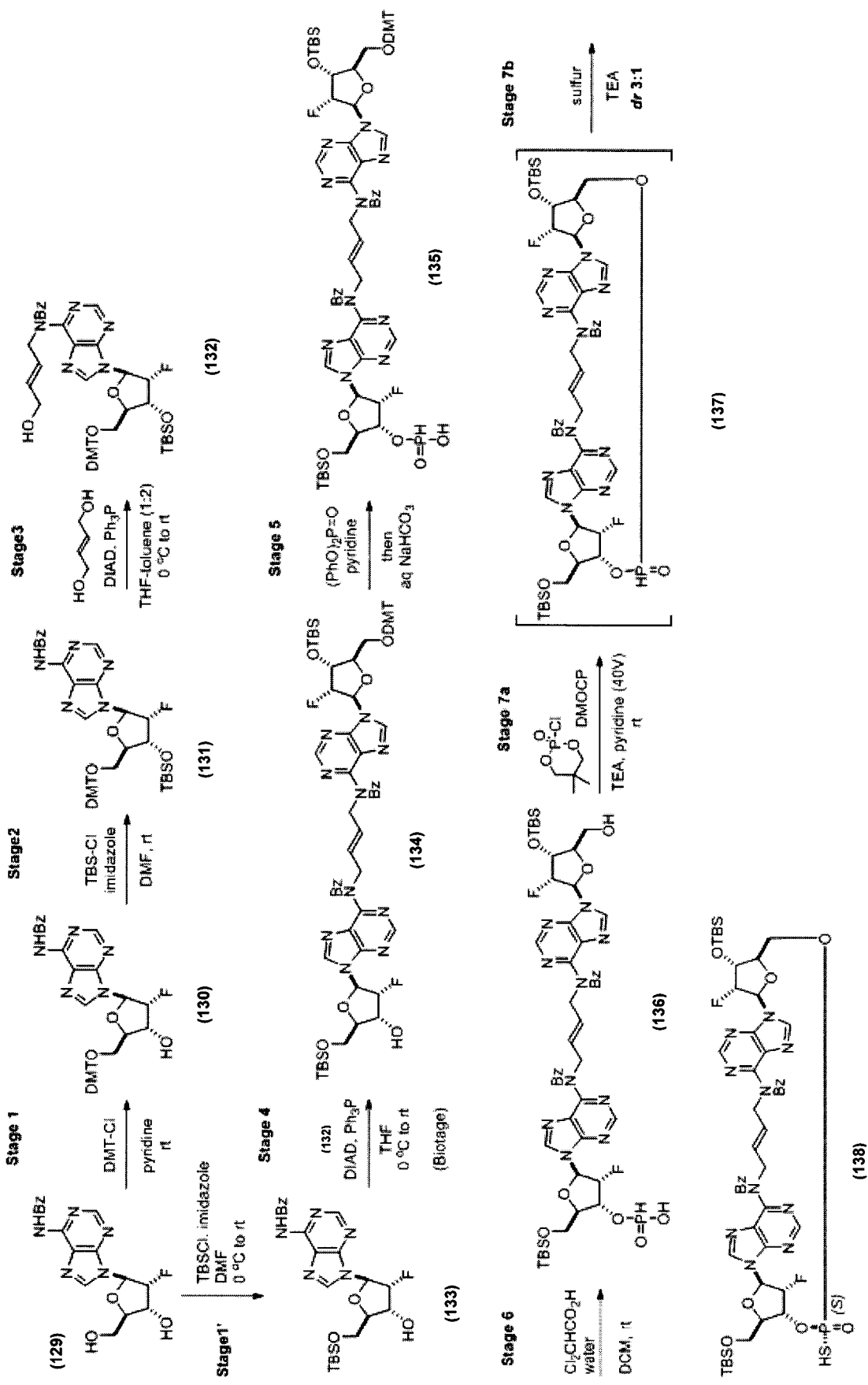
FIG. 2A and FIG. 2B show an alternate synthesis of Compound 1 and Compound 1a That alternate synthesis is also shown in FIG. 2C through FIG. 2E.
Figure 2B:
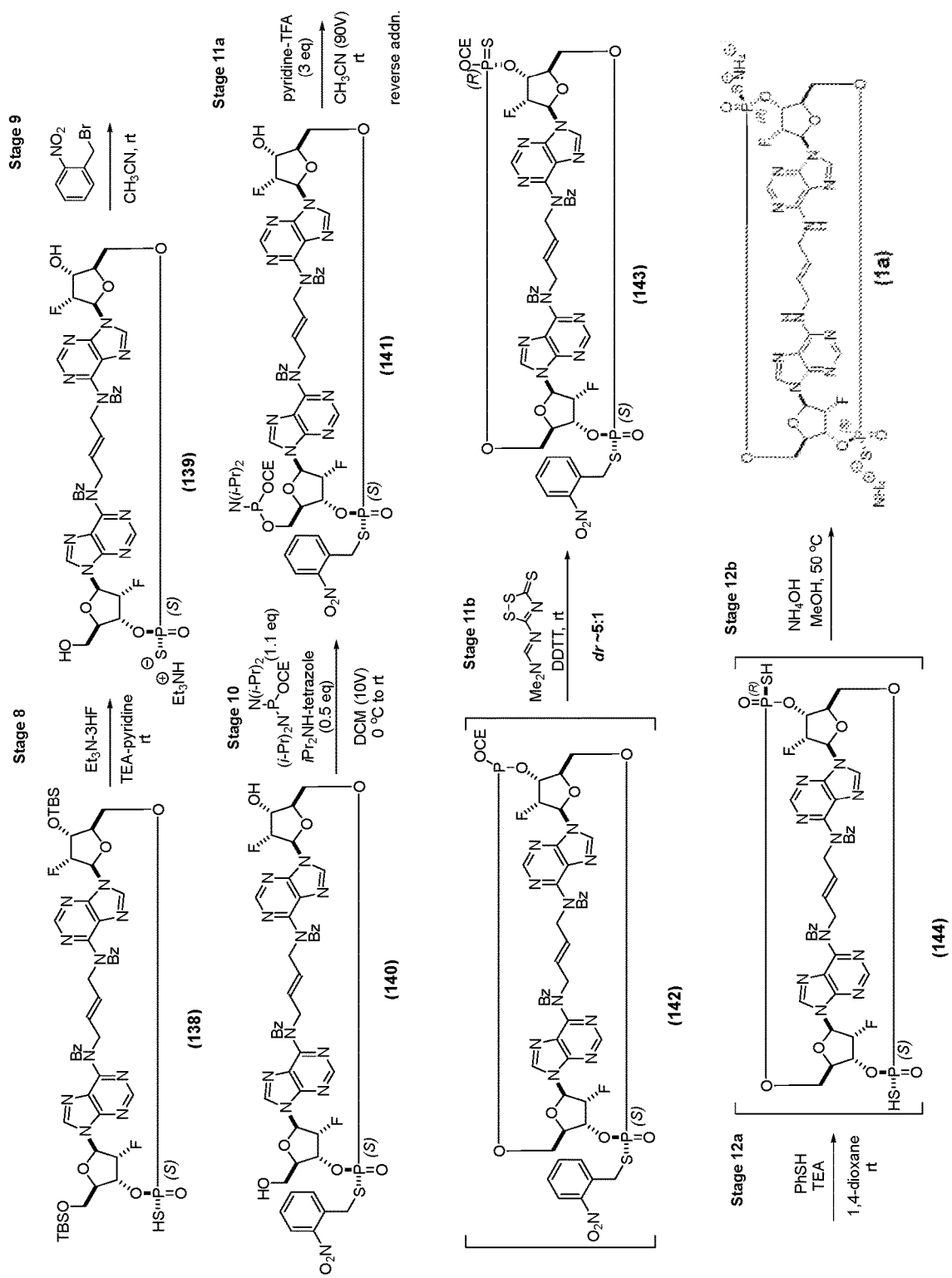
Figure 2C:
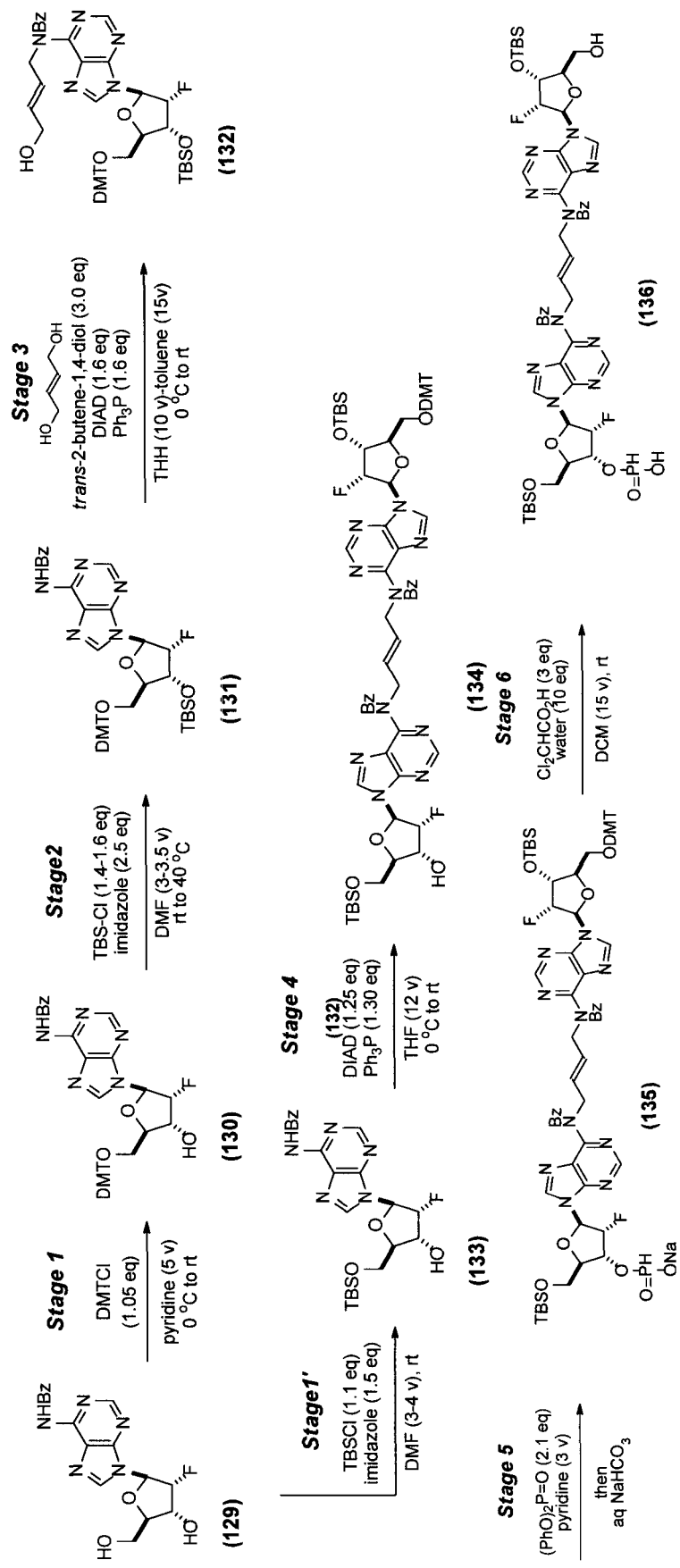
Figure 2D:
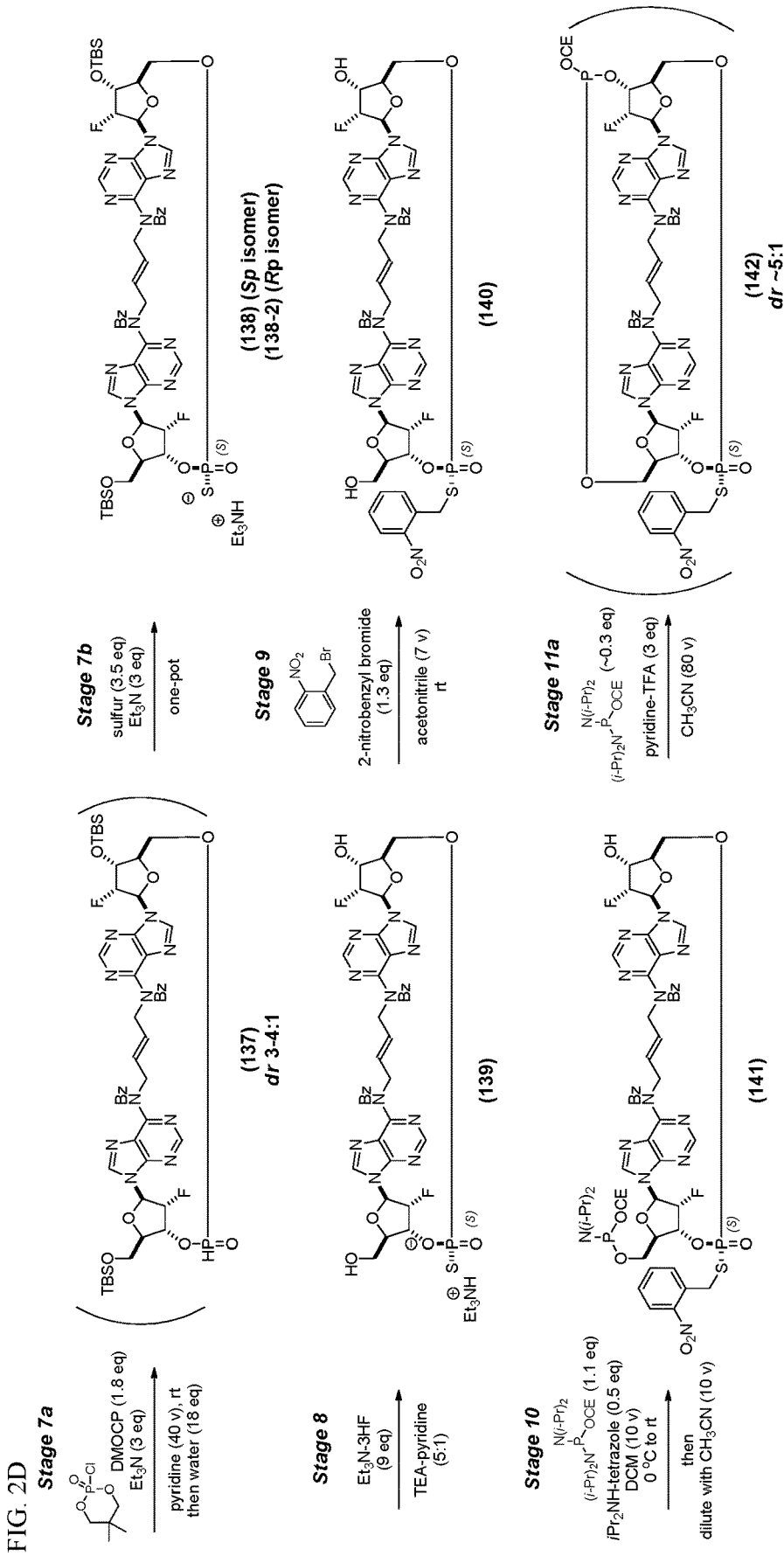
Figure 2E:
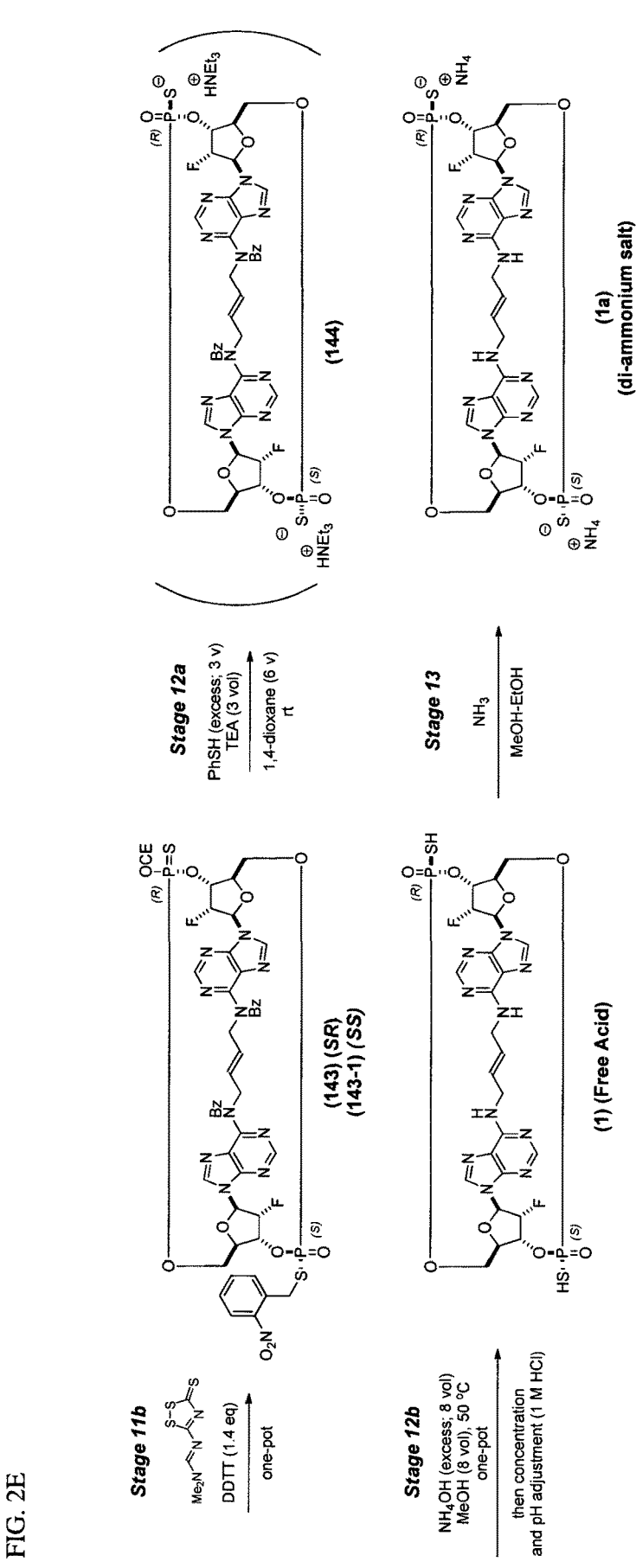

An alternative synthetic route for Compound 1a is set out in FIG. 2A and FIG. 2B, as well as in FIG. 2C and reported below.

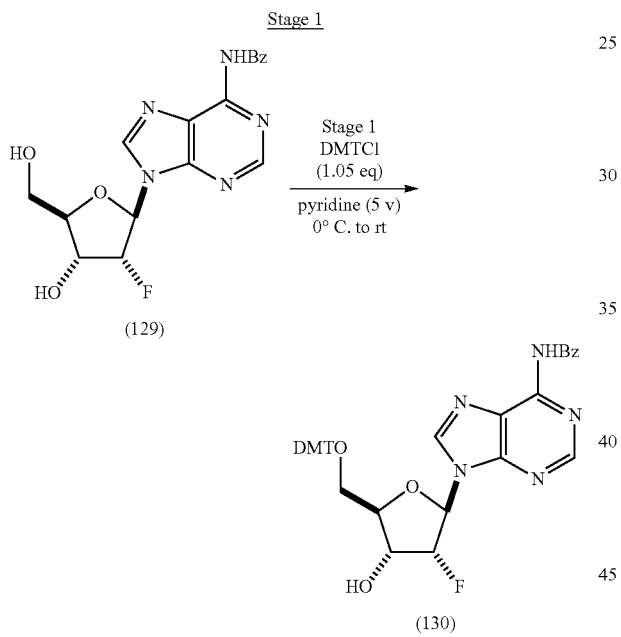

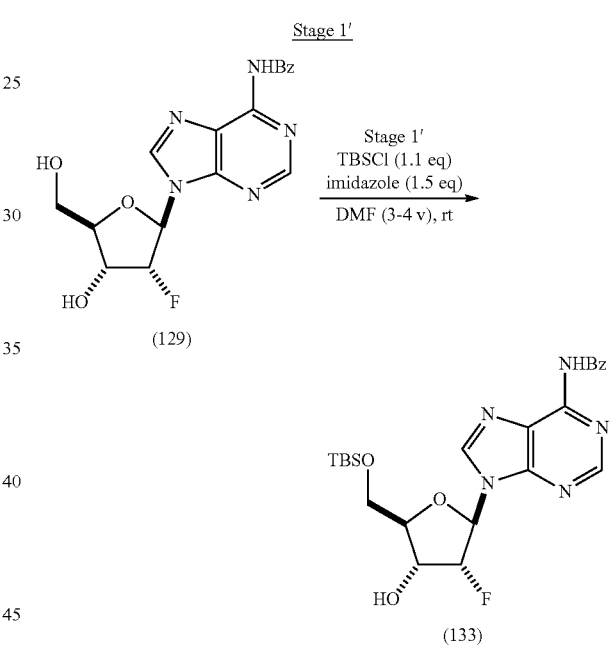

Compound 129 (570 g, 1.53 mol, 1 wt, 1 vol, 1 eq) was dissolved in pyridine (2.85 L, 35.2 mol, 4.89 wt, 5.0 vols, 23 eq). The mixture was cooled to 2.6° C. and treated with 4,4'-dimethoxytrityl chloride (DMTCl; 543 g, 1.60 mol, 0.953 wt, 1.05 eq). The mixture was stirred at 0 to 5° C. for 2 h and then allowed to warm to ambient temperature. The reaction was monitored by LC/MS and complete conversion was confirmed after overnight stirring. The reaction mixture was cooled to below 5° C. and quenched by treatment with MeOH (124 ml, 3.05 mol, 0.172 wt, 0.217 vol, 2.0 eq) for 15 minutes. The mixture was co-evaporated with toluene (2.00 L, 3.04 wt, 3.51 vol) under vacuum and then diluted with a mixture of EtOAc (2.850 L, 4.5 wt, 5.0 vol) and n-heptane (2.85 L, 3.42 wt, 5.0 vol). The organic layer was washed with saturated NaHCO$_3$ (9 wt % solution in water; 2.0 L, 3.5 vol). An additional EtOAc (2.85 L, 4.5 wt, 5.0 vol) was added to completely dissolve the crude product. After stirred for 5 minutes, the two layers were separated. The organic layer was washed with water (2.0 L, 3.5 wt, 3.5 vol). Solid began slowly precipitating out of the organic layer. The water layer was separated. The organic layer was then concentrated to approx. 1 vol. The crude product was slurried with a mixture of n-heptane (2.00 L, 2.40 wt, 3.51 vol) and toluene (0.50 L, 0.76 wt, 0.88 vol). After stirring for 15 minutes, the pale yellow solid was collected by vacuum filtration. The filter cake was sequentially rinsed with: (1) a mixture of n-heptane (0.60 L, 0.72 wt, 1.05 vol) and toluene (0.30 L, 0.46 wt, 0.53 vol), and then (2) n-heptane (3.00 L, 3.6 wt, 5.26 vol). The solid was dried with no heat for 30 minutes and then transferred to trays for drying at 50° C. in a vacuum oven overnight to give Compound 130 as pale yellow solid (996.7 g, 1.47 mol, 1.75 wt, 97% yield).

$^1$H NMR (400 MHZ, CHLOROFORM-d) δ=8.99 (s, 1H), 8.76 (s, 1H), 8.21 (s, 1H), 8.04-8.00 (m, 2H), 7.64-7.59 (m, 1H), 7.57-7.50 (m, 2H), 7.41-7.36 (m, 2H), 7.32-7.15 (m, 7H), 6.83-6.76 (m, 4H), 6.31 (dd, J=2.5, 17.0 Hz, 1H), 5.68 (ddd, J=2.3, 4.7, 52.7 Hz, 1H), 4.88-4.77 (m, 1H), 4.26-4.21 (m, 1H), 3.77 (s, 6H), 3.57 (dd, J=3.1, 10.9 Hz, 1H), 3.43 (dd, J=4.1, 10.7 Hz, 1H), 2.60 (br s, 1H)

Compound 129 (430 g, 1.15 mol, 1 wt, 1 vol, 1 eq) and imidazole (118 g, 1.73 mol, 0.274 wt, 1.50 eq) were dissolved in DMF (1.72 L, 3.78 wt, 4.0 vol) and the resultant mixture was cooled to 5° C. TBS-Cl (191 g, 1.27 mol, 0.444 wt, 1.10 eq) was added. The mixture was stirred at 0 to 11° C. for 2 h, allowed to slowly warm to ambient temperature (progress monitored by LCMS). The reaction was complete 6 h after TBS-Cl addition, yet allowed to stir at ambient temperature for an additional 20 h. The mixture was cooled to 2° C. and treated with methanol (93 ml, 74 g, 2.3 mol, 0.17 wt, 0.22 wt, 2.0 eq) for 10 minutes. The reaction mixture was diluted with a mixture of MTBE (1.72 L, 1.23 kg, 2.96 wt, 4.0 vol) and EtOAc (1.72 L, 1.55 kg, 3.60 wt, 4.0 vol) followed by saturated NH$_4$Cl (28 wt % solution in water; 2.15 L, 5.0 vol). Solids began slowly falling out of solution. The mixture was allowed to warm to 24° C. and water (1.08 L, 1.08 kg, 2.5 wt, 2.5 vol) was added to the (T-internal=22° C.). More solids began precipitating out of the mixture. An additional water (1.08 L, 1.08 kg, 2.5 wt, 2.5 vol) and MTBE (1.40 L, 1.04 kg, 2.4 wt, 3.3 vol) were added to the mixture. The off-white solid was collected by vacuum filtration. The reactor was rinsed with water (320 ml, 0.74 vol) and then MTBE (1.80 L, 1.33 kg, 3.10 wt, 4.19 vol) to transfer any remaining solid to the filter. The filter cake was rinsed sequentially with: (1) water (1.80 L, 1.80 kg, 4.2 wt, 4.2 vol). (2) water (1.80 L, 1.80 kg, 4.2 wt, 4.2 vol), (3) a mixture of MTBE (0.90 L, 0.67 kg, 1.5 wt, 2.1 vol) and n-heptane (0.90 L, 0.62 kg, 1.4 wt, 2.1 vol), (4) a mixture of MTBE (0.90 L, 0.67 kg, 1.5 wt, 2.1 vol) and n-heptane (0.90 L, 0.62 kg, 1.4 wt, 2.1 vol). The recovered solid was dried under vacuum at 40° C. over 2 days to give Compound 133 as white solid (483 g, 0.991 mol, 1.12 wt, 86% yield).

$^1$H NMR (400 MHZ, CHLOROFORM-d) δ=8.97 (s, 1H), 8.82 (s, 1H), 8.36 (s, 1H), 8.04-8.00 (m, 2H), 7.64-7.58 (m, 1H), 7.56-7.51 (m, 2H), 6.40 (dd, J=2.3, 16.0 Hz, 1H), 5.45 (ddd, J=2.7, 4.3, 53.1 Hz, 1H), 4.75-4.66 (m, 1H), 4.22-4.17 (m, 1H), 4.07 (dd, J=2.3, 11.7 Hz, 1H), 3.91 (dd, J=2.7, 11.7 Hz, 1H), 2.38 (dd, J=2.7, 7.0 Hz, 1H), 0.92 (s, 9H), 0.11 (s, 3H), 0.11 (s, 3H).

solid was collected by vacuum filtration. The filter cake was rinsed with: (1) water (4.0 L, 4.0 vol), (2) water (4.0 L, 4.0 vol), (3) n-heptane (4.0 L, 4.0 vol), (4) n-heptane (4.0 L, 4.0 vol). The recovered solid was dried under vacuum at 45° C. for 4 days to give Compound 131 as off-white solid (1.095 kg, 1.39 mol, 1.10 wt, 94% yield).

$^1$H NMR (400 MHZ, CHLOROFORM-d) δ=9.09 (s, 1H), 8.78 (s, 1H), 8.28 (s, 1H), 8.02 (d, J=7.4 Hz, 2H), 7.63-7.59 (m, 1H), 7.55-7.50 (m, 2H), 7.37 (d, J=7.1 Hz, 2H), 7.29-7.17 (m, 7H), 6.79 (d, J=7.9 Hz, 4H), 6.29 (dd, J=2.9, 16.2 Hz, 1H), 5.60 (ddd, J=2.7, 3.9, 53.1 Hz, 1H), 4.78 (ddd, J=4.7, 6.4, 15.8 Hz, 1H), 4.26-4.22 (m, 1H), 3.77 (s, 6H), 3.58 (dd, J=3.1, 10.9 Hz, 1H), 3.26 (dd, J=3.7, 10.7 Hz, 1H), 0.85 (s, 9H), 0.10 (s, 3H), 0.02 (s, 3H)

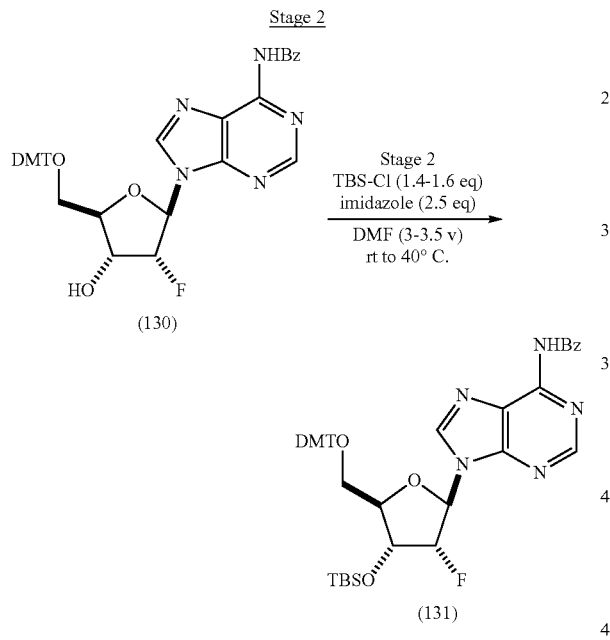

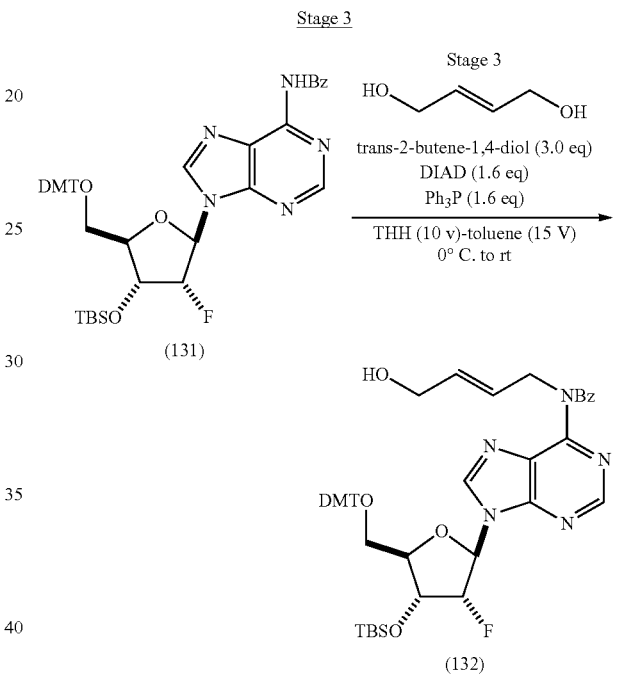

Compound 130 (993 g, 1.47 mol, 1 wt, 1 vol, 1 eq) and imidazole (150 g, 2.20 mol, 0.151 wt, 1.5 eq) were dissolved in DMF (3.48 L, 3.28 kg, 3.3 wt, 3.5 vol) and the mixture was cooled to 5° C. TBS-Cl (244 g, 1.62 mol, 0.245 wt, 1.10 eq) was added. The reaction was stirred at 0 to 5° C. for 2 h, allowed to slowly warm to ambient temperature and monitored by LCMS. After 17 h, an additional imidazole (100 g, 1.47 mol, 0.10 wt, 1.0 eq) and TBS-Cl (111 g, 735 mmol, 0.112 wt, 0.50 eq) were added and stirring was continued at ambient temperature for 2 h and at 35° C. for 2 h. The resulting mixture was cooled to 13.6° C. and treated with MeOH (119 ml, 2.94 mol, 2 eq) for 10 minutes. In a separate reactor was added ice (5 kg, 5 wt) and saturated NH$_4$Cl (28 wt % solution in water; 5.0 L, 5 vol). The reaction mixture was added to the ice/NH$_4$Cl mixture. An off white solid began precipitating out of solution immediately. An additional 2 kg of ice (2 kg, 2 wt) and water (3.0 L, 3 vol) were added to the mixture. The reaction flask was rinsed with water (0.50 L, 0.5 vol) and the rinsate was added to the mixture. n-heptane (2.00 L, 2 vol) was added to the mixture and stirring was continued for 10 minutes. The off white Compound 131 (1000 g. 1.27 mol, 1 wt, 1 vol, 1 eq) and trans-2-butene-1,4-diol (olefin geometry confirmed by H-NMR; 335 g, 3.80 mol. 0.335 wt, 3.0 eq) were azeotroped twice with THF (3.0 L, 3.0 vol). The residue was dissolved in a mixture of THF (10 L, 10 vol) and toluene (15 L, 15 vol). Triphenylphosphine (432 g, 1.65 mol, 0.432 wt, 1.3 eq) was added and then the reaction mixture was cooled to −5° C. DIAD (0.320 L, 1.65 mol, 333 g, 0.333 wt, 0.320 vol, 1.3 eq) was added slowly over 20 minutes while keeping T-internal below 5° C. The reaction was stirred at 0-5° C. for 1 h and monitored by LCMS. The ice bath was removed and the mixture was allowed to warm up to rt. After overnight stirring (17 h), an triphenylphosphine (83 g, 0.32 mol, 0.083 wt, 0.25 eq) and DIAD (62 ml, 0.32 mol, 64 g, 0.064 wt, 0.062 vol, 0.25 eq) were added. After additional 1 h at rt, the reaction mixture was diluted with MTBE (10 L, 10 vol), washed twice with half-saturated NaCl (18 wt % solution in water; 2×4 L) and concentrated in vacuo to a thick oil. The mixture was re-dissolved in a mixture of MTBE (4.00 L, 4 vol) and n-heptane (0.50 L, 0.5 vol) and then cooled to 0° C. A seed crystal of triphenylphosphine oxide was added to the solution. Solids slowly began precipitating out of solution and was stirred overnight. The white solid was collected by vacuum filtration and rinsed with MTBE (2 L, 2 vol) to isolate 540 g of triphenylphosphine oxide. The filtrate was concentrated and purified via Biotage 150 L KP-Sil (SiO$_2$ 5 kg; pretreated with 1% TEA in Hep/etOAc; eluents: heptane/EtOAc (48 L of 33% EtOAc with 1% TEA, 24 L of 50% EtOAc with 1% TEA, 24 L of 66% EtOAc with 1% TEA)→100% EtOAc with 1% TEA). The column was monitored by TLC (2:1 EtOAc/n-heptane). The clean product fractions were combined and concentrated under vacuum to give Compound 132 as pale white foam solid (634 g, contained 14 wt % DIAD derived co-product, net 545 g, 0.63 mol, 50% adjusted yield). The mixture fractions were combined and concentrated under vacuum to give pale yellow foam solid (750 g), which was subjected to repurification via Biotage 150M HP-Sphere (2.5 kg SiO$_2$; pretreated with 1% TEA in Hep/EtOAc; loaded sample with toluene eluents: Hep/EtOAc/1% TEA (12 L of 50% EtOAc with 1% TEA, 16 L 66% EtOAc with 1% TEA)→EtOAc with 1% TEA). The column was monitored by TLC (2/1/0.03 EtOAc/n-hep/TEA). The clean product fractions were combined and concentrated under vacuum to give additional Compound 132 as pale white foam solid (206 g, 0.24 mol, 18% yield).

$^1$H NMR (400 MHZ, CHLOROFORM-d) δ=8.58 (s, 1H), 8.10 (s, 1H), 7.43-7.37 (m, 2H), 7.32-7.28 (m, 2H), 7.24-7.15 (m, 8H), 7.03-6.98 (m, 2H), 6.78-6.73 (m, 4H), 6.18 (dd, J=2.7, 17.2 Hz, 1H), 5.88 (td, J=5.5, 15.6 Hz, 1H), 5.77 (td, J=5.1, 15.6 Hz, 1H), 5.60 (ddd, J=2.7, 4.3, 53.1 Hz, 1H), 5.03-4.96 (m, 2H), 4.91 (ddd, J=4.5, 6.6, 16.6 Hz, 1H), 4.18-4.14 (m, 1H), 3.88-3.82 (m, 2H), 3.78 (s, 6H), 3.52 (dd, J=2.7, 10.9 Hz, 1H), 3.14 (dd, J=3.5, 10.9 Hz, 1H), 0.85 (s, 9H), 0.10 (s, 3H), 0.01 (s, 3H).

wt, 2.50 vol) and then re-dissolved in a mixture of MTBE (2.40 L, 1.78 kg, 2.2 wt, 3.0 vol) and n-heptane (800 ml, 547 g, 0.68 wt, 1.0 vol). The solution was seeded with triphenylphosphine oxide and cooled to 5° C., diluted with n-heptane (400 ml, 274 g, 0.34 wt, 0.50 vol) and stirred at 5° C. for 30 minutes. The white solid precipitate was collected by vacuum filtration and rinsed with 2:1 (v/v) mixture of MTBE and n-Heptane (1.8 L) to give triphenylphosohine oxide (455 g). The filtrate was concentrated under vacuum and purified via Biotage 150 L KP-Sil (SiO$_2$ 5 kg; pretreated with 1% TEA; loaded sample by dissolving in toluene eluents: 9:1 heptane/EtOAc (16 L) and 15 TEA, 3.6:1 (46 L), 2:1 (20 L) and 1% TEA, 1:1 (30 L) and 1% TEA, and 100% EtOAc (16 L) and 1% TEA). The combined clean product fractions were concentrated under vacuum to give Compound 134 as off white solid foam (662.2 g). The mixture fractions were combined and concentrated under vacuum (480 g). A white insoluble solid formed by dilution with toluene (300 ml) prior to loading on Biotage 150 L was removed by vacuum filtration. The material soluble in toluene was purified via Biotage 150M HP-Sphere (SiO$_2$ 2.5 kg (pretreated with 1% TEA); sample loading with toluene; eluents: 2:1 heptane/EtOAc (26 L) w/1% TEA, 1:1 (25 L) w/1% TEA, 1:4 (34 L) w/1% TEA). The column was monitored by TLC (1:1 heptane/EtOAc). The combined clean product fractions were concentrated under vacuum to give additional Compound 134 as off white solid foam (165.5 g. Total 662.2+165,5 g=827.7 g, 930 mmol, 1.03 wt, 67% yield).

$^1$H NMR (400 MHz, CHLOROFORM-d) δ=8.47 (s, 1H), 8.39 (s, 1H), 8.20 (s, 1H), 8.01 (s, 1H), 7.38-7.31 (m, 5H),

Stage 4

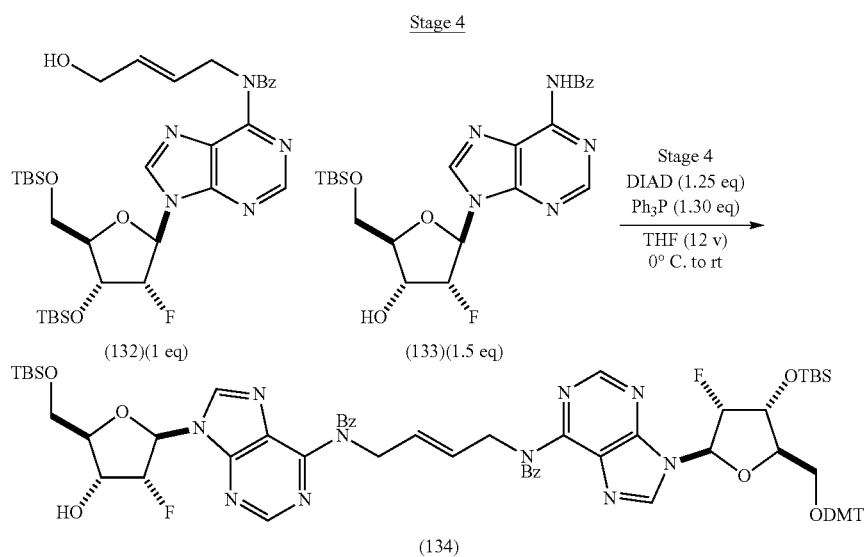

Compound 132 (800 g, 0.930 mol, 1 wt, 1 vol. 1 eq) and Compound 133 (522 g, 1.07 mol, 0.652 wt, 1.15 eq) were azeotropically dried with THF (2×3 L, 2×3.8 vol) and re-dissolved in THF (9.60 L, 8.45 kg, 12.0 vol) at rt. Triphenylphosphine (317 g. 1.21 mol, 0.396 wt, 1.30 eq) was added and the mixture was cooled below −5° C. DIAD (226 ml, 1.16 mol, 235 g, 0.294 wt, 0.283 vol, 1.25 eq) was added T-internal below 7° C. The reaction was allowed to warm to rt slowly. The reaction was monitored by LCMS. After 21 h, the reaction mixture was concentrated in vacuo to a thick oil, azeotroped with n-heptane (2.00, 1.37 kg, 1.71

7.27-7.19 (m, 6H), 7.14-7.06 (m. 3H), 6.93-6.87 (m, 2H), 6.76 (d, J=8.6 Hz, 4H), 6.26 (dd, J=2.0, 16.0 Hz, 1H), 6.15 (dd, J=2.7, 17.2 Hz, 1H), 5.86 (dd, J=4.7, 15.2 Hz, 1H), 5.80 (dd, J=4.7, 15.2 Hz, 1H), 5.51 (ddd, J=2.7, 4.3, 52.8 Hz, 1H), 5.31 (ddd, J=2.0, 4.3, 52.8 Hz, 1H), 4.87 (d, J=4.7 Hz, 2H), 4.85-4.81 (m, 1H), 4.79 (d, J=4.3 Hz, 2H), 4.71-4.59 (m, 1H), 4.20-4.13 (m, 2H), 4.06 (dd, J=2.7, 11.3 Hz, 1H), 3.90 (dd, J=2.7, 11.7 Hz, 1H), 3.77 (s, 6H), 3.52 (dd, J=3.1, 10.9 Hz, 1H), 3.18 (dd, J=3.9, 10.9 Hz, 1H), 0.92 (s, 9H), 0.84 (s, 9H), 0.10 (s, 3H), 0.09 (s, 6H), 0.07 (s, 3H)

Stage 5-6

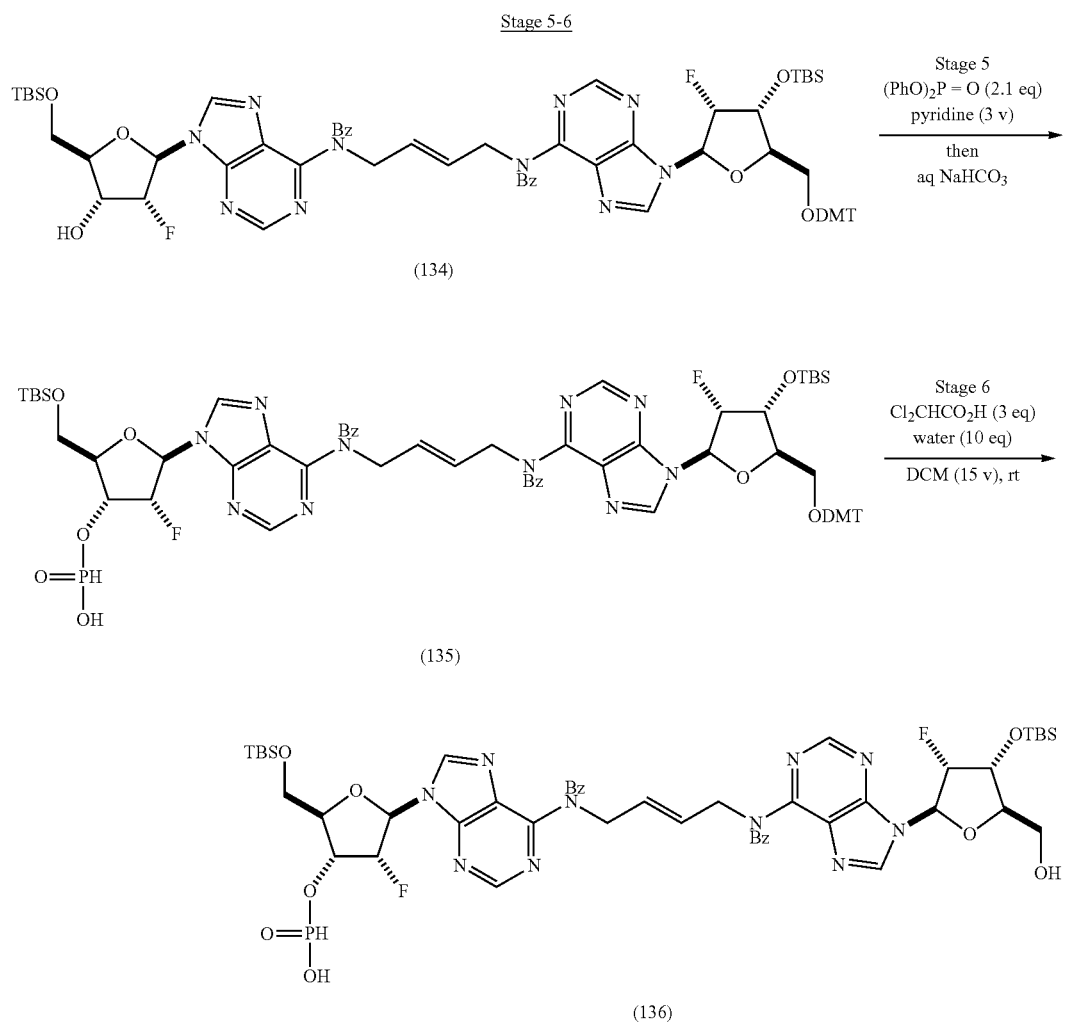

To a solution of Compound 134 (410.7 g, 309 mmol, 1 wt, 1 vol, 1 eq) in pyridine (1.23 L, 1.21 kg, 15.2 mol, 2.9 wt, 3.0 vol, 49 eq) was added diphenyl phosphite (90 ml, 109 g, 0.46 mol, 0.26 wt, 0.22 vol, 1.5 eq). The reaction was stirred at rt and was monitored by LCMS. After 2 h (80% conversion) an additional diphenyl phosphite (29.9 ml, 36.2 g, 155 mmol, 0.088 wt, 0.073 vol, 0.50 eq) was added. After an additional 1 h an extra diphenyl phosphite (6.0 ml, 7.2 g, 31 mmol, 0.018 wt, 0.015 vol, 0.10 eq) was added and the reaction was continued for an additional 0.5 h (98% conversion). The reaction mixture was added to a mixture of saturated $NaHCO_3$ (9 wt % solution in water; 2.1 L, 5 vol) and water (1.0 L ml, 2.5 vol) while keeping T-internal 4.7 to 12° C. The reactor was rinsed with a small volume of EtOAc. Stirring was continued at rt for 30 minutes and monitored the reaction by LCMS (100% conversion). The reaction mixture was extracted twice with 1:1 mixture of EtOAc and MTBE (2×8.2 L, 2× 20 vol). The combined organic layers were washed with water (4.1 L, 10 vol), concentrated in vacuo and azetroped with toluene (3×4.1 L, 3×10 vol; continuous feeding) for removal of pyridine to give Compound 135 (0.55 eq pyridine remained).

Stage 6—The crude Compound 135 was dissolved in dichloromethane (3.08 L, 4.07 kg, 9.9 wt, 7.5 vol) at ambient temperature. Water (55.7 ml, 0.136 vol, 10 eq) was added followed by a solution of dichloroacetic acid (77 ml, 120 g, 0.93 mol, 0.29 wt, 0.19 vol, 3.0 eq) in DCM (3.08 L, 7.5 vol) while keeping the internal T below 25° C. (Turned into an orange solution). After 30 min, triethylsilane ($Et_3SiH$; 494 ml, 359 g, 3.09 mol, 0.875 wt, 1.20 vol, 10.0 eq) (T-internal went from 18.2° C. to 17° C.) was added and stirring was continued for 20 min. Triethylamine (431 ml, 313 g, 3.09 mol, 0.762 wt, 1.05 vol, 10.0 eq) was added (T-internal went from 17.8° C. to 22° C.). The mixture was concentrated to 1.55 kg (3.8 wt), redissolved in EtOAc (6.2 L, 5.5 kg, 14 wt, 15 vol), sequentially washed with: (1) water (1.0 L, 2.5 vol) and saturated $NaHCO_3$ (9 wt % solution in water, 0.82 L, 2.0 vol). The crude product EtOAc solution was stored at −20° C. over night.; 0.82 L, 2.0 vol) and in next day, the solution was concentrated in vacuo at 25° C. The crude mixture thus obtained (654 g) was triturated with: (1) n-heptane (3.01 L, 7.5 vol), (2) a mixture of n-heptane (2.46 L, 6.0 vol) and toluene (0.82 L, 2.0 vol). The solution part (supernatant) was decanted off and the solid remained at the bottom was dissolved in acetonitrile (4.1 L, 10 vol). The mixture was concentrated in vacuo at 25° C. and azetroped with acetonitrile twice to give Compound 136. The product was used for the subsequent stage without purification (theoretical 100% yield assumed).

Stage 7

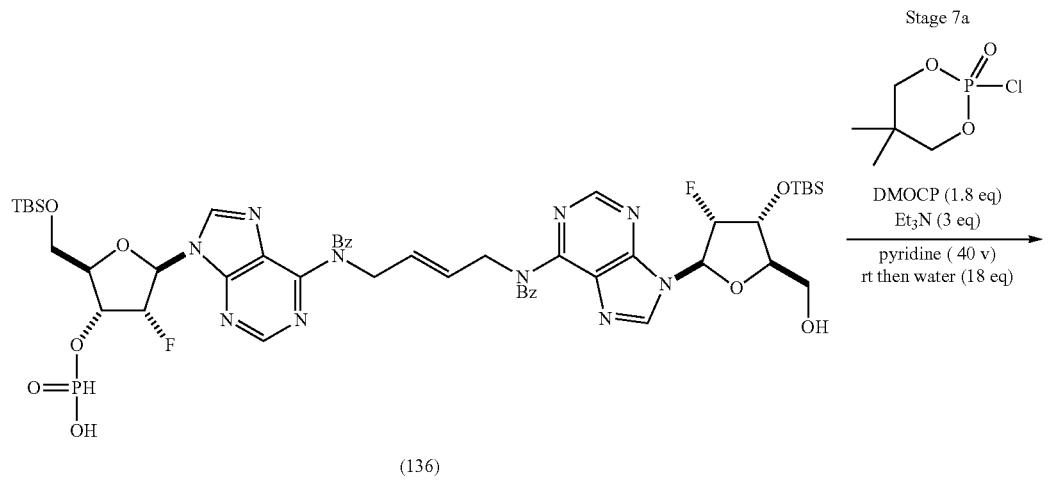

(136)

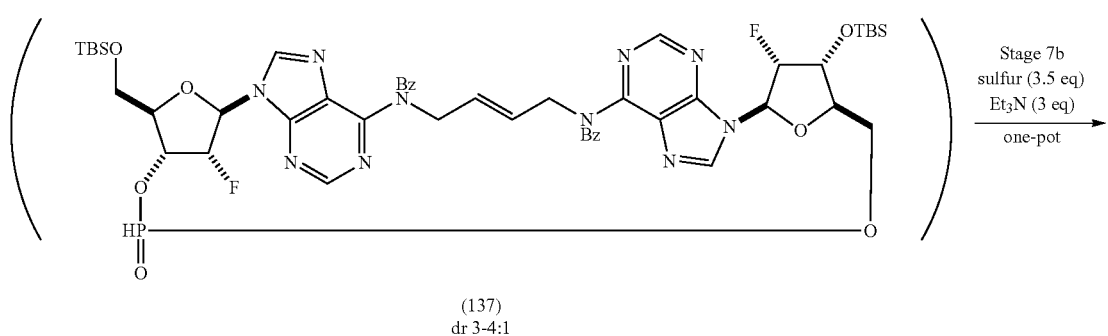

(137)
dr 3-4:1

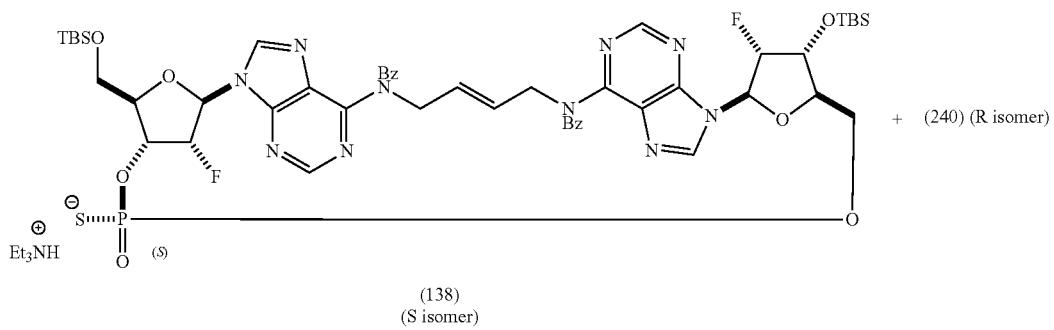

(138)
(S isomer)

+ (240) (R isomer)

Stage 7a Compound 136 (337 g, 309 mmol, 1 wt, 1 vol, 1 eq) was dissolved in in anhydrous pyridine (13.5 L, 13.2 kg, 39 wt, 40 vol) at rt. Triethylamine (129 ml, 927 mmol, 94 g, 0.28 wt, 0.38 vol, 3.0 eq) was added followed by 2-chloro-5,5-dimethyl-1,3,2-dioxaphosphinane 2-oxide (DMOCP; 103 g, 556 mmol, 0.31 wt, 1.80 eq). The resultant mixture was stirred at ambient temperature for 30 minutes and monitored by LCMS (100% conversion) to generate Compound 137.

Stage 7b TEA (129 ml, 927 mmol, 94 g, 0.28 wt, 0.38 vol, 3.0 eq), water (100 ml, 5.56 mol, 0.30 wt, 0.30 wt, 18 eq) and sulfur (34.7 g, 1.08 mol, 0.10 wt, 3.5 eq) were added to the above mixture of Compound 137. After 90 minutes (100% conversion), NaHCO$_3$ (9 wt % solution in water; 3.37 L, 10 vol) was added while keeping T-internal below 30° C. (16.6° C. to 27° C.). The resultant mixture was filtered for removal of salts. The filtrate was concentrated the mixture in vacuo, diluted with MTBE (5.1 L, 15 vol), and wash twice with NaCl (30 wt % solution in water; 2×1.35 L, 2×4 vol). Insoluble solids were filtered off and the filtrate was concentrated in vacuo and azeotroped with toluene (4.0 L, 12 vol). The resulting solid was removed by filtration and the crude mixture was dissolved in toluene and purified via Biotage 150 L KP-Sil (SiO$_2$ 5 kg; pretreated with Hep/EtOAc/TEA (1.5/1.5/0.03 CV); eluted with: EtOAc/TEA (3/0.03 CV), EtOAc/MeOH/TEA (4/0.2/0.04 CV), EtOAC/

MeOH/TEA (2/0.2/0.02CV) The column was monitored by TLC (EtOAC/MeOH/TEA=9/1/0.1). Fractions containing the Sp isomer were combined and concentrated under vacuum to give Compound 138 as light pink foam solid (Sp isomer; 154 g, 128 mmol, 0.46 wt, 41.3% yield). Fractions containing the Rp isomer were combined and concentrated under vacuum to give Compound 240 as light pink foam solid (Rp isomer; 64 g, 53 mmol, 0.19 wt, 17% yield).

Compound 138 (Sp Isomer):
$^1$H NMR (400 MHZ, CHLOROFORM-d) δ=8.51 (s, 1H), 8.50 (s, 1H), 8.22 (s, 1H), 8.14 (s. 1H), 7.49-7.44 (m, 2H), 7.38-7.27 (m, 4H), 7.25-7.21 (m, 2H), 7.14 (t, J=7.1 Hz, 2H), 6.44 (dd, J=2.5, 13.9 Hz, 1H), 6.18 (d, J=15.2 Hz, 1H), 5.78 (td, J=6.3, 15.6 Hz, 1H), 5.69 (td, J=4.7, 15.6 Hz, 1H), 5.56 (dd, J=3.9, 50.8 Hz, 1H), 5.20-5.06 (m, 1H), 4.95-4.79 (m, 4H), 4.69 (dd, J=4.3, 16.0 Hz, 1H), 4.54-4.38 (m, 3H), 4.35 (d, J=5.5 Hz, 1H), 4.32-4.29 (m, 1H), 4.05 (dd, J=1.6, 11.7 Hz, 1H), 3.91 (dd, J=3.1, 11.7 Hz, 1H), 3.14-3.06 (m, 6H), 1.30 (t, J=7.4 Hz, 9H), 0.91 (s, 9H), 0.90 (s, 9H), 0.12 (s, 3H), 0.08 (s, 3H), 0.06 (s, 3H), 0.05 (s, 3H)

Compound 240 (Rp Isomer):
$^1$H NMR (400 MHZ, CHLOROFORM-d) δ=8.54 (s, 1H), 8.38 (s, 1H), 8.33 (s, 1H), 8.01 (s, 1H), 7.39-7.09 (m, 10H), 6.39 (dd, J=2.3, 14.1 Hz, 1H), 6.13 (d, J=17.2 Hz, 1H), 5.72 (d, J=3.1 Hz, 2H), 5.68 (dd, J=4.3, 51.2 Hz, 1H), 5.43-5.29 (m, 1H), 5.10-4.96 (m, 3H), 4.90-4.83 (m, 2H), 4.78-4.72 (m, 1H), 4.52 (ddd, J=3.9, 6.6, 17.2 Hz, 1H), 4.44-4.35 (m, 2H), 4.31-4.26 (m, 1H), 4.20-4.12 (m, 2H), 3.87 (dd, J=3.5, 11.7 Hz, 1H), 3.79-3.77 (m, 1H), 3.15-3.09 (m, 6H), 1.33 (t, J=7.4 Hz, 9H), 0.94 (s, 9H), 0.89 (s, 9H), 0.13 (s, 3H), 0.12 (s, 3H), 0.10 (s, 3H), 0.09 (s, 3H)

Compound 138 (221 g, 183 mmol, 1 wt, 1 vol, 1 eq) was dissolved in a mixture of pyridine (530 ml, 6.56 mol, 519 g, 2.3 wt, 2.4 vol) and TEA (2.65 L, 19.0 mol, 1.93 kg, 8.7 wt, 12 vol, 104 eq). Triethylamine trihydrofluoride (264 ml, 1.62 mol, 262 g, 1.2 wt, 1.2 vol, 8.9 eq as complex, 27 eq HF) was added and the mixture was stirred at RT while the conversion was monitored by LCMS. After 3 h (97% conversion), methoxytrimethylsilane (TMSOMe; 1.40 L, 10.2 mol, 1.06 kg, 4.8 wt, 6.3 vol, 55 eq) was added and stirring was continued for 30 minutes. A sticky solid coated the reactor. The solution part (supernatant) was decanted off. The solid was triturated twice with toluene (2×2.2 L, 2×10 vol; supernant decanted off). The crude solid remained in the reactor was dissolved in dichloromethane (2.2 L, 10 vol) and washed with NH$_4$Cl (28 wt % solution in water; 2.2 L, 10 vol). The aqueous layer was back-extracted with dichloromethane (2.2 L, 10 vol). The combined organic layers were washed with a mixture of NaCl (36 wt % solution in water; 1.1 L, 5 vol) and water (1.1 L, 5 vol), and then concentrated under vacuum to give Compound 139 as tan dry foam (152 g, 155 mmol, 0.70 wt, 85% yield). The crude product was taken onto the next step without purification.

Stage 8

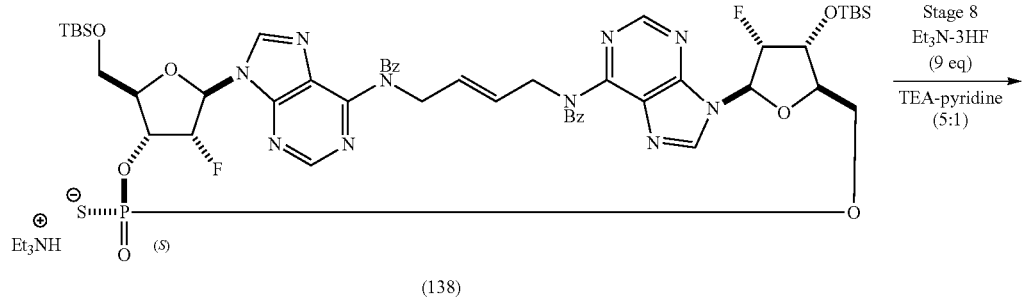

(138)

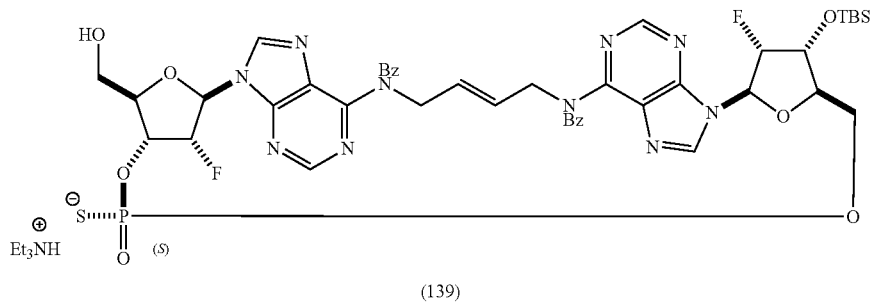

(139)

Stage 9

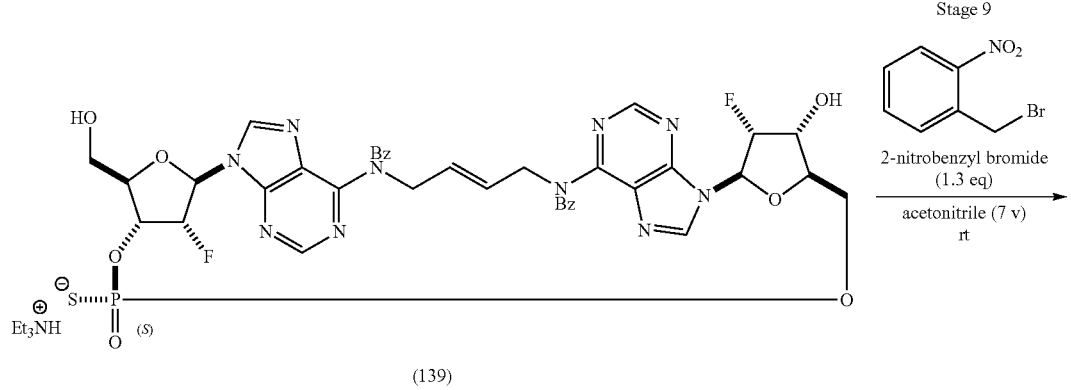

(139)

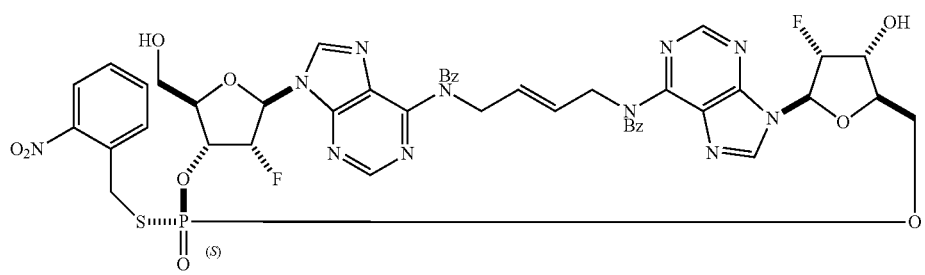

(140)

Compound 139 (150 g, 153 mmol, 1 wt, 1 vol, 1 eq) was azeotroped with acetonitrile (4 L, 27 vol) and then re-dissolved in acetonitrile (1.05 L, 0.83 kg, 5.5 wt, 7.0 vol) at rt. 2-Nitrobenzyl bromide (44.4 g, 205 mmol, 0.30 wt, 1.34 eq) was added at rt and the reaction was monitored by LCMS. After 23 h (100% conversion), EtOAc (1.50 L, 10 vol), NH$_4$Cl (28 wt % solution in water; 300 ml, 2 vol) and water (300 ml, 2 vol) were added (pH=6) and the resultant mixture was partially concentrated under vacuum at 25° C. to a weight of 1.11 kg. EtOAc (2.25 L, 15 vol) was added and the mixture was stirred for 5 minutes. The two layers were separated. The aqueous layer was extracted with ethyl acetate (750 ml, 5 vol). The combined organic layers were sequentially washed with: (1) a mixture of NaCl (36 wt % solution in water; 300 ml, 2 vol) and water (300 ml, 2 vol) and (2) water (600 ml, 4 vol). The organic layer was then concentrated under vacuum and azeotroped with n-heptane (1.50 L, 10 vol). MTBE (0.95 L, 6.3 vol) was added to the crude solid and the mixture was heated at 40° C. The mixture was diluted with EtOAc (300 ml, 2 vol) and slowly cooled to 0° C. The dense solid was allowed to settle and the supernatant was pumped off through a filter frit tube. The solid was rinsed twice with MTBE (2×300 ml, 2×2 vol, supernatant pumped off through the filter frit tube each time) and dried under vacuum at 40° C. overnight to give Compound 140 as pale yellow solid (156 g). The filtrate was concentrated under vacuum yielding a brown oil (17.8 g), which was subjected to purification via Biotage Snap-Ultra 340 g (eluents: 0 to 5% MeOH in EtOAc) to give additional Compound 140 as pale yellow solid (5.8 g). Total 156 g+5.8 g=161.8 g (net 152 mmol, 95% pure, 99% yield) $^1$H NMR (400 MHZ, CHLOROFORM-d) δ=8.46 (s, 1H), 8.15 (s, 1H), 8.10 (s, 1H), 8.09-8.06 (m, 1H), 7.89 (s, 1H), 7.54-7.51 (m, 1H), 7.49-7.45 (m, 4H), 7.37-7.28 (m, 3H), 7.24-7.19 (m, 3H), 7.16-7.11 (m, 2H), 6.22 (d, J=16.8 Hz, 1H), 6.14 (dd, J=2.7, 17.2 Hz, 1H), 5.83-5.61 (m, 3H), 5.60-5.48 (m, 1H), 5.07 (dd, J=3.5, 51.6 Hz, 1H), 5.06-4.96 (m, 1H), 4.79 (dd, J=4.9, 15.8 Hz, 1H), 4.69 (d, J=5.9 Hz, 2H), 4.67-4.56 (m, 1H), 4.48-4.40 (m, 3H), 4.37-4.30 (m, 1H), 4.27 (d, J=5.9 Hz, 2H), 4.19-4.13 (m, 1H), 3.93-3.85 (m, 1H), 3.85-3.78 (m, 1H)

Stage 10-11
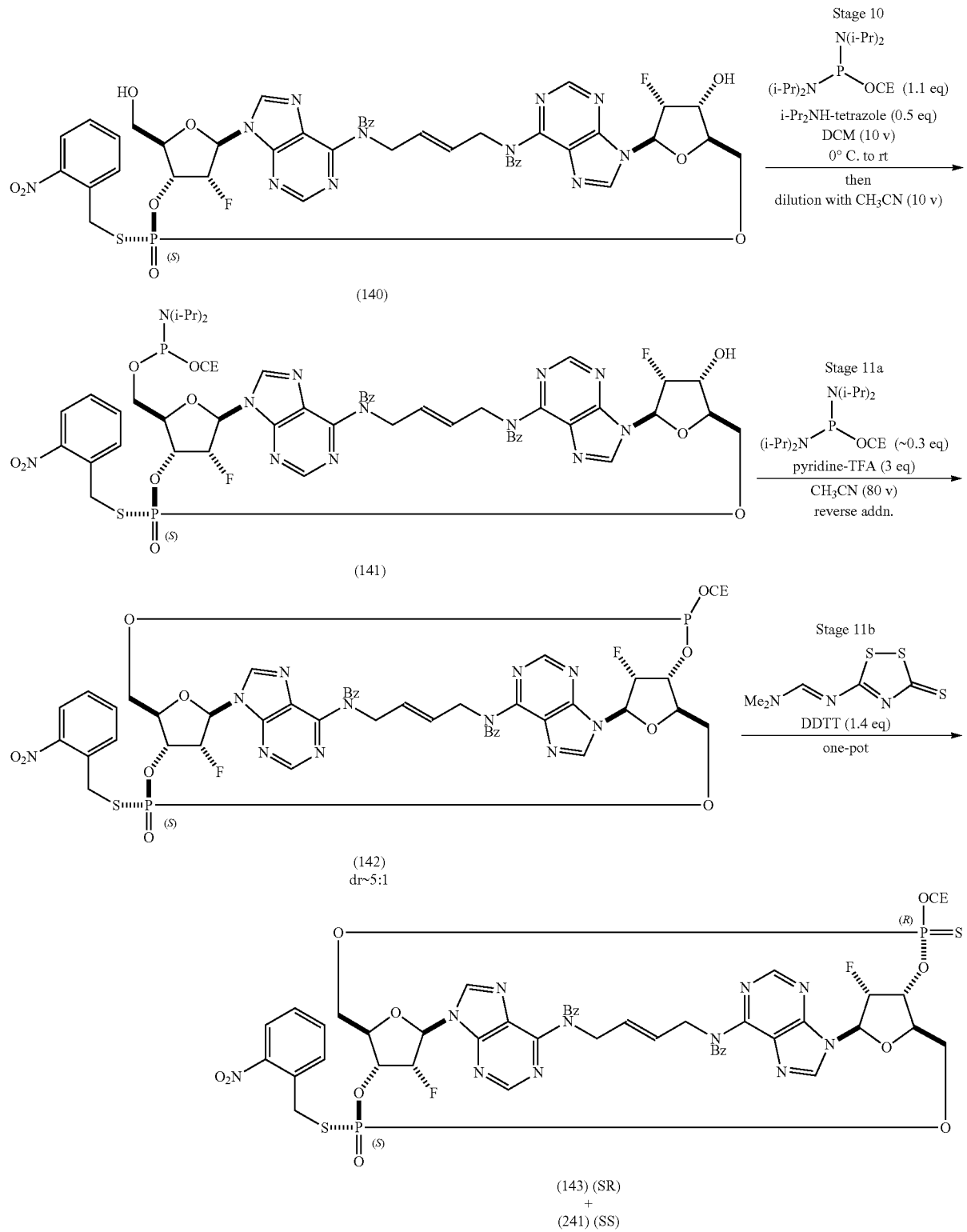
Stage 10 Compound 140 (95% pure, net 73.2 g, 72.3 mmol, 1 wt, 1 vol, 1 eq) and 2-cyanoethyl N,N,N',N'-tetraisopropylphosphorodiamidite (25.3 ml, 79.5 mmol, 0.33 wt, 0.35 vol, 1.10 eq) were azeotroped with anhydrous acetonitrile three times (3×2 L), re-dissolved in dichloromethane (0.73 L, 10 vol) and cooled to 0-5° C. Diisopropylammonium tetrazolide (6.19 g, 36.1 mmol, 0.085 wt, 0.50 eq) was added. The resulting reaction mixture was stirred at 0° C. for 10 h, warmed to 10° C. over 2 h, held at 10° C. for 10 h and warmed up to rt over 2 h. The reaction was monitored by LCMS and TLC (EtOAc with 0.5% TEA). After 18 h, anhydrous acetonitrile (0.73 L, 10 vol) was added and the mixture was stored at −20° C. over 3 days.

Stage 11a The mixture from Stage 10 was warmed to ambient temperature and added via a dropping funnel in portions (100 mL every 30 minutes, over 9 h) into a mixture of pyridine trifluoroacetate salt (azetroped in advance with pyridine twice; 41.9 g, 217 mmol, 0.57 wt, 3.0 eq) and acetonitrile (5.85 L, 80 vol). The reaction was monitored by LCMS. After 13 h, a solution of 2-cyanoethyl N,N,N',N'-tetraisopropylphosphorodiamidite (5.8 mL, 18 mmol, 0.25 eq) in acetonitrile (24 mL) was added over 4 h. Amount of the additional reagent was determined based on the remaining Compound 140 (~30% based on LCMS). More conversion of the diol was observed after 6 h.

Stage 11b ((Dimethylaminomethylidene)amino)-3H-1,2,4-dithiazoline-3-thione (DDTT; 20.8 g, 101 mmol, 0.28 wt, 1.4 eq) was added and stirring was continued for 1 h. The reaction mixture was partially concentrated to ~800 mL and diluted with MTBE (1.46 L, 20 vol), NaHCO$_3$ (9 wt % solution in water; 1.1 L, 15 vol) and water (0.37 L, 5 vol). pH=8. The layers were separated and the aqueous layer was extracted with a mixture of MTBE (1.46 L, 20 vol) and EtOAc (1.10 L, 15 vol). The combined organic layers were washed twice with 30% aq NaCl (2×0.73 L, 2×10 vol), concentrated under vacuum at 35° C. and azeotroped with toluene (1.46 L, 20 vol). LCMS and TLC (EtOAc) indicated Compound 143 (SpRp, desired): Compound 241 (SpSp) =5:1

The crude product was purified via Biotage 150M KP-Sil, (SiO$_2$ 2.5 kg; eluents: EtOAc/Hep: 2:1 (4 CV), 3:1 (2.5 CV), 4:1 (2.5 CV), 100% EA (3 CV), 5-10% MeOH in EA 4 CV) to give Compound 143 (36 g, 31.5 mmol, 44% yield).

Compound 143 (SpRp): $^1$H NMR (400 MHZ, CHLOROFORM-d) δ=8.59 (s, 1H), 8.10 (s, 1H), 8.03-7.99 (m, 1H), 7.91 (s, 1H), 7.56-7.53 (m, 2H), 7.49-7.40 (m, 5H), 7.35-7.28 (m, 2H), 7.24-7.16 (m, 4H), 6.92 (s, 1H), 6.29 (d, J=14.9 Hz, 1H), 6.08 (d, J=20.7 Hz, 1H), 5.97-5.83 (m, 1H), 5.76 (td, J=4.7, 15.6 Hz, 1H), 5.61-5.51 (m, 2H), 5.40 (d, J=4.3 Hz, 1H), 5.29-5.17 (m, 1H), 4.91 (dd, J=7.4, 14.9 Hz, 1H), 4.86-4.75 (m, 3H), 4.63 (dd, J=3.7, 9.2 Hz, 1H), 4.58-4.43 (m, 5H), 4.34-4.19 (m, 4H), 2.79 (td, J=5.9, 16.8 Hz, 1H), 2.66 (td, J=6.3, 16.8 Hz, 1H).

Compound 241 (SpSp) $^1$H NMR (400 MHZ, CHLOROFORM-d) δ=8.11 (s, 1H), 8.03 (d, J=8.2 Hz, 1H), 7.94 (s, 1H), 7.90 (s, 1H), 7.61 (s, 1H), 7.56-7.40 (m, 7H), 7.33-7.28 (m, 2H), 7.23-7.17 (m, 4H), 6.22 (d, J=17.6 Hz, 1H), 6.15 (d, J=18.8 Hz, 1H), 5.85 (dd, J=3.5, 51.2 Hz, 1H), 5.75-5.45 (m, 5H), 4.95-4.23 (m, 14H), 2.82 (t,)=6.1 Hz, 2H).

Stage 12

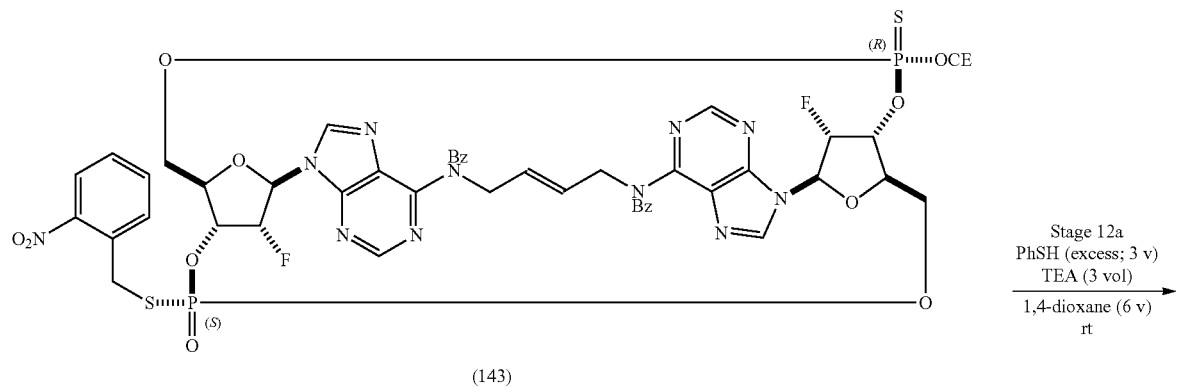

(143)

Stage 12a
PhSH (excess; 3 v)
TEA (3 vol)
1,4-dioxane (6 v)
rt

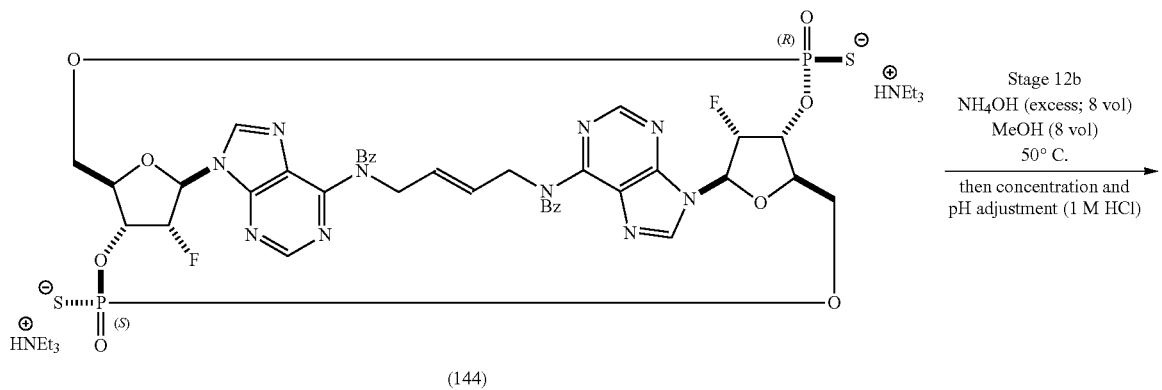

(144)

Stage 12b
NH$_4$OH (excess; 8 vol)
MeOH (8 vol)
50° C.
then concentration and pH adjustment (1 M HCl)

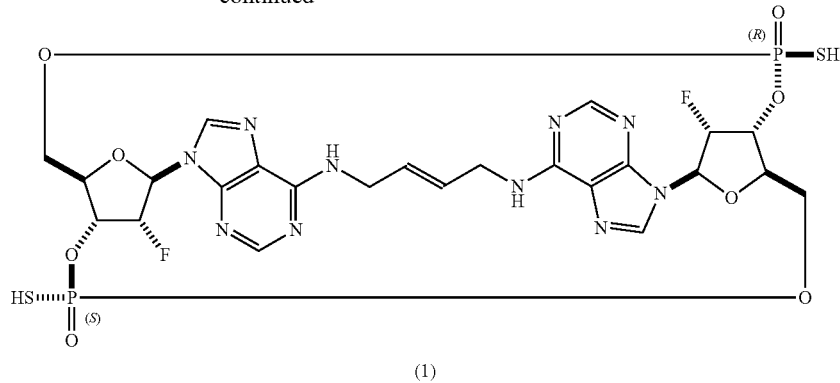

(1)

Compound 143 (71.6 g, 62.6 mmol, 1 wt, 1 vol, 1 eq) was dissolved in 1,4-dioxane (0.43 L, 6 vol). Thiophenol (215 ml, 2.09 mol, 230 g, 3.2 wt, 3 vol, >30 eq) was added followed by triethylamine (215 ml, 1.54 mol, 156 g, 2.2 wt, 3 vol). Some exotherm was observed (T-internal increased by ~7° C.), therefore, water/ice bath was used to cool and control T-internal below 27° C. The reaction was monitored by LCMS. After 2 h, MeOH (0.57 L, 8 vol) and NH₄OH (28 wt %; 15 mol, 0.57 L, 8 vol, >200 eq) were added. The resulting mixture was heated at 50° C. for 5 h, cooled to rt and stirred overnight. After 14 h, water (0.72 L, 10 vol) was added (no solid observed) and the mixture was extracted three times with 1:1 (v/v) mixture of n-heptane and toluene (3×0.86 L, 3×12 vol), followed by with toluene (0.57 L, 8 vol). The aqueous layer was concentrated in vacuo at 40-50° C. and diluted with water (1.07 L, 15 vol). The resulting slurry was kept overnight at rt. The resulting solid was filtered off, rinsing with water (0.36 L, 5 vol). The filtrate was still cloudy and filtered through celite and a Kuno filter. Cloudiness was still present. HCl (1.0 M solution in water; 132 ml, 132 mmol, 2.1 eq) was added over 1 h and pH was checked (pH <2). Stirring was continued at rt for 1 h and the mixture was filtered. The filter cake was rinsed with water (8×0.20 L), dried in a vacuum oven at 35° C. for 2 days and with no heat for 1 day to give Compound 1 as pale orange solid (44.88 g, 60.1 mmol, 0.63 wt, 96% yield).

Stage 13

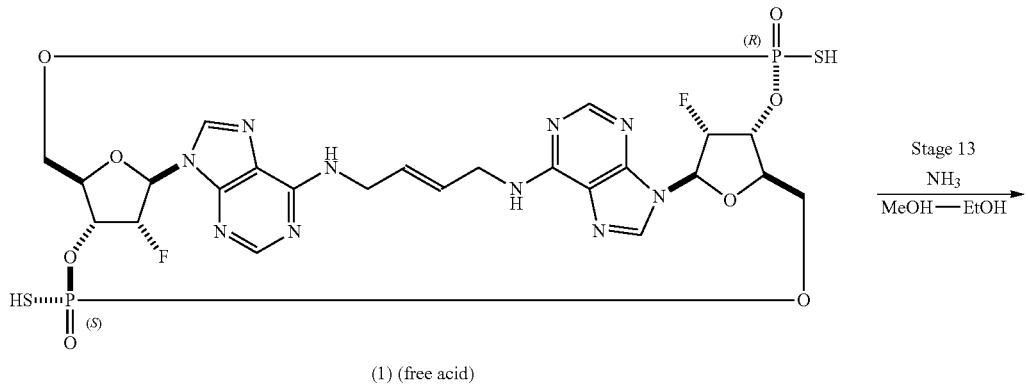

(1) (free acid)

Stage 13
NH₃
─────────
MeOH—EtOH

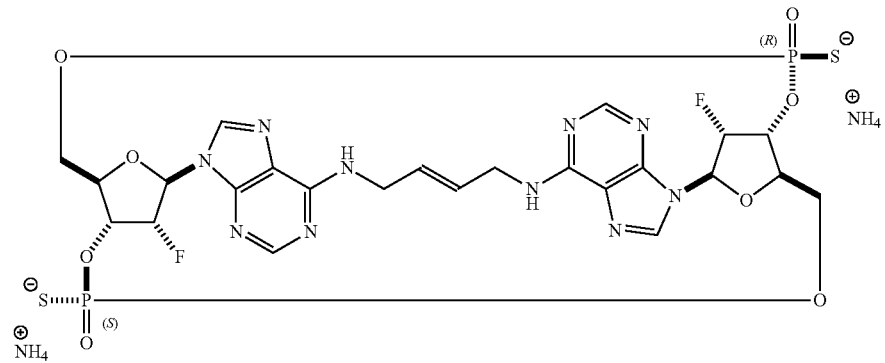

(1a) (di-ammonium salt)

To the free acid Compound 1 (22.42 g, 30.03 mmol, 1 wt, 1 vol, 1 eq) was added ammonia (2.0M solution in MeOH; 220 ml, 440 mmol, 10 vol, 15 eq). EtOH (55 ml, 2.5 vol) was added and the resulting solution was filtered through a Kuno filter (0.45 micron; PTFE), rising with 1:1 (v/v) mixture of MeOH and EtOH (90 mL, 4 vol). The filtrate was concentrate in vacuo at 30° C. yielding an off white solid, which was dried at rt overnight, grinded with a spatular (easy to break) and dried further in vacuum at rt. The isolated solid was then suspended in toluene (250 ml) and stirred at rt for 30 minutes. The solid was then collected by vacuum filtration and rinsed with toluene twice (2×50 ml). The solid was then dried under vacuum in a vacuum oven to give 22.4 g of Compound 1a (the di-ammonium salt of Compound 1).

Recrystallization: Compound 1a (22.14 g, 28.36 mmol, 1 wt, 1 vol, 1 eq) was dissolved in a mixture of water (664 ml, 30 vol) and ammonium hydroxide (28 wt %; 2.5 ml, 18 mmol, 0.63 eq) (pH=9-10) and extracted with toluene three times (3×300 ml, 3×14 vol), EtOAc three times (3×200 ml, 3×9 vol) and toluene three times (3×300 ml, 3×14 vol). The resulting aqueous layer was treated with HCl (1.0 M solution in water; 90 ml, 90 mmol, 3.2 eq) over a period of 3.5 hours (pH≤2). The mixture stirred for 30 minutes and then the solid precipitate was collected by vacuum filtration. The filter cake was washed with water three times (3×200 ml, 3×9 vol) and dried in vacuo overnight. Ammonia (2.0 M solution in MeOH; 250 ml, 500 mmol, 17.6 eq) and ethanol (100 ml) were added to the solid and the resulting mixture was concentrated in vacuo until crystals appeared (~100 ml), at which time concentration was stopped and the mixture was stirred for 20 minutes. Ethanol (45 mL) was added and the mixture was partially concentrated (45 mL removed). The same operation was repeated two more times, and then the mixture was cooled to 0° C. and stirred for 3.5 h. The white solid was collected by vacuum filtration and washed with cold ethanol (20 ml) followed by ethyl acetate (2×50 mL). The white solid was dried under vacuum at rt for 3 days to give Compound 1a as white solid (16.6 g, 21.3 mmol, 0.75 wt, 75% yield). The filtrate was concentrated under vacuum and dried under vacuum at rt for 3 days to give Compound 1a as off white solid (4.16 g, 5.3 mmol, 18% yield).

Example 1.2—$^1$H NMR Analysis of Compound 1

Figure 3:
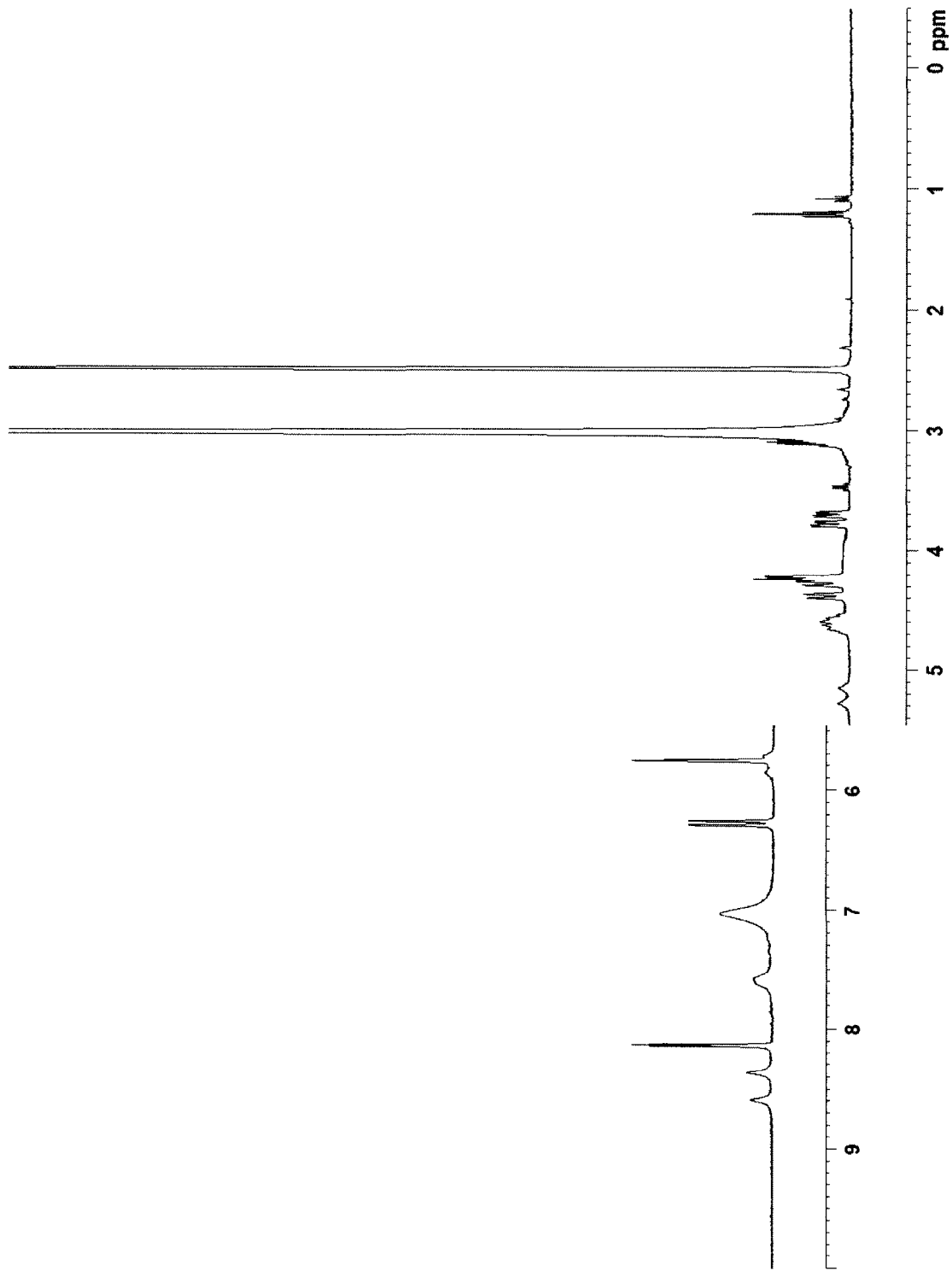
FIG. 3 shows an $^1H$ NMR spectrograph for Compound 1.

A $^1$H NMR spectrograph of Compound 1a is shown in FIG. 3. The resulting spectrum was: $^1$H-NMR Spectrum (400 MHz, DMSO-d$_6$, δ$_H$ 2.49 ppm, 80° C.) δ (ppm): 3.05-3.13 (4H, m), 3.70 (1H, dd, J=13, 5 Hz), 3.78 (1H, dd, J=12, 4 Hz), 4.21-4.24 (2H, m), 4.28 (1H, m), 4.38 (1H, m), 4.53-4.68 (2H, m), 5.22 (1H, m), 5.76 (2H, s), 5.78 (1H, m), 6.26 (1H, m), 6.29 (1H, m), 8.13 (1H, s), 8.14 (1H, s), 8.36 (1H, brs), 8.59 (1H, brs).

Example 1.3—X-Ray Analysis of Compound 1

About 2 mg of Compound 1 was dissolved in 600 uL of water. 120 uL of this solution was put in another glass vial and then this vial was stored in fixed container with 3 mL of MeCN at room temperature for 1 week. This is the H$_2$O/MeCN vapor diffusion method of sample preparation.

A colorless block single crystal (0.1×0.1×0.1 mm) found in crystallization solution was dispersed in liquid Parabar 10312 and was mounted on a Dual-Thickness Micro-Mounts™ (MiTeGen). Diffraction data was collected at −160° C. on XtaLAB PRO P200 MM007HF (Rigaku) with @ axis oscillation method using multi-layer mirror monochromated Cu-Kα radiation.

Figure 4A:
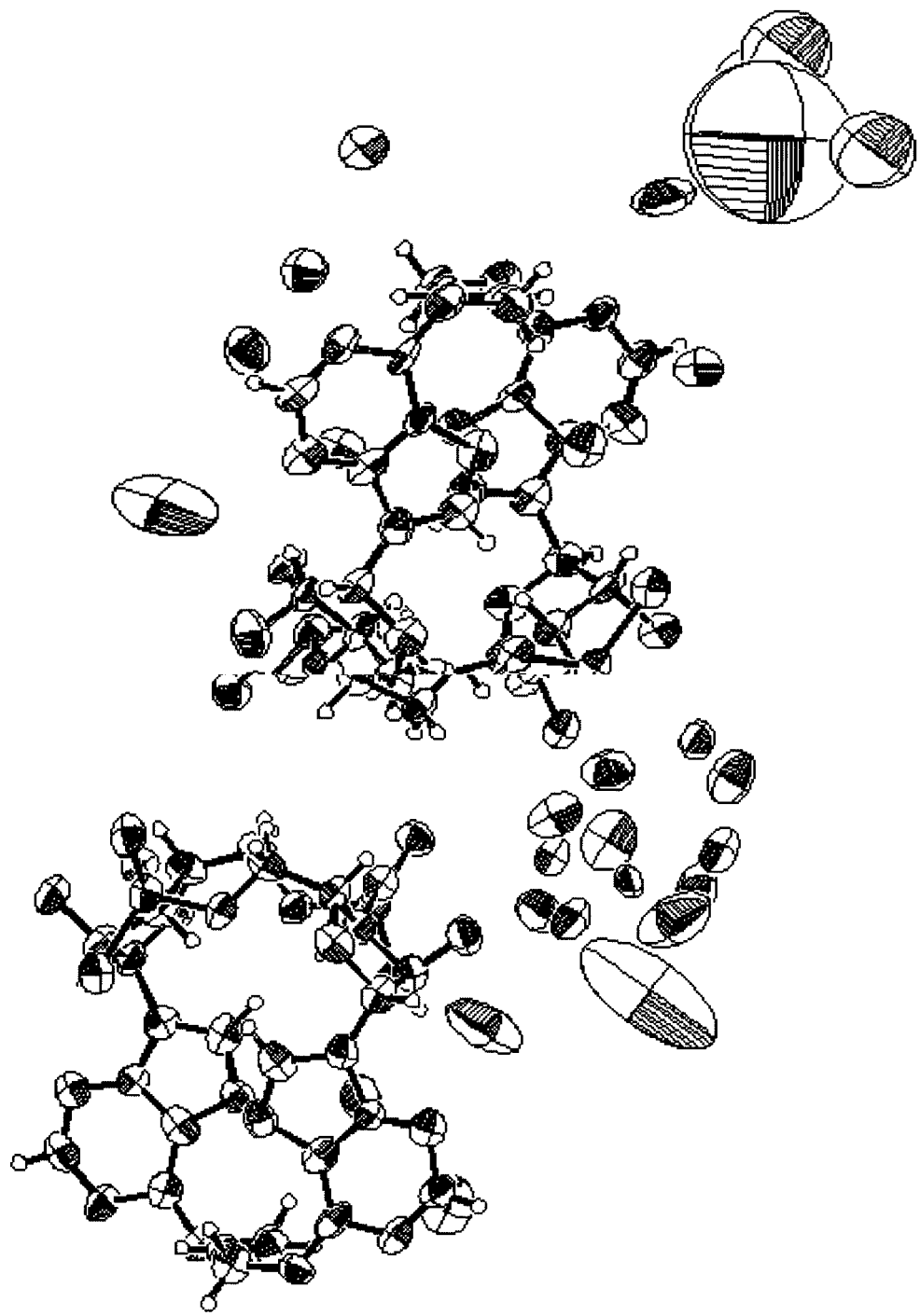
FIG. 4A, FIG. 4B, and FIG. 4C, show X-ray crystallography results (ORTEP drawings) for, respectively, an asymmetric crystal of Compound 1, a first molecule from the asymmetric crystal, and a second molecule from the asymmetric crystal.
Figure 4B:
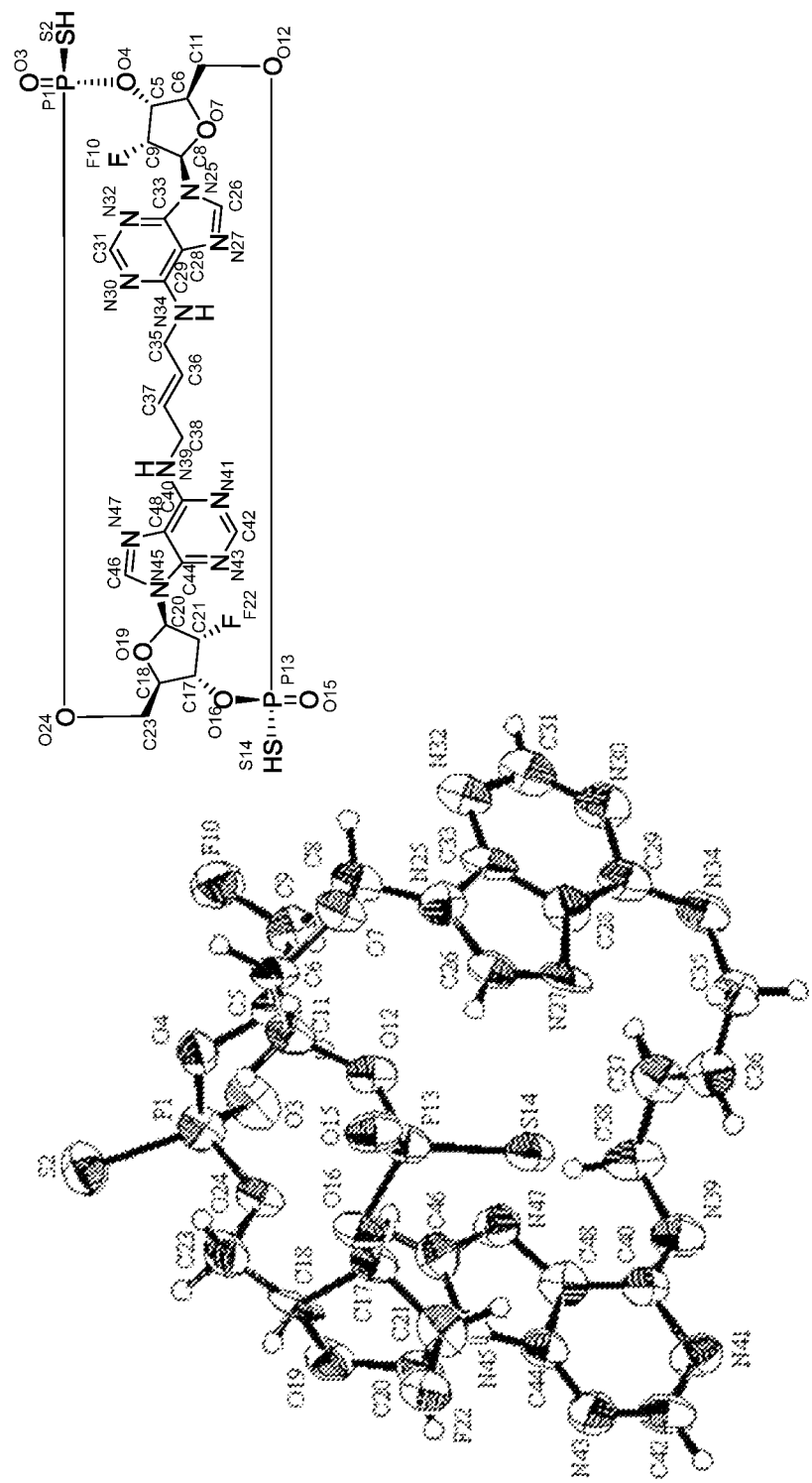
Figure 4C:
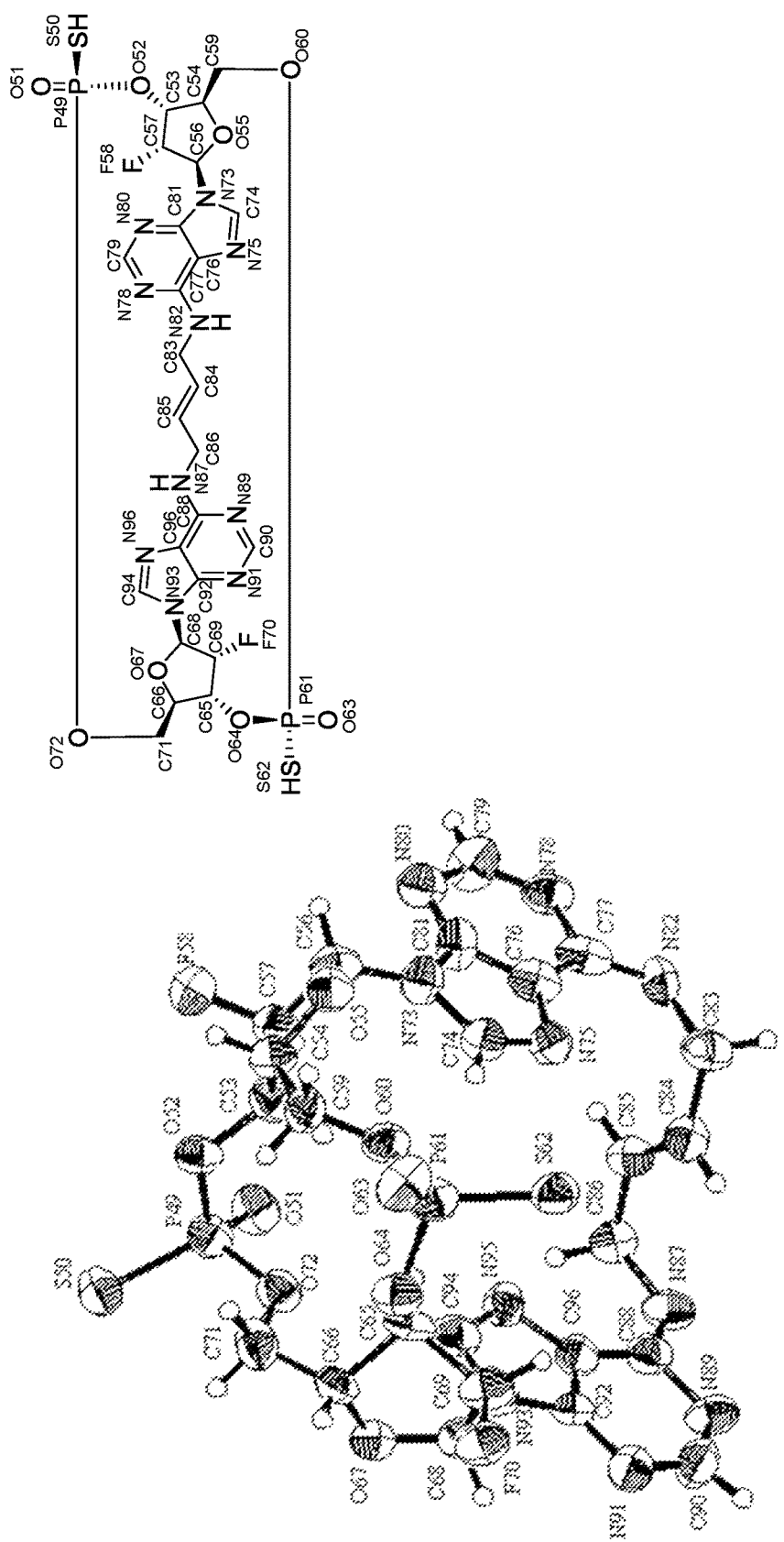

FIG. 4A shows an ORTEP figure of Compound 1 molecules in an asymmetric unit, along with a number of disordered water molecules. FIG. 4B shows the crystal structure of one of the Compound 1 molecules from FIG. 4A. FIG. 4C shows the crystal structure of the other molecule of Compound 1 shown in FIG. 4A.

The crystal structure of Compound 1 was solved with a final R-factor of 0.1354. The Flack parameter was nearly zero (0.083 (17)), indicating that the absolute configuration of Compound 1 is (R, S). The crystal structure analysis also indicated that many water molecules were present in the large channel of Compound 1, which indicated that water molecules were able to easily slip out from the channel. The analysis also confirmed that the conformations of both crystallographically independent molecules the asymmetric unit were almost the same.

Further parameters of the X-ray analysis are shown below:

| | |
|---|---|
| Temperature | 113 K |
| Wavelength | 1.54184 Å |
| Crystal system, Space group | Monoclinic, P2$_1$ |
| Lattice parameter | a = 8.1584(3) Å |
| | b = 35.451(2) Å |
| | c = 15.9146(6) Å |
| | β = 91.313(3) ° |
| Volume | 4601.7(4) Å$^3$ |
| Z value, calculated density | 4, 1.127 g/cm$^3$ |
| Crystal size | 0.1 × 0.1 × 0.1 mm |
| Total number of reflections/ | 52006/17198 |
| number of unique reflections | [R(intensity) = 0.0876] |
| Completeness | 92.2% |
| Phase determination | Direct methods (SHELXT Version 2014/5) |
| Refinement method | Full-matrix least-squares on F$^2$ (SHELXL Version 2014/7) |
| Data/parameter | 17198/1116 |
| Goodness of fit indicator | 1.545 |
| Residuals: R(I > 2σ(I)) | 0.1354 |
| Residuals: Rw | 0.3886 |
| Flack parameter | 0.083(17) |
| Maximum and Minimum peak difference | 1.17 and −0.88 e$^-$/Å$^3$ |

Example 2—X-Ray Structure Confirming Complex with WT STING

To further understand the target-binding mechanism of our new compounds, the X-ray crystal structure of WT STING in complex with the compounds was determined.

A. Expression and Purification of WT STING C-Terminal Domain (Residue 155-341)

DNA sequence encoding human WT STING protein from amino acid 155 to 341 (SEQ ID NO: 4) was cloned into the pET21b vector, following a His-TEV-Sumo tag at its N-terminus (SEQ ID NO: 5). The sequence of the pET21b has been deposited in addgene and is available here: addgene.org/vector-database/2550/; that sequence is incorporated by reference herein.

E. coli BL21 (DE3) codon plus cells were transformed with this plasmid, and the expression of recombinant protein was induced with 0.1 mM Isopropyl β-D-1-thiogalactopyranoside (IPTG). Protein was purified from the soluble fraction of cell lysate by Ni-NTA affinity chromatography. The His-TEV-Sumo tag was removed by sumo protease, and was separated from tag-free WT STING 155-341, using a second Ni-NTA affinity column. The protein was further purified by anion-exchange and size-exclusion chromatography, and was stored in buffer containing 20 mM Tris HCl pH 7.5, and 150 mM NaCl at 35 mg/ml concentration.

B. Crystallization and Structure Determination of WT STING C-Terminal Domain in Complex with Compound 1

To co-crystallize WT STING 155-341, with Compound 1, the WT STING protein was diluted to 10 mg/ml using the storage buffer (20 mM Tris HCl pH 7.5, and 150 mM NaCl) and mixed with Compound 1 (100 mM stock in DMSO) in molar ratio 1:5. The mixture was incubated for 4 hours at 4° C., and centrifuged at 13,000 rpm for 20 min before crystallization. Crystallization screen trays were set up using the hanging-drop vapor-diffusion method at 18° C. Crystals were grown by mixing 1 μL of WT STING/Compound 1 solution with an equal volume of well solution, containing 100 mM HEPES pH 7.5, 200 mM CaCl2, and 15% (wt/vol) PEG 8000. 20% (wt/vol) PEG 400 was used as cryoprotectant reagent when crystals were flash-frozen in liquid nitrogen. Diffraction datasets were collected with a Pilatus detector at SSRF BL19U1 beamline, and processed with HKL3000 and program SCALEPACK2MTZ in CCP4 software suite.

The structure of WT STING 155-341 bound to Compound 1 was determined by molecular replacement using program PHASER (Maximum Likelihood Molecular Replacement), with PDB ID 4F9E as the initial search model. The presence of Compound 1 between the dimer interface of WT STING was confirmed in a Fo-Fc difference map calculated with model phases. The model was built and completed manually with Coot program and refined with Refmac5 program in CCP4 software suite. The final refined structure was reported at a resolution of 2.38 Å in space group P212121 with unit cell measured at a=33.820, b=78.110, c=132.212, α=90.00, β=90.00, γ=90.00. Two copies of WT STING 155-341 were identified in each asymmetric unit binding to one molecule of Compound 1 at the dimer interface.

C. Interaction of Compound 1 with WT STING Observed in X-Ray Crystal Structure

Figure 5:
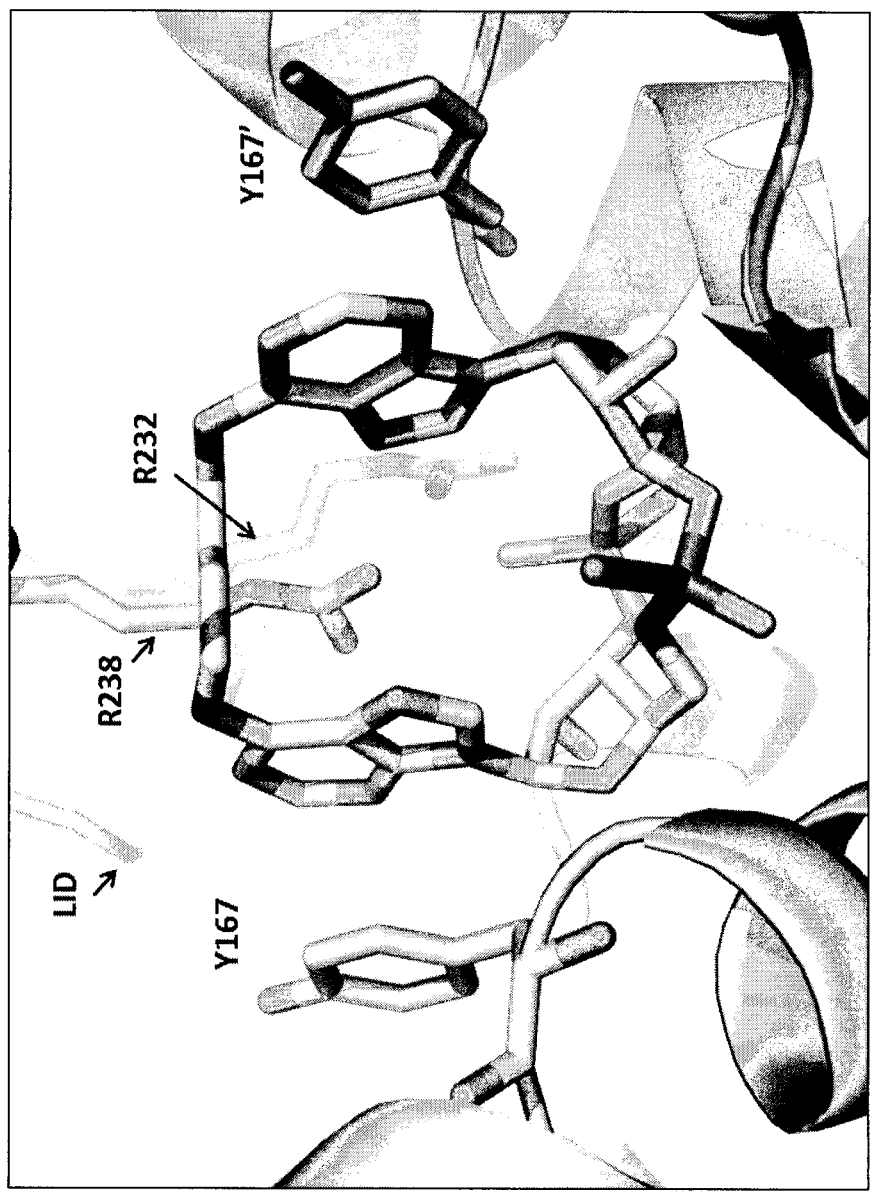
FIG. 5 shows a picture of the X-ray crystal structure of human WT STING in complex with Compound 1.

FIG. 5 shows a picture of the X-ray crystal structure of human WT STING in complex with Compound 1. We examined the X-ray crystal structure of human WT STING in complex with Compound 1, which was co-crystallized from a sample of Compound 1a. The compound binds at an interface pocket formed by a dimer of WT STING protein. The two faces of adenine base of the compound form π-π stacking interaction with Tyr240 and the guanidine group of Arg238, respectively. The trans olefin linker forms van der Waals interaction with aliphatic portion of the side chain of Arg 238. The fluorine substituent at the C2' position of ribose group of compound nests in a hydrophobic hole defined by Thr263, Pro264 and Tyr163. The negatively charged thiophosphate group of the compound forms salt bridge with Arg238 and H-bond interactions with Ser162 and Thr267, respectively. In addition, the thiophosphate group also forms electrostatic interaction with guanidine group of Arg 232. The LID loop region of WT STING, consisting of residue 226 to 243, wraps around the two base groups and the trans olefin linker.

Example 3—Determination of X-Ray Crystal Structure of REF STING in Complex with Compound 1

A. Expression and Purification of REF STING C-Terminal Domain (Residue 155-341, SEQ ID NO: 6)

DNA sequence encoding human REF STING protein from amino acid 155 to 341 (SEQ ID NO: 6) was cloned into the pET21b vector, following a His-TEV-Sumo tag at its N-terminus (SEQ ID NO: 7). The sequence of the pET21b has been deposited in addgene and is available here: addgene.org/vector-database/2550/; that sequence is incorporated by reference herein.

*E. coli* BL21 (DE3) codon plus cells were transformed with this plasmid, and the expression of recombinant protein was induced with 0.1 mM Isopropyl β-D-1-thiogalactopyranoside (IPTG). Protein was purified from the soluble fraction of cell lysate by Ni-NTA affinity chromatography. The His-TEV-Sumo tag was removed by sumo protease, and was separated from tag-free REF STING_155-341 using a second Ni-NTA affinity column. The protein was further purified by anion-exchange and size-exclusion chromatography, and was stored in buffer containing 20 mM Tris HCl pH 7.5, and 150 mM NaCl at 24 mg/ml concentration.

B. Crystallization and Structure Determination of REF STING C-Terminal Domain in Complex with Compound 1

To co-crystallize REF STING_155-341 with Compound 1, REF STING protein was diluted to 10 mg/ml using the storage buffer (20 mM Tris HCl pH 7.5, and 150 mM NaCl) and mixed with Compound 1 (100 mM stock in DMSO) in molar ratio 1:5. The mixture was incubated for 4 hours at 4° C., and centrifuged at 13,000 rpm for 20 min before crystallization. Crystallization screen trays were set up using the hanging-drop vapor-diffusion method at 18° C. Crystals were grown by mixing 1 μL of REF STING/Compound 1 solution with an equal volume of well solution, containing 100 mM HEPES pH 7.5, 200 mM CaCl2, and 15% (wt/vol) PEG 8000. 20% (wt/vol) PEG 400 was used as cryoprotectant reagent when crystals were flash-frozen in liquid nitrogen. Diffraction datasets were collected with a Pilatus detector at SSRF BL18U1 beamline, and processed with HKL3000 and program SCALEPACK2MTZ in CCP4 software suite. This structure is shown in FIG. 6.

The structure of REF STING_155-341, bound to Compound 1 was determined by molecular replacement using program PHASER (Maximum Likelihood Molecular Replacement), using previously determined WT STING 155-341 structure (as described above) as the initial search model. The presence of Compound 1 between the dimer interface of REF STING, was confirmed in a Fo-Fc difference map calculated with model phases. The model was built and completed manually with Coot program and refined with Refmac5 program in CCP4 software suite. The final refined structure was reported at a resolution of 2.76 Å in space group P212121 with unit cell measured at a=33.733, b=77.831, c=131.689, α=90.00, β=90.00, γ=90.00. Two copies of REF STING 155-341 were identified in each asymmetric unit binding to one molecule of Compound 1 at the dimer interface.

C. Interaction of Compound 1 with REF STING Observed in X-Ray Crystal Structure

Figure 6:
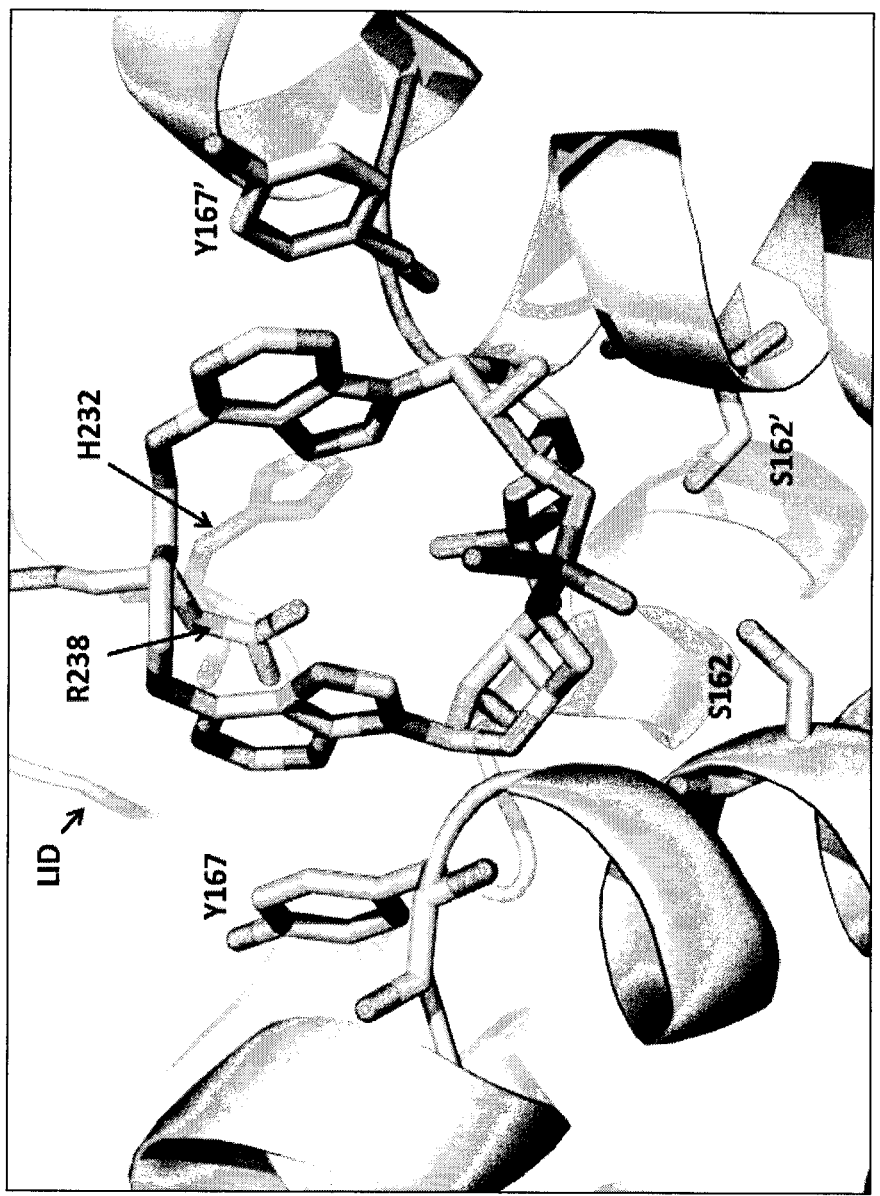
FIG. 6 shows human REF STING C-terminal Domain in complex with Compound 1.

FIG. 6 shows the X-ray crystal structure of human REF STING in complex with Compound 1, which was co-crystallized from a sample of Compound 1a. The compound binds at an interface pocket formed by a dimer of STING protein. The two faces of adenine base of the compound form π-π stacking interaction with Tyr240 and the guanidine group of Arg238, respectively. The trans olefin linker forms van der Waals interaction with the aliphatic portion of the side chain of Arg238 while the guanidine portion of the side chain of Arg238 forms π-π stacking interaction with the imidazole group of the side chain of His232 from outside. The olefin linker is in contact with the interacting pair of the side chains of Arg238 and His232. The fluorine substituent at the C2' position of ribose group of compound nests in a hydrophobic hole defined by Thr263, Pro264 and Tyr163.

The negatively charged thiophosphate group of the compound forms salt bridge with Arg238 and H-bond interactions with Ser162 and Thr267, respectively. The LID loop region of REF STING, consisting of residue 226 to 243, wraps around the two base groups and the trans olefin linker.

Example 4—In Vivo Evaluation of Compound 1a in a Murine Bladder Cancer Model Using Intravesicular Administration Route MBT-2 murine bladder cancer orthotopic model was established and characterized by Lee, et al., ("Tumor Establishment Features of Orthotopic Murine Bladder Cancer Models," *Urological Oncology* 2012; 53:396-400) in 2012 and showed a similar histology as the human bladder cancer. Hence, this model was chosen to evaluate Compound 1's anti-bladder cancer activity. The protocol with HCl pretreatment procedure described by Lee, et al. was applied to establish the model. In brief, 30 µL 0.1 N HCl solution was injected into mouse bladder through a catheter and HCl solution was allowed to remain in the bladder for 15 seconds. Then the HCl solution was replaced by 30 µL 0.1 N NaOH solution followed by one flushing step with 1× PBS (pH7.4). The follow-up tumor cell implantation procedure was modified from the original literature. In brief, after a flushing step, MBT-2 tumor cells (2×106 cells in 50 µL RPMI1640 medium) were instilled into the bladder and allowed to remain for 45 minutes. At the end of this 45 minute period, the bladder was drained.

Three days after tumor cells implantation, mice were treated with varied doses of Compound 1a, BCG (OncoTICE®, Merck Canada Inc.), anti-mouse PD-1 antibody (clone #RMP1-14, Bioxcell), and a combination of Compound 1a and PD-1 antibody with the schedule summarized in Table 1. Both Compound 1a and BCG were administered through an intravesicular route, while PD1 antibody was through intraperitoneal injection.

On each day of dosing BCG was diluted in NaCl 0.9% (Lavoisier, France) to reach the final concentration of 16.875 mg/mL for dosing. Any leftover dosing solution was discarded after use. For anti-PD-1 antibody, 1× PBS (Lonza, France) was used to dilute the stock solution to prepare 1 mg/mL working solution for dosing. For Compound 1a, a 10 mg/mL stock solution was first prepared by dissolving dried powder in 1× PBS. Then varied concentrations of Compound 1a, including 5 mg/mL (400 µg/mouse group), 2.5 mg/ml (200 µg/mouse group) and 1.25 mg/mL (100 µg/mouse group) were prepared by further dilution of the stock solution with 1× PBS.

TABLE 1

Treatment agents and dosing schedule schemes

| Group | No animals | Treatment | Dose | Inj. route | Treatment schedule |
|---|---|---|---|---|---|
| 1 | 10 | Vehicle | — | IVe[1] | Q7D×3 |
| 2 | 10 | BCG | 1.35 mg/mouse | IVe | Q7D×3 |
| 3 | 10 | PD1 antibody | 10 mg/kg/inj | IP [2] | TW×2 |
| 4 | 10 | Compound 1a | 100 µg/mouse | IVe | Q7D×3 |
| 5 | 10 | Compound 1a | 200 µg /mouse | IVe | Q7D×3 |
| 6 | 10 | Compound 1a | 400 µg /mouse | IVe | Q7D×3 |
| 7 | 10 | Compound 1a PD1 antibody | 400 µg /mouse 10 mg/kg/inj | IVe IP | Q7D×3 TW×2 |

[1]IVe, Intravesical installation
[2] IP, Intraperitoneal injection

Figure 7:
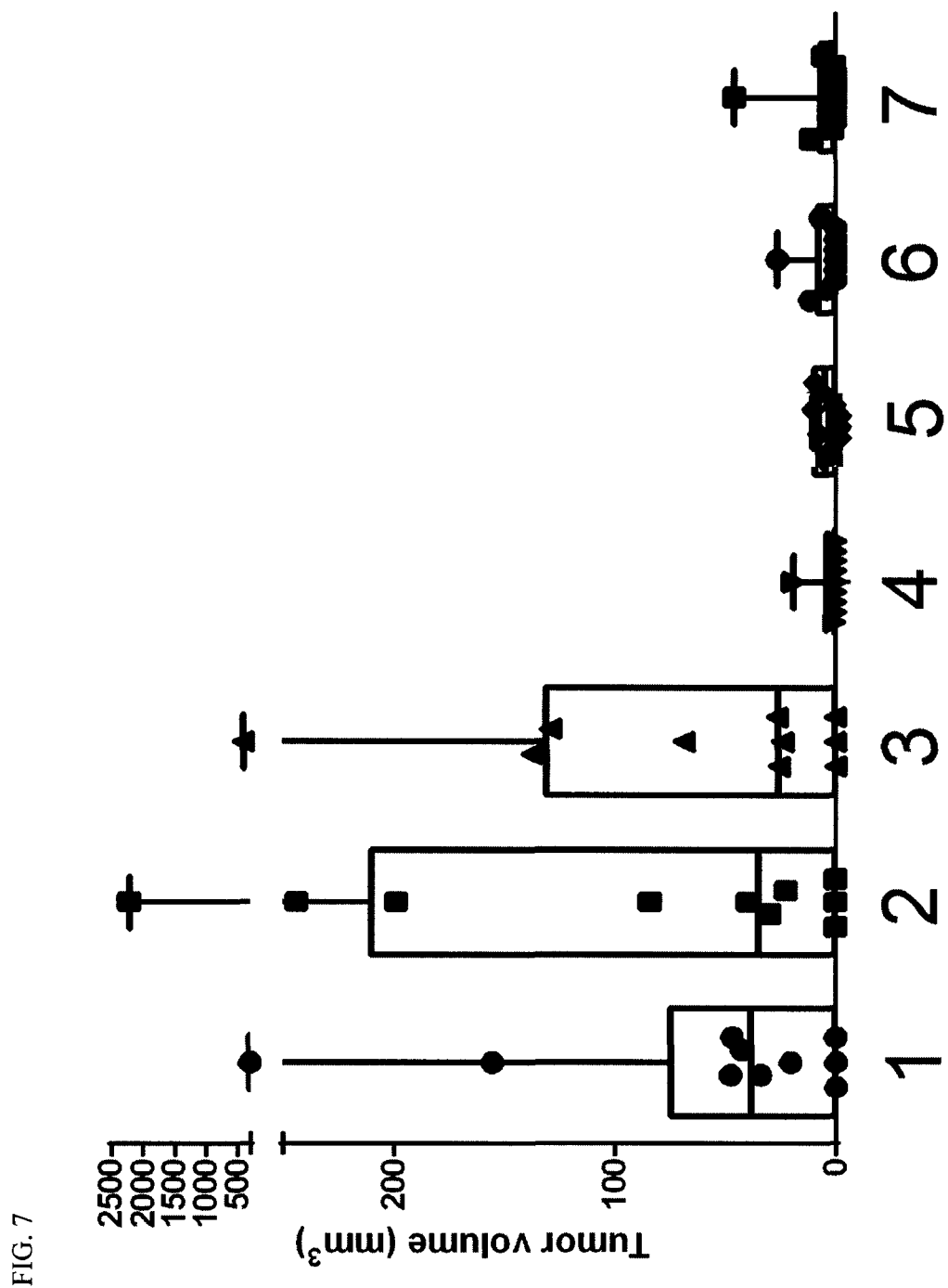
FIG. 7 shows tumor volumes quantified by MRI from days 20-21.

From days 20-21, tumor growth in bladder was quantitated by MRI (Magnetic resonance imaging) and tumor sizes of all mice were graphed as shown in FIG. 7. FIG. 7 shows tumor volume quantitation by MRI from days 20-21 of all study animals. As shown in FIG. 7, all Compound 1a treated groups (Group 4 to 7) showed much smaller tumor volumes than vehicle group (Group 1), BCG group (Group 2) and PD1 antibody group (Group 3).

Figure 8:
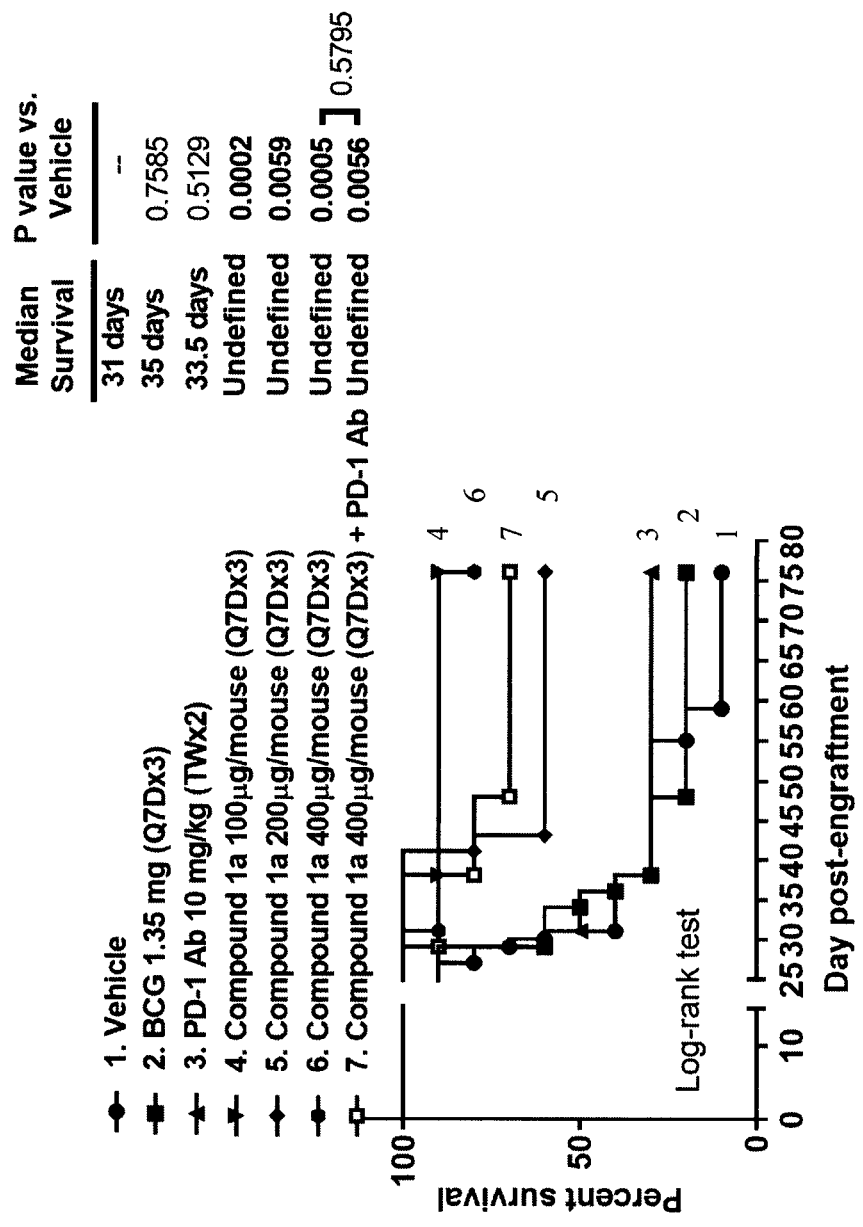
FIG. 8 show survival curves for all groups in bladder cancer treatment Example 4.

Compound 1a also showed a statistically significant survival benefit relative to vehicle treated animals as shown in FIG. 8.

Both BCG and anti-PD1 antibody failed to show significant anti-cancer activity in this orthotopic mouse bladder cancer model, suggesting that the model used is a BCG/PD1 antibody resistant/refractory model.

Example 103—HAQ STING Agonist Activity Reporter Assay

THP1-Dual™ Cells (InvivoGen, Cat #thpd-nfis) were applied for $EC_{50}$ determination. THP1 Dual™ Cells have been characterized to carry the HAQ STING genotype by the vendor Invivogen (Insight 201402-1). Cells were grown and maintained under conditions as recommended by manufacturer. The interferon regulatory factor (IRF) pathway induction described in manufacturer's manual was followed for $EC_{50}$ determination. In brief, cells were seeded and treated with different concentrations of compound for 20 hrs while incubated at 37° C., 5% $CO_2$. Cells were resuspended and QUANTI-Luc™ solution (Cat. #: rep-qlc1) was added. Resulting light emission was measured by luminometer (Envision, Perkin Elmer). Obtained signals were plotted and $EC_{50}$ was calculated with GraphPad Prism7 software.

Figure 9:
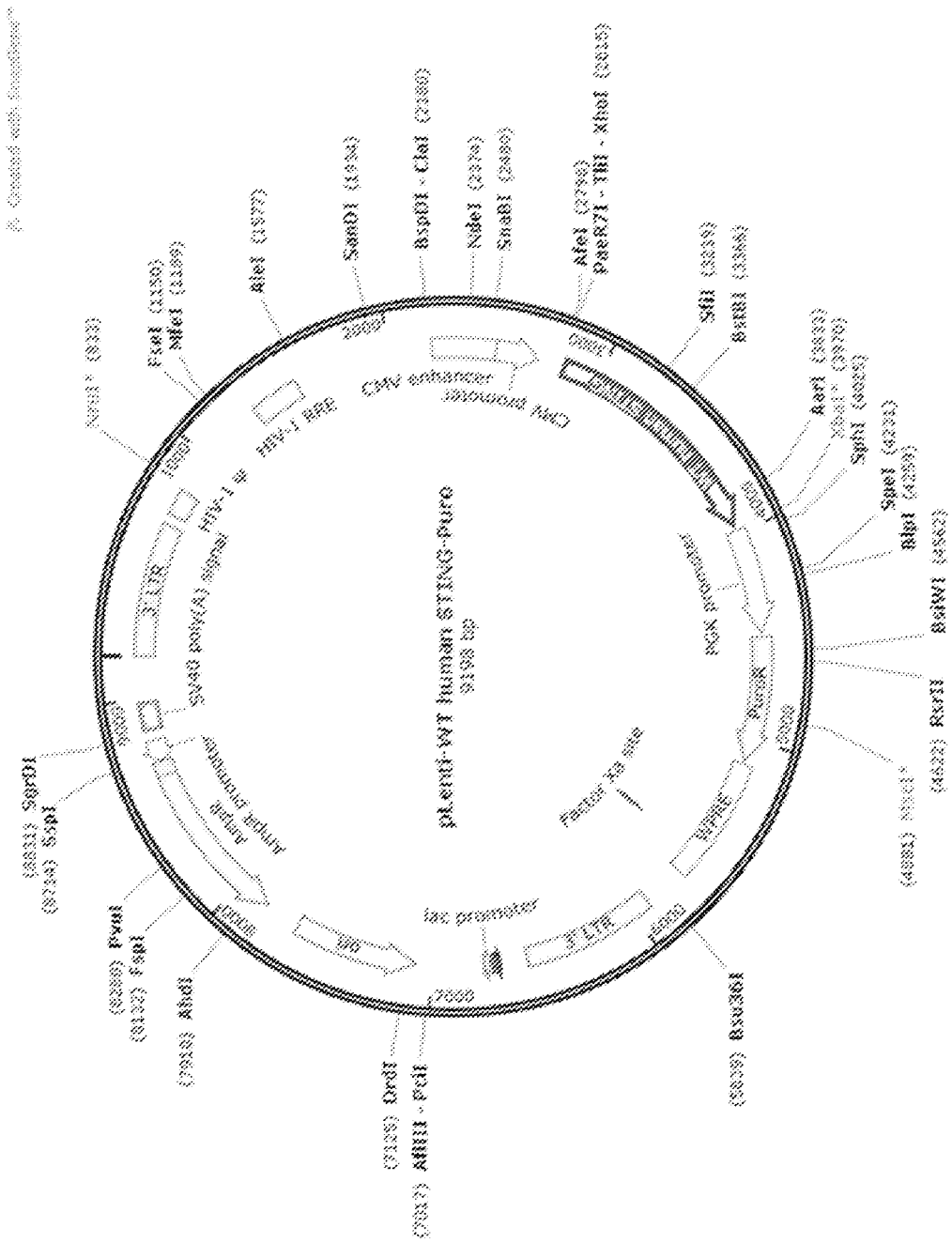
FIG. 9 shows an expression vector map for WT STING (pLenti-WT human STING-Puro)

Human STING $EC_{50}$ (µM) values for Compound 1a are reported in Table 2, below Example 104—STING Variant Specific Reporter Assay Human STING has 4 major variants, including WT, HAQ, REF, and AQ variants. REF-STING, also referred to as R232H, for example, occurs in about 14% of the human population. Compared to the wild-type allele, R232H has decreased response to bacterial and metazoan cyclic dinucleotides. Details of these 4 major variants as well as other rare variants are reported by Yi G, et al., "Single nucleotide polymorphisms of human STING can affect innate immune response to cyclic dinucleotides" *PLoS One* 2013; 8: e77846. STING variant specific reporter cell lines were established by using THP1-Dual™ KO-STING cells (InvivoGen, Cat #thpd-kostg) and three STING variant protein expression vectors. The expression vector map for WT STING is shown in FIG. 9. For the other two expression vectors, different STING variant sequences were used in that vector, with the WT STING replaced by the appropriate nucleotide sequence.

STING variant-expressing vectors for WT-STING, REF-STING, and AQ-STING were prepared and stably transfected into THP1-Dual™ KO-STING cells to prepare STING variant-specific reporter assays for WT-STING, REF-STING and AQ-STING, respectively. $EC_{50}$ values were determined as described above in Example 103 for the HAQ STING agonist activity reporter assay. Results are shown below in Table 2, below. The DNA sequences used for these STING variants are shown in SEQ ID NO: 1 (Nucleotide Sequence of WT Human STING), SEQ ID NO: 2 (Nucleotide Sequence of REF Human STING), and SEQ ID NO: 3 (Nucleotide Sequence of AQ Human Sting)

WT Human STING:

(SEQ ID NO: 1)
atgccccactccagcctgcatccatccatcccgtgtcccaggggtcacggggcccagaaggcagccttggttctgctgagtgcctgcc tggtgacccctttgggggctaggagagccaccagagcacactctccggtacctggtgctccacctagcctccctgcagctgggactgct gttaaacggggtctgcagcctggctgaggagctgcgccacatccactccaggtaccggggcagctactggaggactgtgcgggcct gcctgggctgcccctccgccgtggggccctgttgctgctgtccatctatttctactaccctcccaaatgcggtcggcccgcccttca cttggatgcttgccctcctgggcctctcgcaggcactgaacatcctcctgggcctcaagggcctggccccagctgagatctctgcagtg tgtgaaaagggaatttcaacgtggcccatgggctggcatggtcatattacatcggatatctgcggctgatcctgccagagctccaggc ccggattcgaacttacaatcagcattacaacaacctgctacggggtgcagtgagccagcggctgtatattctcctcccattggactgtgg ggtgcctgataacctgagtatggctgaccccaacattcgcttcctggataaactgccccagcagaccggtgaccgggctggcatcaag gatcgggtttacagcaacagcatctatgagcttctggagaacgggcagcgggggcacctgtgtcctggagtacgccaccccttg cagactttgtttgccatgtcacaatacagtcaagctggctttagccggaggataggcttgagcaggccaaactcttctgccggacactt gaggacatcctggcagatgcccctgagtctcagaacaactgccgcctcattgcctaccaggaacctgcagatgacagcagcttctcgc tgtcccaggaggttctccggcacctgcggcaggaggaaaaggaagaggttactgtgggcagcttgaagacctcagcggtgcccagt acctccacgatgtcccaagagcctgagctcctcatcagtggaatggaaaagcccctccctctccgcacggatttctcttga.

REF Human STING:

(SEQ ID NO: 2)
atgccccactccagcctgcatccatccatcccgtgtcccaggggtcacggggcccagaaggcagccttggttctgctgagt gcctgcctggtgacccctttgggggctaggagagccaccagagcacactctccggtacctggtgctccacctagcctccctgcagctg ggactgctgttaaacggggtctgcagcctggctgaggagctgcgccacatccactccaggtaccggggcagctactggaggactgt gcgggcctgcctgggctgcccctccgccgtggggccctgttgctgctgtccatctatttctactaccctcccaaatgcggtcggcc cgcccttcacttggatgcttgccctcctgggcctctcgcaggcactgaacatcctcctgggcctcaagggcctggccccagctgagat ctctgcagtgtgtgaaaagggaatttcaacgtggcccatgggctggcatggtcatattacatcggatatctgcggctgatcctgccaga gctccaggcccggattcgaacttacaatcagcattacaacaacctgctacggggtgcagtgagccagcggctgtatattctcctcccatt ggactgtggggtgcctgataacctgagtatggctgaccccaacattcgcttcctggataaactgccccagcagaccggtgaccatgct ggcatcaaggatcgggtttacagcaacagcatctatgagcttctggagaacgggcagcgggggcacctgtgtcctggagtacgc cacccccttgcagactttgtttgccatgtcacaatacagtcaagctggctttagccggaggataggcttgagcaggccaaactcttctg ccggacacttgaggacatcctggcagatgcccctgagtctcagaacaactgccgcctcattgcctaccaggaacctgcagatgacag cagcttctcgctgtcccaggaggttctccggcacctgcggcaggaggaaaaggaagaggttactgtgggcagcttgaagacctcagc ggtgcccagtacctccacgatgtcccaagagcctgagctcctcatcagtggaatggaaaagcccctccctctccgcacggatttctctt ga AQ Human STING:

(SEQ ID NO: 3)
atgccccactccagcctgcatccatccatcccgtgtcccaggggtcacggggcccagaaggcagccttggttctgctgagt gcctgcctggtgacccctttgggggctaggagagccaccagagcacactctccggtacctggtgctccacctagcctccctgcagctg ggactgctgttaaacggggtctgcagcctggctgaggagctgcgccacatccactccaggtaccggggcagctactggaggactgt gcgggcctgcctgggctgcccctccgccgtggggccctgttgctgctgtccatctatttctactaccctcccaaatgcggtcggcc cgcccttcacttggatgcttgccctcctgggcctctcgcaggcactgaacatcctcctgggcctcaagggcctggccccagctgagat ctctgcagtgtgtgaaaagggaatttcaacgtggcccatgggctggcatggtcatattacatcggatatctgcggctgatcctgccaga gctccaggcccggattcgaacttacaatcagcattacaacaacctgctacggggtgcagtgagccagcggctgtatattctcctcccatt

```
-continued
ggactgtggggtgcctgataacctgagtatggctgaccccaacattcgcttcctggataaactgcccagcagaccgctgaccgagct ggcatcaaggatcgggtttacagcaacagcatctatgagcttctggagaacgggcagcgggggcacctgtgtcctggagtacgc cacccccttgcagactttgtttgccatgtcacaatacagtcaagctggctttagccgggaggataggcttgagcaggccaaactcttctg ccagacacttgaggacatcctggcagatgccctgagtctcagaacaactgccgcctcattgcctaccaggaacctgcagatgacag cagcttctcgctgtcccaggaggttctccggcacctgcggcaggaggaaaaggaagaggttactgtgggcagcttgaagacctcagc ggtgcccagtacctccacgatgtcccaagagcctgagctcctcatcagtggaatggaaaagcccctccctctccgcacggatttctctt ga
```

Example 105—Mouse STING Agonist Activity Reporter Assay

RAW-Lucia™ ISG Cells (InvivoGen, Cat #rawl-isg) were used for a mouse STING agonist reporter assay. $EC_{50}$ values were determined as described above in Example 103 in the HAQ STING agonist activity reporter assay. Results are shown below in Table 2.

Example 106—Differential Scanning Fluorimetry (DSF) Assay

A DSF assay was employed to measure the physical interaction between compounds and recombinant STING protein. Truncated recombinant STING protein (a.a.155-341) (SEQ ID NO: 4) was expressed in *E. coli* and isolated for the assay, as described below. Assay matrix was prepared in 384-well plates to a final volume of 10 μL per well consisting of 1 μM recombinant STING protein (a.a. 155-341) (SEQ ID NO: 4), 100 mM PBS pH 7.4, supplemented with 100 mM KCl, 5X SYPRO orange dye and 50 μM compound (final DMSO conc. 0-1%). Assays were performed on a QuantStudio 12K Flex Real-Time PCR System using a temperature gradient from 25° C. to 95° C. at a rate of 0.05° C./min, and excitation and emission filters at 470 and 586 nm, respectively. According to the fluorescence derivative curves assigned by the Applied Biosystems® Protein Thermal Shift software (algorithm version 1.3), the thermal melt (Tm) of the unbound and ligand bound recombinant STING protein and the difference in thermal melt (dTm D) was calculated.

In general, compounds with ΔTm values larger than 0 are considered to have a physical interaction with the tested protein, and the value of ΔTm is positively associated with compound binding affinity. Here, Compound 1a showed the ΔTm of 17.6 (Table 2), indicating physical interaction with STING protein.

TABLE 2

Compound 1a in vitro characterization

| Compound | Human STING $EC_{50}$ (μM) | | | | Mouse STING $EC_{50}$ (μM) | DSF WT STING ΔTm (° C.) |
|---|---|---|---|---|---|---|
| | WT | HAQ | REF | AQ | | |
| 1a | 0.9 | 4.1 | 4.8 | 1.2 | 3.4 | 17.6 |

Example 107—Ex Vivo Human PBMC Stimulation Assay

Human blood from 5 healthy donors was collected using 10.0 mL BD Vacutainer Sodium heparin tubes (cat #367874). Peripheral blood mononuclear cell (PBMC) isolation was done using SIGMA ACCUSPIN 50 ml Tubes (cat #A2055) and sigma ACCUSPIN System-HISTOPAQUE-1077 (cat #A7054) using protocol provided by manufacturer. PBMC layer was harvested and washed with 1x Phosphate Buffered Saline (PBS) as suggested by Sigma. PBMC were counted and finally suspended @ 1×10e6/ml in RPMI (corning cat #10-041-CV) supplemented with 10% fetal bovine serum (FBS) (Gibco cat #20140.79). 1 ml of cell (1×10e6) were transferred into Falcon 5 mL. Round Bottom Polypropylene Test Tube (cat #352063) and stimulated with different concentrations (0, 0.1, 1, 10 μM) for 24 hours in 5% $CO_2$ incubator at 37° C.

After 24 hours of incubation the tubes were centrifuged at 1400 rpm for 5 minutes and supernatants were harvested. Supernatant were stored in −80° C. for subsequent IFNβ measurement. IFNβ measurement was done using Human IFN-β Base Kit (Meso Scale Diagnostics cat #K151ADA) and protocol provided by manufacturer was used. IFN-beta estimation was done by reading assay plate at MESO SECTOR Imager 2400 and using MSD Discovery Workbench 4.0 program. After 24 hours IFNβ protein was analyzed. The results showed that Compound 1a can induce primary human PBMC IFNβ protein production in a dose-dependent manner.

Results shown in Table 3 reflect an average of measurements conducted using five different donors.

TABLE 3

Ex vivo human PBMC stimulation assay

| | PBS (Control) | Compound 1a | | |
|---|---|---|---|---|
| | | 0.1 μM | 1 μM | 10 μM |
| IFNβ (pg/mL) | 0 | 21.3 ± 17.8 | 227.5 ± 62.4 | 540.2 ± 215.0 |

For IFNβ mRNA quantification, total RNA was isolated using the RNeasy Mini Kit (Qiagen, Germany) according to the manufacturer's protocol. IFNβ mRNA was quantified by qPCR assay. In brief, total RNA (400 ng to 1000 ng) was converted to cDNA in a 60-μl reaction volume using SuperScript VILO MasterMix (Life Technologies, USA). Obtained CDNAs (10 ng) were subsequently amplified using Applied Biosystems TaqMan expression assays using RNA-specific primers for IFNB1 (Hs01077958_s1), and GAPDH (Hs99999905_m1). A qPCR analysis was performed with TaqMan Fast Advanced Master Mix (Life Technologies, USA) on the Applied Biosystems Quantstudio 12K Flex Real-Time PCR System, with an initial 2-min step at 50° C. followed by 95° C. for 2 s and 40 cycles of 95° C. for 1 s and 60° C. for 20 s. Relative gene expression was calculated after normalization against the reference gene GAPDH using the 2-ΔΔCT method. Calculations were done using the Applied Biosystems Quantstudio 12K Flex software v1.2.2. IFNβ mRNA fold changes vs. vehicle treated samples are summarized in Table 4. The results showed that Compound 1a can induce IFNβ mRNA in primary PBMC in a dose- and time-dependent manner. Table 4 shows an average calculated from five different donors.

TABLE 4

Ex vivo human PBMC 3-hr & 24-hr stimulation assay (mRNA)

| IFNβ mRNA (fold changes vs. vehicle treated samples) | Compound 1a | | |
|---|---|---|---|
| | 0.1 μM | 1 μM | 10 μM |
| 3-hr treatment | 51.0 ± 21.7 | 219.8 ± 69.8 | 1973.3 ± 1023.0 |
| 24-hr treatment | 28.1 ± 28.9 | 10652.3 ± 4992.4 | 24157.3 ± 9224.2 |

Example 108—Anti-Cancer Effect of Compound 1a on the CT26 Dual Tumor Model

Compound 1a was tested for its anti-cancer activity in CT26 dual tumor model, which is a mouse colon cancer model. Female of 5-6 week old Balb/cJ mice (Jackson Labs, Bar Harbor, Maine) were implanted subcutaneously with CT26 tumor cells on both sides of each animals, $10^5$ cells for each side. For study A, treatment was started 5 days (1.25 mg/kg, 2.5 mg/kg and 5 mg/kg) after the tumor implantation, when the average tumors reached approximately 100 mm$^3$. For study B, treatment was started 8 days (0.6 mg/kg, and 10 mg/kg) after the tumor implantation, when the average tumors reached approximately 120 mm$^3$. The treatment scheme is described in Table 5 and Table 6.

TABLE 5

Dosing scheme for study A

| Group | No. of Animals | Treatment | Route and Schedule |
|---|---|---|---|
| A | 6 | Vehicle (1 × PBS) | I.T.*; single dose |
| B | 6 | 5 mg/kg Compound 1a | I.T.; single dose |
| C | 6 | 2.5 mg/kg Compound 1a | I.T.; single dose |
| D | 6 | 1.25 mg/kg Compound 1a | I.T.; single dose |

*I.T. is intratumoral.

TABLE 6

Dosing scheme for study B

| Group | No. of Animals | Treatment | Route and Schedule |
|---|---|---|---|
| A | 5 | Vehicle (1 × PBS) | I.T.*; single dose |
| B | 5 | 10 mg/kg Compound 1a | I.T.; single dose |
| C | 5 | 0.6 mg/kg Compound 1a | I.T.; single dose |

*I.T. is intratumoral.

All the mice in the study have two subcutaneous CT26 tumors. The "treated tumor" indicates the tumor with compound direct administration, while "untreated tumor" indicates the tumor without direct compound administration. Tumor volume was followed throughout the experiment. Tumor volume is measured two times weekly after the start of treatment. Tumor burden is calculated from caliper measurements by the formula for the volume of a prolate ellipsoid (L×W$^2$)/2 where L and W are the respective orthogonal length and width measurements (mm).

Figure 10:
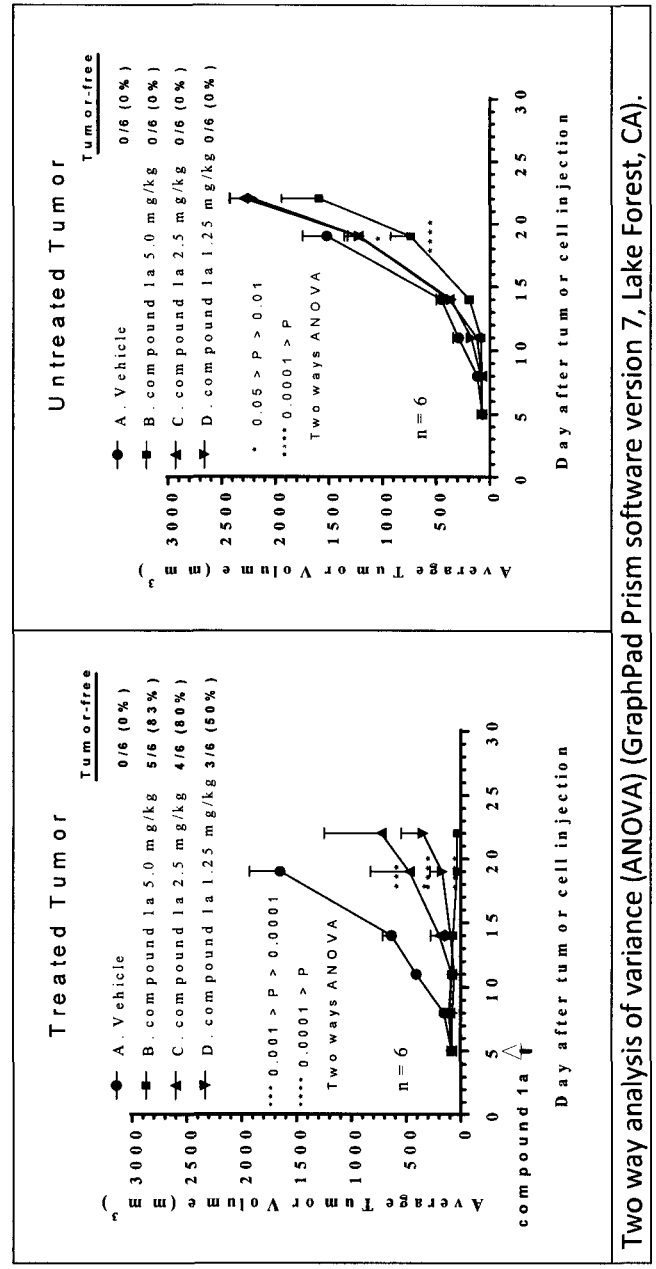
FIG. 10 and FIG. 11 accompany Example 108 and show curative activity of Compound 1a in a CT26 dual tumor model.
Figure 11:
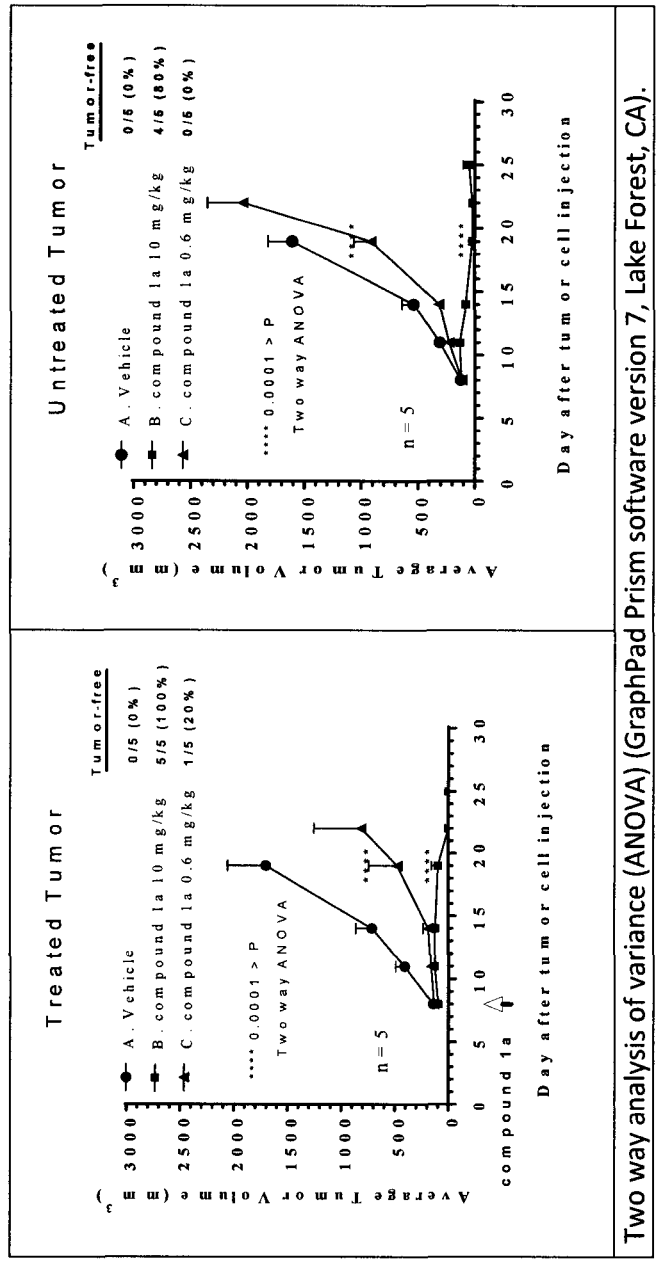

Compound 1a showed potent and curative activity in CT26 dual tumor model (FIG. 10 and FIG. 11). For treated tumors, a cure rate of 20% was detected even at the lowest dose tested in the study (FIG. 8, 0.6 mg/kg dose). At the same time, the highest dose (10 mg/kg) cured 100% of animals of that tumor at the end of study. For the untreated tumors, a dose-dependent anti-tumor effect was also evident. The top dose group (10 mg/kg) showed 80% curative effects; all the lower doses also showed tumor growth inhibition activity. Hence, a therapeutic window of 0.6 mg/kg to 10 mg/kg for Compound 1a was observed, with anti-tumor activity seen not only locally but also systemically, based on effects at the non-injected distal tumor site. In conclusion, these results indicate that local administration of Compound 1a can induce both local and systemic (abscopal) anti-cancer activity.

Example 109—Anti-Cancer Effect of Compound 1a on the CT26 Liver Metastatic Model Compound 1a was tested for its anti-cancer activity in a CT26 liver metastatic model. Anesthetized female 5-6 week-old BALB/cJ mice (Jackson Labs, Bar Harbor, Maine) were implanted intra-splenically with luciferase-expressing CT26 tumor cells (5×10$^5$ cells per mouse). A subsequent ten minute waiting period allowed tumor cells to circulate into the animals' livers. Spleens were then removed and animals were sutured and allowed to recover. Three days later, CT26 tumor cells (10$^5$ cells per mouse) were again implanted, this time subcutaneously (sc) under the right forelimb area, to enable development of a tumor mass for compound administration. Nine days after intra-splenic injection, compound (10 mg/kg) was administered intratumorally, a single time, into the sc tumor.

Figure 12:
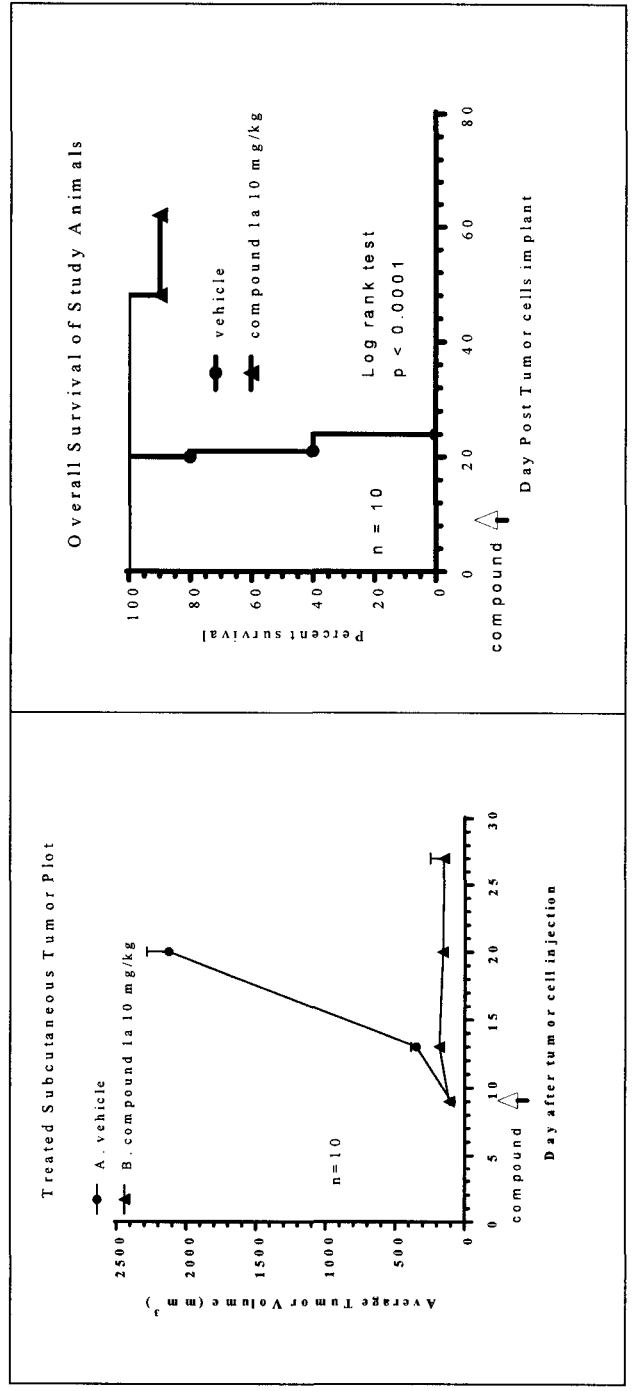
FIG. 12 accompanies Example 109 and shows a tumor volume plot for treated tumors and survival curve.

The local anti-cancer effect of compound was measured through its effect on the sc tumor, while the compound's abscopal effect was assessed by the overall survival of treated mice compared with vehicle-treated control mice, based on the detrimental effect of the growing tumor mass in each mouse liver Compound 1a showed both potent activity towards the local sc tumors and also curative systemic activity in 9 of 10 treated animals (FIG. 12). These results indicate that local administration of Compound 1a can induce both local and systemic (abscopal) anti-cancer activity including deep lesion such as in the liver.

Figure 13:
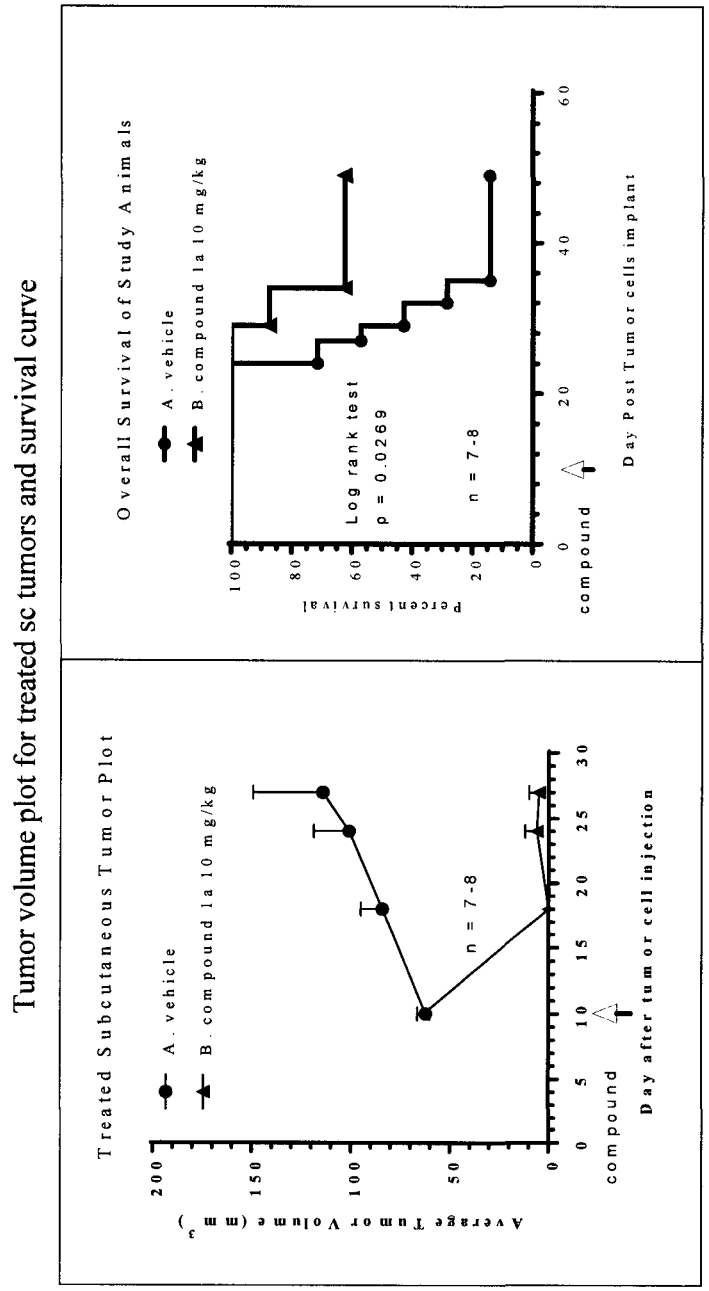
FIG. 13 accompanies Example 110 and shows a tumor volume plot for treated tumors and survival curve.

Example 110—Anti-Cancer Effect of Compound 1a on the GL261 Brain Orthotopic Model Compound 1a was tested for its anti-cancer activity in a GL261 brain orthotopic model. GL261 is a murine glioma cell line. Luciferase expressing GL261 mouse glioma cells (2×10$^4$ cells/mouse) were intra-cranially implanted into female 5-6 week-old B6 albino mice (Jackson Labs, Bar Harbor, Maine). Three to 4 days later, GL261 cells were implanted subcutaneously (10$^6$ cells/mouse) under the right forelimb area to allow development of a tumor mass for compound administration. Ten days after intra-cranial tumor cell implantation, compound (10 mg/kg) was administered intratumorally, a single time, into the sc tumor. The local anti-cancer effect of compound was measured through its effect on the sc tumor, while the compound's abscopal effect was assessed by the overall survival of treated mice compared with vehicle-treated control mice, based on the detrimental effect of the growing tumor mass in each mouse brain. Compound 1a showed both potent activity at local sc tumors and showed curative systemic activity in 5 of 8 treated animals (FIG. 13). These results indicate that local administration of Compound 1a can induce both local and systemic (abscopal) anti-cancer activity including deep lesion such as in the brain.

Example 111—Comparisons

EC50 values were calculated for human STING assays of WT STING, HAQ STING, AQ STING, and REF STING, in head-to-head comparisons using Compound 1a of the present disclosure, a natural STING ligand (2'3' cGAMP), and the purported STING agonist ML RR-S2 CDA, as reported in Corrales, et al., "Direct Activation of STING in the Tumor Microenvironment Leads to Potent and Systemic Tumor Regression and Immunity," *Cell Reports* (2015) 11:1018-1030, which is incorporated by reference herein. Assays were conducted as described in examples set forth above. Note that reported assay values in Table 7 were limited to the assays conducted in the head-to-head comparisons and may not reflect averaged values determined over a greater number of trials as reported above or elsewhere. Note further that "2'3' cGAMP" is the same as "ML cGAMP" as reported in the *Cell Reports* publication.

TABLE 7

| Compound | Kd (WT) (μM) | Human EC$_{50}$ (mM) (20-hr assay) | | | |
|---|---|---|---|---|---|
| | | WT | HAQ | AQ | REF |
| 2'3' cGAMP | 0.07 | 61.7 | 57.9 | 56.5 | 33-100 |
| ML RR-S2 CDA | 0.4 | 5.9 | 8.4 | 5.5 | >100 |
| Compound 1a | 0.04 | 0.6 | 1.9 | 1.0 | 3.9 |

Table 7 also reports dissociation binding constants (Kd) for the binding of human WT STING to each of the three tested compounds, as measured by isothermal titration calorimetry (ITC). ITC is a microcalorimetric titration technique that measures thermodynamic properties associated with intermolecular interactions. Based on these tests, Compound 1a appears to form the strongest bond with WT STING of the tested compounds.

Materials

Recombinant human wild type STING (aa, 139-379, H232R) protein was generated by expressing a construct in *E. coli* encoding a cytosolic domain of human WT STING comprising amino acids 139-379.

Reagents

Sources of reagents used in this study are shown below:

| Reagent | Source | Catalog No. |
|---|---|---|
| 1X PBS without Calcium or Magnesium | Corning | 21-040-CV |
| MilliQ-Deionized Water | MilliQ | Z000Q0V0T0 |
| Liquinox | Alconox | 1201 |
| NaOH | EM | SXO593-1 |
| Methanol | EMD Millipore | MX0475-1 |
| Compounds: Compound 1a 2'3' cGAMP ML RR-S2 CDA | | |

Protein Buffer Preparation

STING protein was stored at −60° C. in 90 μL and 100 μL aliquots each at a concentration of 3.0 mg/ml and 20 mg/mL, respectively in PBS, pH 7.5 containing 5% glycerol. On the day of analysis, aliquots of the protein were thawed, diluted to 400 μL and buffer-exchanged into PBS using an Amicon Ultra centrifugal filter unit (10k MW cutoff, 0.5 mL) with at least four 10 min 14000×g centrifugations with an Eppendorf microcentrifuge and then finally diluted to 20 UM to 30 μM (experiment-dependent) with IX PBS. Protein concentration was determined using a Nanodrop 2000 spectrophotometer and a protein extinction coefficient of 22140 $(M^{-1}cm^{-1})$.

Sample Preparation

Two hundred μL of 1 mM stock solutions of Compound 1a, 2'3' cGAMP, and ML RR-S2CDA were supplied by 1.5 mL microcentrifuge tubes. Prior to each experiment, the samples were diluted to concentrations of 200 μM to 500 μM (experiment-dependent).

Methods

Assays were performed on an Affinity ITC unit (TA Instruments no. 609003.901) equipped with the ITC cleaning accessory (TA Instruments no 601800.901). The STING protein solution, approximately 400 μL containing 20 AM to 30 AM STING protein, was pipetted into the 185 μL calorimeter cell allowing some acceptable overload. The reference cell contained an equivalent amount of Milli-Q water. Incubation was carried out at 25° C. with 20×2.5 μL injections of 100 μM to 300 μM compounds. The control software was ITC Run Ver. 3.3.0.0 (TA Instruments) was used to obtain the thermograms consisting of multiple peaks of raw heat (μcal/sec) representing the heat rate at each injection. The analysis software Nano Analyze Ver. 3.70 (TA Instruments) was used to baseline-correct, correct for blank or sample heat of dilution (at saturation) and to integrate the heat rate peaks producing graphed "Q" values. The resulting isotherms were fit with an independent model to derive the thermodynamic parameters.

The Kds and n values (molar ratios at the curve inflection points) were derived and reported. Optimal conditions for the concentrations of protein and ligand were derived from preliminary experiments.

Results

The heat rate thermograms and their resulting isotherms for the binding of the tested compounds to recombinant human wild type STING (aa, 139-379, H232R) were determined. The binding of each compound to STING was endothermic as indicated by the negative heat rates with exothermic (positive direction) heats of dilution (observed after the compound has achieved saturation of the protein). 2', 3' cGAMP has been shown to produce a similar endothermic response to various STING variants. Compound 1a provided the lowest Kd of 0.04 μM, followed by 2'3' cGAMP with a Kd of 0.07 μM and then ML RR-S2 CDA with a Kd of 0.40 μM. All compounds provided n values close to 0.5, suggesting that the STING protein was present as a dimer and bound 1 mol of compound per 2 mol of STING.

Example 112—Identification of Potential Metabolites

Compound 1a was incubated in hepatocytes of CD-1 mouse, Sprague Dawley rat, Beagle dog, Cynomolgus monkey, and human, to evaluate the formation of major metabolites.

Materials

Cryopreserved pooled hepatocytes were purchased from ThermoFisher Scientific (Waltham, MA), Xenotech, LLC (Kansas City, KS) and In Vitro ADMET Laboratories (Columbia, MD), and the appropriate media were purchased from In Vitro ADMET Laboratories (Columbia, MD) and Life Technologies (Carlsbad, CA). AOPI staining solution and phosphate buffer were obtained from Corning Life Sciences (Tewksbury, MA) and Nexcelom Bioscience (Lawrence, MA), respectively. All chemicals, reagents, and solvents used in analysis were of either analytical or HPLC grade.

Experimental Designs and Procedures

Hepatocyte Incubations

Compound 1a was weighed and dissolved in HPLC-water containing 0.12% formic acid PBS to make 1020 mmol/L. The solution was then diluted 2.5-fold individually to 4 mmol/L and then further diluted 21000-fold with the Williams' E medium containing 0.1% human serum albumin and 2 mmol/L L-glutamine to make the working stock solution with concentration of 20 µmol/L.

Prior to incubations, the cryopreserved hepatocytes were thawed in a water bath at 37° C. One tube of cryopreserved hepatocytes was added to each 50-ml conical tube of cryopreserved hepatocyte recovery medium (UCRM) obtained from In Vitro ADMET Laboratories (Columbia, MD). The cells were spun in a Beckman centrifuge (Brea, CA) with a GH 3.8 rotor at 740 rpm for 10 minutes at room temperature 4° C. The supernatant was removed and the cells were re-suspended in plating media for counting. After the cells were re-suspended in plating media, 20 µL of the re-suspension was transferred and mixed with 20 µL of AOPI staining solution. The solution was gently mixed and cells were counted using a Cellometer (Nexcelom, Lawrence, MA). After counting, the cells were then re-suspended at 1 or 2 million viable cells/mL in Williams' E media containing 2 mmol/L L-glutamine (pH 7.4).

The hepatocyte suspension (50 µL/well) was added into a 48-well plate. Fifty microliters of working stock solution containing Compound 1a (20 µmol/L) were added to start the reaction. The plate was placed into a tissue culture incubator (5% CO2/95% air humidified atmosphere and 37° C.), and the reactions were terminated with 200 µL of stop solution consisting of 100% methanol/acetonitrile (1/1, v/v) with 2010 ng/mL furosemide and 0.2 µmol/L (R)-propranolol at 5, 30, 60, 120, 180 and 240 minutes. The mixture was centrifuged and filtered, and the supernatant was collected for analysis. The final concentrations of cryopreserved hepatocytes were 1×106 cells/mL. The final incubation concentration of Compound 1a was 10 µmol/L.

LC-MS MS Conditions for Metabolite Identification

The LC-MS/MS system was composed of a Shimadzu HPLC and an AB-SCIEX TripleTOF 5600 hybrid quadrupole and TOF mass spectrometer (Framingham, MA). The Shimadzu HPLC (Kyoto, Japan), consisted of a communications bus module (CBM-20A), an auto-sampler (SIL-30AC) with an attached rack changer (Rack Changer II) two pumps (LC-30AD) and a column oven (CTO-30A). The mass spectrometer was calibrated using the AB-SCIEX APCI both Negative and Positive Calibration Solutions (Framingham, MA). The samples obtained from incubations with hepatocytes were analyzed under both negative and positive scan modes. The basic analytical method and instrumental conditions are summarized below. Modification of the spectrometer settings was dependent on the necessity of the analyte.

LC-MS/MS Conditions:

| Chromatography Settings: | Shimadzu LC30AD |
|---|---|
| Column Type | Agilent Eclipse XDB-C8, 5 µ, 2.1x150 mm, part# 993700-906, serial# USSN002817 |
| Mobile Phases | A: water/methanol = 95/5 (v/v) with 5 mM ammonium acetate<br>B: methanol/water = 95/5 (v/v) with 5 mM ammonium acetate |
| Gradients | 0-1 min at 1% B; 1-5 min linear to 10% B; 5-13 min linear to 95% B;<br>13-19.9 min at 95% B; 19.9-20 min linear to 1% B; 20-24 min at 1% B |
| Flow Rate | 0.4 mL/min |
| Analysis Time | 24 min |
| Sample Tray Temperature | 4° C. |
| Injection Volume | 15 µL |
| Mass Spectrometer Settings: | AB Sciex Hybrid Quadrupole-TOF LC-MS/MS Triple TOF 5600 |
| Ion Source | DuoSpray Ion Source |
| Polarity | Negative or Positive |
| Ion Spray Voltage (ISVF) | 4500 V or 5500 V |
| Temperature (TEM) | 550° C. |
| Curtain Gas (CUR) | 30 |
| GS1 | 50 |
| GS2 | 50 |
| TOF-MS Settings: | CE −5.000 or 5.000<br>DP −100.000 or 100.000<br>scan range: 120.0-1000.0 |
| TOF MS^2 Settings: | CE −60.000 or 60.000<br>CES 5.000<br>DP −100.000 or 100.000<br>Scan range: 100.0-1000.0 |

Data Analysis of Activity Data

Mass spectrometry data were acquired using AB-Sciex Analyst TF (Version 1.5.1; Framingham, MA). Chromatograms and spectra were obtained using AB-Sciex Peak View (Version 2.2.0.1; Framingham, MA). The comparison of relative peak areas for extracted ion chromatograms were based on #0.0002 Da of the expected exact mass-to-charge ratio (m/z) for each analyte of interest.

Results

No metabolite was detected from the incubations with hepatocytes. Under the presented analytical conditions, Compound 1a showed a retention time of approximate 7.8 minutes. Under negative scan mode, Compound 1a showed the deprotonated molecular ion m/z 745 ($C_{24}H_{25}F_2N_{10}O_8P_2S_2^-$) and the doubly deprotonated molecular ion m/z 372 ($C_{24}H_{24}F_2N_{10}O_8P_2S_2^{2-}$). The major MS/MS productions with m/z 533 ($C_{19}H_{19}FN_{10}O_4PS^-$) and m/z 186 ($C_9H_8N_5^-$) were observed. Under positive scan mode, Compound 1a showed the protonated molecular ion m/z 747 ($C_{24}H_{27}F_2N_{10}O_8P_2S_2^+$) and the major MS/MS productions with m/z 651 ($C_{24}H_{26}F_2N_{10}O_8PS^+$), m/z 252 ($C_{10}H_{11}FN_5O_2^+$), and m/z 188 ($C_9H_{10}N_5^+$). The MS and MS/MS data are confirmative to the structure of Compound 1a.

Compound 1a was stable in the incubations with hepatocytes of mouse, rat, dog, monkey, and human. No apparent metabolite of Compound 1a was identified in this study. In the samples obtained from incubations with hepatocytes, only Compound 1a itself could be detected and confirmed by the fragments of tandem mass spectrometry (MS/MS).

All documents referenced in this disclosure are incorporated by reference herein, though if any incorporated document contradicts this written specification, then this written specification shall control. Those of skill in the will recognize that various changes and modifications may be made to the material provided herein, and that that material is within the scope and spirit of the disclosure.

SEQUENCE LISTINGS (WT Human STING):
SEQ ID NO: 1
atgccccactccagcctgcatccatccatcccgtgtcccagggtcacggggcccagaaggcagccttggttctgctgagtgcctgcc
tggtgacccttggggggctaggagagccaccagagcacactctccggtacctggtgctccacctagcctccctgcagctgggactgct
gttaaacggggtctgcagcctggctgaggagctgcgccacatccactccaggtaccggggcagctactggaggactgtgcgggcct
gcctgggctgcccctccgccgtggggccctgttgctgctgtccatctatttctactactcccctcccaaatgcggtcggcccgccttca
cttggatgcttgccctcctgggcctctcgcaggcactgaacatcctcctgggcctcaagggcctggcccagctgagatctctgcagtg
tgtgaaaagggaatttcaacgtggcccatgggctggcatggtcatattacatcggatatctgcggctgatcctgccagagctccaggc
ccggattcgaacttacaatcagcattacaacaacctgctacggggtgcagtgagccagcggctgtatattctcctcccattggactgtgg
ggtgcctgataacctgagtatggctgaccccaacattcgcttcctggataaactgccccagcagaccggtgaccgggctggcatcaag
gatcgggtttacagcaacagcatctatgagcttctggagaacgggcagcgggggcacctgtgtcctggagtacgccaccccttg
cagactttgtttgccatgtcacaatacagtcaagctggctttagccgggaggataggcttgagcaggccaaactcttctgccggacactt
gaggacatcctggcagatgcccctgagtctcagaacaactgccgcctcattgcctaccaggaacctgcagatgacagcagcttctcgc
tgtcccaggaggttctccggcacctgcggcaggaggaaaaggaagaggttactgtgggcagcttgaagacctcagcggtgcccagt
acctccacgatgtcccaagagcctgagctcctcatcagtggaatggaaaagcccctccctctccgcacggatttctcttga (REF Human STING):
SEQ ID NO: 2
atgccccactccagcctgcatccatccatcccgtgtcccagggtcacggggcccagaaggcagccttggttctgctgagtgcctgcc
tggtgacccttggggggctaggagagccaccagagcacactctccggtacctggtgctccacctagcctccctgcagctgggactgct
gttaaacggggtctgcagcctggctgaggagctgcgccacatccactccaggtaccggggcagctactggaggactgtgcgggcct
gcctgggctgcccctccgccgtggggccctgttgctgctgtccatctatttctactactcccctcccaaatgcggtcggcccgccttca
cttggatgcttgccctcctgggcctctcgcaggcactgaacatcctcctgggcctcaagggcctggcccagctgagatctctgcagtg
tgtgaaaagggaatttcaacgtggcccatgggctggcatggtcatattacatcggatatctgcggctgatcctgccagagctccaggc
ccggattcgaacttacaatcagcattacaacaacctgctacggggtgcagtgagccagcggctgtatattctcctcccattggactgtgg
ggtgcctgataacctgagtatggctgaccccaacattcgcttcctggataaactgccccagcagaccggtgaccatgctggcatcaag
gatcgggtttacagcaacagcatctatgagcttctggagaacgggcagcgggggcacctgtgtcctggagtacgccaccccttg
cagactttgtttgccatgtcacaatacagtcaagctggctttagccgggaggataggcttgagcaggccaaactcttctgccggacactt
gaggacatcctggcagatgcccctgagtctcagaacaactgccgcctcattgcctaccaggaacctgcagatgacagcagcttctcgc
tgtcccaggaggttctccggcacctgcggcaggaggaaaaggaagaggttactgtgggcagcttgaagacctcagcggtgcccagt
acctccacgatgtcccaagagcctgagctcctcatcagtggaatggaaaagcccctccctctccgcacggatttctcttga (AQ Human STING):
SEQ ID NO: 3
atgccccactccagcctgcatccatccatcccgtgtcccagggtcacggggcccagaaggcagccttggttctgctgagtgcctgcc
tggtgacccttggggggctaggagagccaccagagcacactctccggtacctggtgctccacctagcctccctgcagctgggactgct -continued

```
gttaaacggggtctgcagcctggctgaggagctgcgccacatccactccaggtaccggggcagctactggaggactgtgcgggcct
gcctgggctgccccctccgccgtggggccctgttgctgctgtccatctatttctactaccctcccaaatgcggtcggcccgcccttca
cttggatgcttgccctcctgggcctctcgcaggcactgaacatcctcctgggcctcaagggcctggccccagctgagatctctgcagtg
tgtgaaaaagggaatttcaacgtggcccatgggctggcatggtcatattacatcggatatctgcggctgatcctgccagagctccaggc
ccggattcgaacttacaatcagcattacaacaacctgctacggggtgcagtgagccagcggctgtatattctcctcccattggactgtgg
ggtgcctgataacctgagtatggctgaccccaacattcgcttcctggataaactgccccagcagaccgctgaccgagctggcatcaag
gatcgggtttacagcaacagcatctatgagcttctggagaacgggcagcggggggcacctgtgtcctggagtacgccacccccttg
cagactttgtttgccatgtcacaatacagtcaagctggctttagccggggaggataggcttgagcaggccaaactcttctgccagacactt
gaggacatcctggcagatgcccctgagtctcagaacaactgccgcctcattgcctaccaggaacctgcagatgacagcagcttctcgc
tgtcccaggaggttctccggcacctgcggcaggaggaaaaggaagaggttactgtgggcagcttgaagacctcagcggtgcccagt
acctccacgatgtcccaagagcctgagctcctcatcagtggaatggaaaagcccctccctctccgcacggatttctcttga
```

(WT STING residues 155-341):                                                    SEQ ID NO: 4

VAHGLAWSYYIGYLRLILPELQARIRTYNQHYNNLLRGAVSQRLYILLPLDCGVPDN

LSMADPNIRFLDKLPQQTGDRAGIKDRVYSNSIYELLENGQRAGTCVLEYATPLQTLF

AMSQYSQAGFSREDRLEQAKLFCRTLEDILADAPESQNNCRLIAYQEPADDSSFSLSQ

EVLRHLRQEEKEEV (His-TEV-Sumo-WT STING 155-341)                                                 SEQ ID NO: 5

MHHHHHHSSGVDLGTENLYFQSNAMSDSEVNQEAKPEVKPEVKPETHINLKVSDGS

SEIFFKIKKTTPLRRLMEAFAKRQGKEMDSLRFLYDGIRIQADQTPEDLDMEDNDIIEA

HREQIGGGSVAHGLAWSYYIGYLRLILPELQARIRTYNQHYNNLLRGAVSQRLYILLP

LDCGVPDNLSMADPNIRFLDKLPQQTGDRAGIKDRVYSNSIYELLENGQRAGTCVLE

YATPLQTLFAMSQYSQAGFSREDRLEQAKLFCRTLEDILADAPESQNNCRLIAYQEP

ADDSSFSLSQEVLRHLRQEEKEEV (REF STING residues 155-341):                                                   SEQ ID NO: 6

VAHGLAWSYYIGYLRLILPELQARIRTYNQHYNNLLRGAVSQRLYILLPLDCGVPDN

LSMADPNIRFLDKLPQQTGDHAGIKDRVYSNSIYELLENGQRAGTCVLEYATPLQTL

FAMSQYSQAGFSREDRLEQAKLFCRTLEDILADAPESQNNCRLIAYQEPADDSSFSLS

QEVLRHLRQEEKEEV (His-TEV-Sumo-REF STING 155-341)                                                SEQ ID NO: 7

MHHHHHHSSGVDLGTENLYFQSNAMSDSEVNQEAKPEVKPEVKPETHINLKVSDGS

SEIFFKIKKTTPLRRLMEAFAKRQGKEMDSLRFLYDGIRIQADQTPEDLDMEDNDIIEA

HREQIGGGSVAHGLAWSYYIGYLRLILPELQARIRTYNQHYNNLLRGAVSQRLYILLP

LDCGVPDNLSMADPNIRFLDKLPQQTGDHAGIKDRVYSNSIYELLENGQRAGTCVLE

YATPLQTLFAMSQYSQAGFSREDRLEQAKLFCRTLEDILADAPESQNNCRLIAYQEP

ADDSSFSLSQEVLRHLRQEEKEEV

---

We claim:

1. A method of treating bladder cancer, comprising administering to a patient in need of treatment an effective amount of Compound 1 or a pharmaceutically acceptable salt thereof:

(Compound 1)

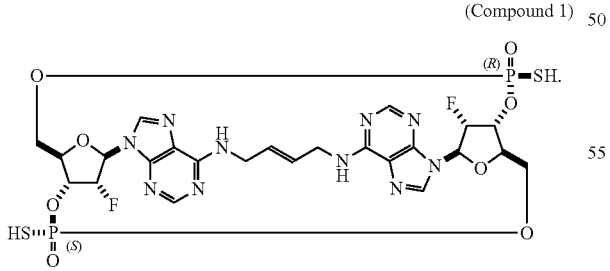

2. The method of claim 1, wherein said pharmaceutically acceptable salt is a diammonium salt.

3. The method of claim 1, wherein said pharmaceutical composition or pharmaceutically acceptable salt thereof is administered as part of a pharmaceutical composition further comprising a pharmaceutically acceptable excipient.

4. A method of treating bladder cancer comprising:
identifying an individual having bladder cancer treatable by Compound 1, a pharmaceutically acceptable salt of Compound 1, or a pharmaceutical composition comprising Compound 1 or a pharmaceutically acceptable salt of Compound 1; and
administering to said individual an effective amount of the compound, pharmaceutically acceptable salt or pharmaceutical composition by which the bladder cancer has been identified as treatable.

5. The method of claim 4, wherein said individual is identified as having a bladder cancer treatable by Compound 1, a pharmaceutically acceptable salt of Compound 1, or a pharmaceutical composition comprising Compound 1 or a pharmaceutically acceptable salt of Compound 1, by a presence of a REF STING variant allele in the patient.

6. A method of treating bladder cancer in a patient having a STING allele selected from the group consisting of a REF STING allele, a WT STING allele, an AQ STING allele, and a HAQ STING allele comprising administering to said patient Compound 1, a pharmaceutically acceptable salt of Compound 1, or a pharmaceutical composition comprising Compound 1 or a pharmaceutically acceptable salt of Compound 1.

7. The method of treating bladder cancer of claim 6, wherein said patient has a WT STING allele.

8. The method of treating bladder cancer of claim 6, wherein said patient has a AQ STING allele.

9. The method of treating bladder cancer of claim 6, wherein said patient has a HAQ STING allele.

10. The method of claim 1, wherein the administration of Compound 1, a pharmaceutically acceptable salt of Compound 1, or a pharmaceutical composition comprising Compound 1 or a pharmaceutically acceptable salt of Compound 1 is conducted intravesicularlly.

11. The method of claim 1, wherein the bladder cancer is non-muscle invasive bladder cancer.

12. The method of treating bladder cancer of claim 6, wherein said patient has a REF STING allele.

* * * * *